US011634709B2

(12) United States Patent
Chee et al.

(10) Patent No.: US 11,634,709 B2
(45) Date of Patent: Apr. 25, 2023

(54) METHODS FOR PREPARING ANALYTES AND RELATED KITS

(71) Applicant: Encodia, Inc., San Diego, CA (US)

(72) Inventors: Mark S. Chee, San Diego, CA (US); Kevin L. Gunderson, San Diego, CA (US); Norihito Muranaka, San Diego, CA (US); Brian Tate Weinert, San Diego, CA (US)

(73) Assignee: Encodia, Inc., San Diego, CA (US)

( * ) Notice: Subject to any disclaimer, the term of this patent is extended or adjusted under 35 U.S.C. 154(b) by 17 days.

(21) Appl. No.: 17/458,199

(22) Filed: Aug. 26, 2021

(65) Prior Publication Data

US 2022/0049246 A1 Feb. 17, 2022

Related U.S. Application Data

(63) Continuation of application No. PCT/US2020/027840, filed on Apr. 10, 2020.

(60) Provisional application No. 62/840,675, filed on Apr. 30, 2019.

(51) Int. Cl.
*C12N 15/10* (2006.01)

(52) U.S. Cl.
CPC .................. *C12N 15/1065* (2013.01)

(58) Field of Classification Search
CPC ............ C12N 15/1065; C12N 15/1093; C12Q 2563/179
See application file for complete search history.

(56) References Cited

U.S. PATENT DOCUMENTS

| | | | |
|---|---|---|---|
| 4,863,870 A | 9/1989 | Stolowitz et al. | |
| 5,049,507 A | 9/1991 | Hawke et al. | |
| 5,770,365 A | 6/1998 | Lane et al. | |
| 5,831,012 A | 11/1998 | Nilsson et al. | |
| 5,834,252 A | 11/1998 | Stemmer | |
| 5,900,481 A | 5/1999 | Lough et al. | |
| 6,060,596 A | 5/2000 | Lerner et al. | |
| 6,511,809 B2 | 1/2003 | Baez et al. | |
| 6,537,749 B2 | 3/2003 | Kuimelis et al. | |
| 6,875,851 B1 | 4/2005 | Travis et al. | |
| 7,169,894 B2 | 1/2007 | Martin | |
| 7,198,900 B2 | 4/2007 | Woudenberg et al. | |
| 7,306,904 B2 | 12/2007 | Landegren et al. | |
| 7,501,237 B2 | 3/2009 | Solus et al. | |
| 7,553,943 B2 * | 6/2009 | Ellis et al. ............. | C07H 21/00 435/6.12 |
| 7,611,834 B2 | 11/2009 | Chhabra et al. | |
| 7,704,925 B2 | 4/2010 | Gouliaev et al. | |
| 7,807,438 B2 | 10/2010 | Abrignani et al. | |
| 8,148,068 B2 | 4/2012 | Brenner | |
| 8,568,994 B2 | 10/2013 | Altevogt et al. | |
| 8,758,991 B2 | 6/2014 | Klein et al. | |
| 9,005,888 B2 | 4/2015 | Antes et al. | |
| 9,039,888 B2 | 5/2015 | Rothberg et al. | |
| 9,085,798 B2 | 7/2015 | Chee | |
| 9,175,340 B2 | 11/2015 | Liu et al. | |
| 9,371,598 B2 | 6/2016 | Chee | |
| 9,435,810 B2 | 9/2016 | Havranek et al. | |
| 9,469,876 B2 | 10/2016 | Kuslich et al. | |
| 9,476,095 B2 | 10/2016 | Vogelstein et al. | |
| 9,528,984 B2 | 12/2016 | Mitra | |
| 9,566,335 B1 | 2/2017 | Emili et al. | |
| 9,574,189 B2 | 2/2017 | Franch et al. | |
| 9,625,469 B2 | 4/2017 | Marcotte et al. | |
| 9,777,315 B2 | 10/2017 | Fredriksson et al. | |
| 9,835,626 B2 | 12/2017 | Schroit et al. | |
| 9,958,448 B2 | 5/2018 | Halbert et al. | |
| 10,011,868 B2 | 7/2018 | Liu et al. | |
| 10,053,725 B2 | 8/2018 | Liu et al. | |
| 10,174,361 B2 | 1/2019 | Skog et al. | |
| 10,287,576 B2 | 5/2019 | Franch et al. | |
| 10,345,310 B2 | 7/2019 | Schroit et al. | |
| 10,428,326 B2 | 10/2019 | Belhocine et al. | |
| 10,465,183 B2 | 11/2019 | Skog et al. | |
| 10,545,153 B2 | 1/2020 | Marcotte et al. | |
| 10,590,407 B2 | 3/2020 | Nguyen et al. | |
| 10,852,305 B2 | 12/2020 | Havranek et al. | |

(Continued)

FOREIGN PATENT DOCUMENTS

| | | | |
|---|---|---|---|
| EP | 0743320 A2 | 11/1996 | |
| EP | 0841945 A1 | 5/1998 | |

(Continued)

OTHER PUBLICATIONS

International Search Report for International application PCT/US2020/027840, dated Sep. 3, 2020, 5 pages.

(Continued)

*Primary Examiner* — Narayan K Bhat
(74) *Attorney, Agent, or Firm* — Morrison & Foerster LLP

(57) ABSTRACT

Provided herein are methods for preparing and treating an analyte (e.g., a macromolecule or a plurality of macromolecules, peptides, polypeptides, and proteins) for analysis. In some embodiments, the analyte is prepared and treated in a method that includes the use of bait and capture nucleic acids, solid supports, and reaction mixtures including the bait and capture nucleic acids. In some embodiments, the analyte is coupled to a solid support. Also provided are kits containing components for performing the provided methods for preparing the analytes. In some embodiments, the methods are for preparing an analyte for sequencing. Provided herein are methods for preparing and treating an analyte (e.g., a macromolecule or a plurality of macromolecules, peptides, polypeptides, and proteins) for analysis. In some embodiments, the analyte is prepared and treated in a method that includes the use of bait and capture nucleic acids, solid supports, and reaction mixtures including the bait and capture nucleic acids. In some embodiments, the analyte is coupled to a solid support. Also provided are kits containing components for performing the provided methods for preparing the analytes. In some embodiments, the methods are for preparing an analyte for sequencing.

30 Claims, 6 Drawing Sheets

Specification includes a Sequence Listing.

(56) References Cited

U.S. PATENT DOCUMENTS

| | | |
|---|---|---|
| 2002/0051986 A1 | 5/2002 | Baez et al. |
| 2002/0058273 A1 | 5/2002 | Shipwash |
| 2003/0087232 A1 | 5/2003 | Christians et al. |
| 2003/0138831 A1 | 7/2003 | Kwagh et al. |
| 2005/0003361 A1 | 1/2005 | Fredriksson |
| 2005/0084927 A1 | 4/2005 | Norioka et al. |
| 2006/0199279 A1 | 9/2006 | Lopez-Avila et al. |
| 2006/0259995 A1 | 11/2006 | Cayouette et al. |
| 2007/0020640 A1 | 1/2007 | Mccloskey et al. |
| 2007/0218503 A1 | 9/2007 | Mitra |
| 2008/0107660 A1 | 5/2008 | Self |
| 2008/0242622 A1* | 10/2008 | Lowe et al. ... C12Y 599/01003 506/10 |
| 2008/0305957 A1 | 12/2008 | Thisted et al. |
| 2009/0048120 A1* | 2/2009 | Park et al. ............ G01Q 60/42 506/9 |
| 2009/0111094 A1* | 4/2009 | Storhoff ........... G01N 33/54366 435/7.1 |
| 2009/0246879 A1 | 10/2009 | Drmanac et al. |
| 2009/0264300 A1 | 10/2009 | Franch et al. |
| 2010/0311114 A1 | 12/2010 | Eyckerman et al. |
| 2011/0136099 A1* | 6/2011 | Schneider et al. .......................... G01N 33/54306 436/526 |
| 2011/0245111 A1 | 10/2011 | Chee |
| 2012/0220494 A1 | 8/2012 | Samuels et al. |
| 2012/0245040 A1 | 9/2012 | Morgan et al. |
| 2013/0052665 A1 | 2/2013 | Ling et al. |
| 2013/0059741 A1 | 3/2013 | Weiner |
| 2013/0288929 A1 | 10/2013 | Hansen et al. |
| 2014/0102915 A1 | 4/2014 | Hu et al. |
| 2014/0273004 A1 | 9/2014 | Havranek et al. |
| 2014/0349860 A1 | 11/2014 | Marcotte et al. |
| 2014/0378322 A1 | 12/2014 | Hindson et al. |
| 2015/0160204 A1 | 6/2015 | Mitra |
| 2015/0185199 A1 | 7/2015 | Joo et al. |
| 2015/0315567 A1 | 11/2015 | Pedersen et al. |
| 2015/0376609 A1 | 12/2015 | Hindson et al. |
| 2015/0376700 A1 | 12/2015 | Schnall-levin et al. |
| 2016/0032379 A1 | 2/2016 | Gloeckner et al. |
| 2016/0054331 A1 | 2/2016 | Stoll et al. |
| 2016/0083786 A1 | 3/2016 | Liu et al. |
| 2016/0122417 A1 | 5/2016 | Shusta et al. |
| 2016/0253584 A1 | 9/2016 | Fodor et al. |
| 2016/0319361 A1 | 11/2016 | Spetzler et al. |
| 2017/0052194 A1 | 2/2017 | Havranek et al. |
| 2017/0074855 A1 | 3/2017 | Morin et al. |
| 2017/0107566 A1 | 4/2017 | Church et al. |
| 2017/0166959 A1 | 6/2017 | Hashimoto et al. |
| 2017/0196818 A1 | 7/2017 | Shin et al. |
| 2017/0247688 A1 | 8/2017 | Franch et al. |
| 2018/0010146 A1* | 1/2018 | Boyne et al. .......... C12N 15/63 |
| 2018/0251825 A1 | 9/2018 | Stoeckius et al. |
| 2018/0320224 A1* | 11/2018 | Gaublomme ........ C12N 15/115 |
| 2018/0363050 A1* | 12/2018 | Hutchison et al. ..... C12N 15/00 |
| 2019/0145982 A1* | 5/2019 | Chee ...................... C40B 70/00 435/6.11 |
| 2019/0219578 A1 | 7/2019 | Mitsuhashi |
| 2019/0257831 A1* | 8/2019 | Rabe Ralam ......... C12N 15/111 |
| 2019/0301985 A1 | 10/2019 | Tao et al. |
| 2020/0018763 A1* | 1/2020 | Lund-Johansen ............................ G01N 33/6848 |
| 2020/0058371 A1* | 2/2020 | Chang et al. .......... G16B 25/10 |
| 2020/0087657 A1* | 3/2020 | Guttman ............. C12N 15/1065 |
| 2020/0087707 A1* | 3/2020 | Engreitz .............. C12Q 1/6804 |
| 2020/0348307 A1 | 11/2020 | Beierle et al. |
| 2020/0348308 A1 | 11/2020 | Chee et al. |
| 2021/0302431 A1 | 9/2021 | Chee et al. |
| 2021/0304839 A1 | 9/2021 | Patel et al. |
| 2021/0355483 A1 | 11/2021 | Chee et al. |
| 2021/0405058 A1 | 12/2021 | Chee et al. |

FOREIGN PATENT DOCUMENTS

| | | | |
|---|---|---|---|
| EP | 2638057 A1 | 9/2013 | |
| EP | 2707381 A1 | 3/2014 | |
| EP | 2748335 A1 | 7/2014 | |
| EP | 2903597 A1 | 8/2015 | |
| EP | 3111212 A1 | 1/2017 | |
| WO | 2000057183 A1 | 9/2000 | |
| WO | WO-0164864 A2 * | 9/2001 | ......... C12N 15/1013 |
| WO | 2005015239 A2 | 2/2005 | |
| WO | 2009050261 A1 | 4/2009 | |
| WO | 2009050261 A9 | 6/2009 | |
| WO | 2010065322 A1 | 6/2010 | |
| WO | 2010065531 A1 | 6/2010 | |
| WO | 2012142213 A2 | 10/2012 | |
| WO | 2012178023 A1 | 12/2012 | |
| WO | 2013112745 A1 | 8/2013 | |
| WO | 2013123442 A1 | 8/2013 | |
| WO | 2013138510 A1 | 9/2013 | |
| WO | 2013142389 A1 | 9/2013 | |
| WO | 2014210225 A1 | 12/2014 | |
| WO | 2015042506 A1 | 3/2015 | |
| WO | 2016019360 A1 | 2/2016 | |
| WO | 2016061517 A2 | 4/2016 | |
| WO | 2016130704 A2 | 8/2016 | |
| WO | 2016138496 A1 | 9/2016 | |
| WO | 2016145416 A2 | 9/2016 | |
| WO | 2015164212 A9 | 10/2016 | |
| WO | 2016164530 A1 | 10/2016 | |
| WO | 2017143006 A1 | 8/2017 | |
| WO | 2017192633 A1 | 11/2017 | |
| WO | 2017205719 A1 | 11/2017 | |
| WO | 2018005720 A1 | 1/2018 | |
| WO | 2018017914 A1 | 1/2018 | |
| WO | 2019089836 A1 | 5/2019 | |
| WO | WO-2019195633 A1 * | 10/2019 | ............. C07K 1/047 |
| WO | 2020223000 A1 | 11/2020 | |

OTHER PUBLICATIONS

Written Opinion of The International Searching Authority for International application PCT/US2020/027840, dated Sep. 33, 2020, 7 pages.

Dahotre SN, et al., Individually addressable and dynamic DNA gates for multiplexed cell sorting Proc Natl Acad Sci U S A. Apr. 24, 2018;115(17):4357-4362.

Welch NG, et al., Orientation and characterization of immobilized antibodies for improved immunoassays (Review). Biointerphases. Mar. 16, 2017;12(2):02D301.

International Preliminary Report on Patentability for International application PCT/US2020/027840, dated May 4, 2021, 41 pages.

Statement under article 34(2)(B) for International application PCT/US2020/027840, dated Feb. 26, 2021, 44 pages.

Akbani, R. et al. (Jul. 2014, e-pub. Apr. 28, 2014). "Realizing the Promise of Reverse Phase Protein Arrays for Clinical, Translational, and Basic Research: A Workshop Report: The RPPA (Reverse Phase Protein Array) Society," Molecular & Cellular Proteomics MCP 13(7):1625-1643.

Alfaro, J. A. et al. (Jun. 2021, e-pub. Jun. 7, 2022). "The Emerging Landscape of Single-Molecule Protein Sequencing Technologies," Nature Methods 18(6):604-617.

Ames, T.D. et al. (Jan./Feb. 2011). "Bacterial Aptamers That Selectively Bind Glutamine," RNA Biology 8:82-89.

Amini, S. et al. (Dec. 2014). "Haplotype-Resolved Whole-Genome Sequencing by Contiguity Preserving Transposition and Combinatorial Indexing," Nature Genetics 46(12):1343-1349, 21 pages.

Assadi, M. et al. (Sep. 2013, e-pub. May 7, 2013). "Multiple Protein Analysis of Formalin-Fixed and Paraffin-Embedded Tissue Samples With Reverse Phase Protein Arrays," Molecular & Cellular Proteomics: MCP 12(9):2615-2622.

Bailey, J. M. et al. (Mar. 27, 1990). "Carboxy-Terminal Sequencing: Formation and Hydrolysis of C-Terminal Peptidylthiohydantoins," Biochemistry 29(12):3145-3156.

Ballester, L.Y. et al. (2016, e-pub. Jan. 18, 2016). "Advances in Clinical Next-Generation Sequencing: Target Enrichment and Sequencing Technologies," Expert Review of Molecular Diagnostics 16(3):357-372.

(56) References Cited

OTHER PUBLICATIONS

Bandara, H.M.D. et al. (2009, e-pub Jul. 27, 2009). "Photoinduced Release of Zn2+ With Zincleav-1: A Nitrobenzyl-Based Caged Complex," Inorganic Chemistry 48(17):8445-8555.

Bandara, H.M.D. et al. (Mar. 28, 2011, e-pub Mar. 1, 2011). "A Second-Generation Photocage for Zn2+ Inspired by TPEN: Characterization and Insight Into the Uncaging Quantum Yields of Zincleav Chelators," Chemistry 17(14):3932-3941.

Banta, S. et al. (2013, e-pub. Apr. 29, 2013). "Replacing Antibodies: Engineering New Binding Proteins," Annu. Rev. Biomed. Eng. 15:93-113.

Barrett, G.C. et al. (1985). "Edman Stepwise Degradation of Polypeptides: A New Strategy Employing Mild Basic Cleavage Conditions," Tetrahedron Lett. 26(36):4375-4378.

Basle, E. et al. (Mar. 26, 2010). "Protein Chemical Modification on Endogenous Amino Acids," Chem Biol 17(3):213-227.

Bell, J.C. et al. (Nov. 8, 2012, e-pub. Oct. 24, 2012). "Direct Imaging of RecA Nucleation and Growth on Single Molecules of SSB-Coated ssDNA." Nature 491(7423):274-278.

Bell, J.C. et al. (Sep. 18, 2015), "Imaging and Energetics of Single SSB-ssDNA Molecules Reveal Intramolecular Condensation and Insight into RecOR Function," Elife. 4:e08646, 21 pages.

Ben-Meir, D. et al. (Feb. 15, 1993). "Specificity of *Streptomyces griseus* Aminopeptidase and Modulation of Activity by Divalent Metal Ion Binding and Substitution," European Journal of Biochemistry 212(1):107-112.

Bilgicer, B. et al. (Jul. 8, 2009). "A Non-Chromatographic Method for the Purification of a Bivalently Active Monoclonal IgG Antibody From Biological Fluids," J Am Chem Soc 131(26):9361-9367.

Bochman, M. L. et al. (Nov. 2012, e-pub. Oct. 3, 2012). "DNA Secondary Structures: Stability and Function of G-Quadruplex Structures," Nat Rev Genet 13(11):770-780, 25 pages.

Bodi, K. et al. (Jul. 2013). "Comparison of Commercially Available Target Enrichment Methods for Next-Generation Sequencing," Journal of Biomolecular Techniques: JBT 24(2):73-86.

Borgo, B. et al. (Mar. 2014, e-pub. Feb. 4, 2014). "Motif-Directed Redesign of Enzyme Specificity," Protein Sci 23(3):312-320.

Brouzes, E. et al. (Aug. 25, 2009, e-pub. Jul. 15, 2009). "Droplet Microfluidic Technology for Single-Cell High-Throughput Screening," Proc Natl Acad Sci USA 106(34):14195-14200.

Brudno, Y. et al. (Feb. 2010, e-pub. Dec. 27, 2009). "An In Vitro Translation, Selection and Amplification System for Peptide Nucleic Acids," Nat Chem Biol 6(2):148-155, 23 pages.

Buschmann, T. et al. (Sep. 11, 2013). "Levenshtein Error-Correcting Barcodes for Multiplexed DNA Sequencing," BMC Bioinformatics 14(272):1-10.

Calcagno, S. et al. (Aug. 2016, e-pub. Mar. 29, 2016). "N-Terminal Methionine Processing by the Zinc-Activated Plasmodium Falciparum Methionine Aminopeptidase 1b," Appl Microbiol Biotechnol 100(16):7091-7102.

Camarero, J.A. et al. (Nov. 17, 2004, e-pub. Oct. 23, 2004). "Chemoselective Attachment of Biologically Active Proteins to Surfaces by Expressed Protein Ligation and Its Application for "Protein Chip" Fabrication," Journal of the American Chemical Society 126(45):14730-14731.

Cao, Y. et al. (Dec. 18, 2015). "Butelase-Mediated Synthesis of Protein Thioesters and Its Application for Tandem Chemoenzymatic Ligation," Chem Commun (Camb) 51(97):17289-17292.

Carty, R.P. et al. (Oct. 25, 1968). "Modification of Bovine Pancreatic Ribonuclease A With 4-Sulfonyloxy-2-Nitrofluorobenzene. Isolation and Identification of Modified Proteins," J Biol Chem 243(20):5244-5253.

Cazalis, C.S. et al. (Sep./Oct. 2004). "C-Terminal Site-Specific PEGylation of a Truncated Thrombomodulin Mutant With Retention of Full Bioactivity," Bioconjugate Chemistry 15(5):1005-1009.

Champoux, J. J. (2001). "DNA Topoisomerases: Structure, Function, and Mechanism," Annual Review of Biochemistry 70:369-413.

Chan, A. et al. (Jun. 2015, e-pub. Feb. 24, 2015). "Novel Selection Methods for DNA-Encoded Chemical Libraries," Current Opinion in Chemical Biology 26:55-61.

Chan, L. et al. (Nov. 14, 2007). "Covalent Attachment of Proteins to Solid Supports and Surfaces via Sortase-Mediated Ligation," PloS One 2(11):e1164, 5pgs.

Chang, L. et al. (Apr. 30, 2012, e-pub. Feb. 20, 2012). "Single Molecule Enzyme-Linked Immunosorbent Assays: Theoretical Considerations," J Immunol Methods 378(1-2):102-115.

Chang, Y.Y. et al. (Mar. 2, 2015). "Structural Basis for Substrate-Specific Acetylation of Nalpha-Acetyltransferase Ard1 From Sulfolobus Solfataricus," Sci Rep. 5:8673, 1-9 pages.

Chen, D. et al. (Apr. 1, 2017, e-pub, Jan. 9, 2017). "Selective N-Terminal Functionalization of Native Peptides and Proteins," Chemical Science 8(4):2717-2722.

Christoforou, A. et al. (Jan. 12, 2016). "A Draft Map of the Mouse Pluripotent Stem Cell Spatial Proteome," Nat Commun 7:8992, 1-12 pages.

Colas, P. (Feb. 2000). "Combinatorial Protein Reagents to Manipulate Protein Function," Current Opinion in Chemical Biology 4(1):54-59.

Creighton, C. J. et al. (Jul. 7, 2015). "Reverse Phase Protein Arrays in Signaling Pathways: A Data Integration Perspective," Drug Des Devel Ther. 5(9):3519-3527.

Croseito, N. et al. (Jan. 2015, e-pub. Dec. 2, 2014). "Spatially Resolved Transcriptomics and Beyond," Nat Rev Genet. 16(1):57-66.

Cusanovich, D.A. et al. (May 22, 2015, e-pub. May 7, 2015). "Multiplex Single-Cell Profiling of Chromatin Accessibility by Combinatorial Cellular Indexing," Science 348(6237):910-914.

Davidson, G.R. et al. (2011). "Positional Proteomics at The N-Terminus as a Means of Proteome Simplification," Methods in Molecular Biology 753:229-242.

Decreau, R.A. et al. (Apr. 13, 2007, e-pub. Mar. 22, 2007). "Syntheses of Hemoprotein Models That Can Be Covalently Attached Onto Electrode Surfaces by Click Chemistry," The Journal of Organic Chemistry 72(8):2794-2802.

Derrington, I.M. et al. (Sep. 14, 2010, e-pub. Aug. 26, 2010), "Nanopore DNA Sequencing with MspA," Proc Natl Acad Sci USA 107(37): 16060-16065.

Dragulescu-Andrasi, A. et al. (Aug. 9, 2006). "A Simple Gamma-Backbone Modification Preorganizes Peptide Nucleic Acid Into a Helical Structure," Journal of the American Chemical Society 128(31):10258-10267.

Drmanac, R. et al. (Jan. 1, 2010, e-pub. Nov. 5, 2009). "Human Genome Sequencing Using Unchained Base Reads on Self-Assembling DNA Nanoarrays," Science 327(5961):78-81.

Du, Z. et al. (Jul. 2003). "Amplification of High-Quantity Serial Analysis of Gene Expression Ditags and Improvement of Concatemer Cloning Efficiency," BioTechniques 35(1):66-72.

El-Sagheer, A. H. et al. (Jan. 7, 2011, e-pub. Nov. 11, 2010). "Rapid Chemical Ligation of Oligonucleotides by the Diels-Alder Reaction," Org Biomol Chem 9(1):232-235.

El-Sagheer, A. H. et al. (Jul. 12, 2011, e-pub. Jun. 27, 2011). "Biocompatible Artificial DNA Linker That is Read Through by DNA Polymerases and is Functional in *Escherichia coli*," Proc Natl Acad Sci USA 108(28):11338-11343.

Erde, J. et al. (Apr. 4, 2014, e-pub. Mar. 6, 2014). "Enhanced FASP (eFASP) to Increase Proteome Coverage and Sample Recovery for Quantitative Proteomic Experiments," J Proteome Res 13(4):1885-1895.

Eriquez, L.A. et al. (Nov. 1980), "Aminopeptidases Highly Specific for Glutamyl Residues From Neisseria Meningitidis and Moraxella Urethralis," Journal of Clinical Microbiology 12(5):667-671.

European Search Report for EP Application 18874783.6, dated Sep. 27, 2021, 8 pages.

Extended European Search Report for European Patent Application EP17793198.7, dated Nov. 7, 2019, 11 Pages.

Famulok, M. et al. (Mar. 1, 1994), "Molecular Recognition of Amino Acids by RNA-Aptamers: An L-Citrulline Binding RNA Motif and its Evolution into an L-Arginine Binder," J. Am. Chem. Soc. 116(5):1698-1706.

(56) References Cited

OTHER PUBLICATIONS

Fan, C.H. et al. (Feb. 6, 2015). "Combinatorial Labeling of Single Cells for Gene Expression Cytometry," Science 347(6222):1258367, 10 pages.
Farries, T.C. et al. (Mar. 28, 1991). "Removal of N-Acetyl Groups From Blocked Peptides With Acylpeptide Hydrolase. Stabilization of the Enzyme and Its Application to Protein Sequencing," Eur J Biochem 196(3):679-685.
Feist, P. et al. (Feb. 5, 2015). "Proteomic Challenges: Sample Preparation Techniques for Microgram-Quantity Protein Analysis From Biological Samples," Int J Mol Sci 16(2):3537-3563.
Fernandez-Gacio, A. et al. (Sep. 2003). "Phage Display as a Tool for the Directed Evolution of Enzymes," Trends in Biotechnology 21(9):408-414.
Fowler, E. et al. (May 2001). "Removal of N-Terminai Blocking Groups From Proteins," Current Protocols in Protein Science Chapter 11:11.1-11.17.
Friedmann, D.R. et al. (Nov. 2013, e-pub. Jun. 28, 2013). "Structure and Mechanism of Non-Histone Protein Acetyltransferase Enzymes," FEBS J 280(22):5570-5581.
Frokjaer, S. et al. (Apr. 2005). "Protein Drug Stability: A Formulation Challenge," Nat. Rev. Drug. Discov. 4(4):298-306.
Fujii, Y. et al. (Mar. 2014, e-pub. Jan. 28, 2014). "PA Tag: A Versatile Protein Tagging System Using a Super High Affinity Antibody Against a Dodecapeptide Derived From Human Podoplanin," Protein Expr Purif 95:240-247.
Gabrys, R. et al. (Jun. 2, 2015). "Asymmetric Lee Distance Codes for DNA-based Storage," IEEE Symposium on Information Theory (ISIT) 63(8):4982-4995, 19 pages.
Gamper, H.B. et al. (Jun. 6, 2006). "Unrestricted Hybridization of Oligonucleotides to Structure-free DNA," Biochemistry 45(22):6978-6986.
Gebauer, M. et al. (2012). "Anticalins: Small Engineered Binding Proteins Based on the Lipocalin Scaffold," Methods Enzymol 503:157-188.
Genshaft, A.S. et al. (Sep. 19, 2016). "Multiplexed, Targeted Profiling of Single-Cell Proteomes and Transcriptomes in a Single Reaction," Genome Biol. 17(1):188, 1-15 pages.
Gerry, N. P. et al. (Sep. 17, 1999). "Universal DNA Microarray Method for Multiplex Detection of Low Abundance Point Mutations," J Mol Biol 292(2):251-262.
Girish, A. et al. (May 16, 2005). "Site-Specific Immobilization of Proteins in a Microarray Using Intein-Mediated Protein Splicing," Bioorg. Med. Chem. Lett. 15(10):2447-2451.
Gogliettino, M. et al. (2012, e-pub. May 24, 2012). "Identirication and Characterization of a Novel Acylpeptide Hydrolase From Sulfolobus Solfataricus: Structural and Functional Insights," PLoS One 7(5): e37921, 13 pages.
Gogliettino, M. et al. (Jan. 2014, e-pub. Dec. 10, 2013). "A Novel Class of Bifunctional Acylpeptide Hydrolases—Potential Role in the Antioxidant Defense Systems of the Antarctic Fish Trematomus Bernacchii," FEBS J 281(1):401-415.
Gold, L. et al. (1995). "Diversity of Oligonucleotide Functions," Annu. Rev. Biochem. 64:763-797.
Granvogl, B. et al., (Oct. 2007, e-pub. Jul. 17, 2007). "Sample Preparation by In-Gel Digestion for Mass Spectrometry-Based Proteomics," Anal Bioanal Chem 389(4):991-1002.
Groll, J. et al. (2010). "Star Polymer Surface Passivation for Single-Molecule Detection," Methods Enzymol. 472:1-18.
Groll, J. et al. (Mar./Apr. 2005) "Comparison of Coatings From Reactive Star Shaped PEG-Stat-PPG Prepolymers and Grafted Linear PEG for Biological and Medical Applications," Biomacromoiecules 6(2):956-962.
Gunderson, K.L. et al. (May 2004, e-pub. Apr. 12, 2004). "Decoding Randomly Ordered DNA Arrays," Genome Res. 14(5):870-877.
Gunderson, K.L. et al. (Nov. 1998). "Mutation Detection by Ligation to Complete N-Mer DNA Arrays," Genome Res 8(11):1142-1153.
Guo, H. et al. (Sep. 24, 2012). "An Efficient Procedure for Protein Extraction From Formalin-Fixed, Paraffin-Embedded Tissues for Reverse Phase Protein Arrays," Proteome Sci 10(1):56, 1-12 pages.
Gupta, A. et al. (Mar. 21, 2016). "Nanoemulsions: Formation, Properties and Applications," Soft Matter. 12(11):2826-2841.
Halpin, D.R. et al. (Jul. 2004, e-pub. Jun. 22, 2004). "DNA Display III. Solid-Phase Organic Synthesis on Unprotected DNA," PLoS Biol 2(7):e175, 1031-1038.
Hamada, Y. (Apr. 1, 2016, e-pub. Feb. 21, 2016). "A Novel N-Terminal Degradation Reaction of Peptides via N-Amidination," Bioorg Med Chem Lett 26(7):1690-1695.
Harris, T.D. et al. (Apr. 4, 2008). "Single-Molecule DNA Sequencing of a Viral Genome," Science 320(5872):106-109.
Hennessy, B.T. et al. (Dec. 2010). "A Technical Assessment of the Utility of Reverse Phase Protein Arrays for the Study of the Functional Proteome in Non-microdissected Human Breast Cancers," Clinical Proteomics 6(4):129-151.
Hernandez-Moreno, A.V. et al. (2014). "Kinetics and Conformational Stability Studies of Recombinant Leucine Aminopeptidase," Int J Biol Macromol 64: 306-312.
Hori, M. et al. (2007). "Uniform Amplification of Multiple DNAs by Emulsion PCR," Biochem Biophys Res Commun 352(2): 323-328.
Horisawa, K. (2014). "Specific and Quantitative Labeling of Biomolecules Using Click Chemistry," Front Physiol 5(457):1-6.
Hoshika, D. et al. (2010). "Artificial Genetic Systems: Self-Avoiding DNA in PCR and Multiplexed PCR," Angewandte Chemie (International ed. in English) 49(32):5554-5557.
Hua, B. et al. (2014). "An Improved Surface Passivation Method for Single-Molecule Studies," Nat. Methods 11(12):1233-1236, 13 pages.
Huang, J. et al. (2014). "Enrichment and Separation Techniques for Large-Scale Proteomics Analysis of the Protein Post-Translational Modifications," J. Chromato. 1372:1-17.
Hughes, A.J. et al. (2014). "Single-Cell Western Blotting," Nat Methods 11(7): 749-755.
Hughes, C.S. et al. (2014). "Ultrasensitive Proteome Analysis Using Paramagnetic Bead Technology," Mol Syst Biol 10(75):1-14.
International Preliminary Report on Patentability for International Application PCT/US2018/058565, dated May 5, 2020, filed Oct. 31, 2018, 26 pages.
International Preliminary Report on Patentability for International Application PCT/US2018/058575, dated May 5, 2020, filed Oct. 31, 2018, 8 pages.
International Preliminary Report on Patentability for International Application PCT/US2018/058583, dated May 5, 2020, filed Oct. 31, 2018, 9 pages.
International Preliminary Report on Patentability for international Patent Application PCT/US2017/30702, dated May 16, 2018, filed May 2, 2017, 95 Pages.
International Search Report for International Application PCT/US2017/030702, dated Sep. 8, 2017, filed May 2, 2017, 6 pages.
International Search Report for international Application PCT/US2018/058565, dated Jan. 29, 2019, filed Oct. 31, 2018, 5 pages.
International Search Report for international Application PCT/US2018/058575, dated Apr. 15, 2019, filed Oct. 31, 2018, 6 pages.
International Search Report for International Application PCT/US2018/058583, dated Jan. 22, 2019, filed Oct. 31, 2018, 4 pages.
Jayasena, S.D. (1999). "Aptamers: An Emerging Class of Molecules That Rival Antibodies in Diagnostics," Clin Chem 45(9):1628-1650.
Kalia, J. et al. (2007). "General Method for Site-Specific Protein Immobilization by Staudinger Ligation," Bioconjug. Chem. 18:1064-1069.
Kang, C.C. et al. (2016). "Single Cell-Resolution Western Blotting," Nat Protoc 11(8): 1508-1530.
Kang, T.S. et al. (2010). "Converting an Injectable Protein Therapeutic Into an Oral Form: Phenylalanine Ammonia Lyase for Phenylketonuria," Mol Genet Metab 99(1): 4-9, 14 pages.
Katritzky, A. R. et al. (2005). "Recent Developments In Guanylating Agents," ARKIVOC (IV):49-87.
Kiah, H.M. et al. (2015). "Codes for DNA Sequence Profiles," IEEE International Symposium on Information Theory (ISIT) 62(6):3125-3146, 5 pages.

(56) References Cited

OTHER PUBLICATIONS

Kishor, N. et al. (2015). "Direct N-Terminal Sequencing of Polypeptides Using a Thermostable Bacterial Aminopeptidase and MALDI-TOF Mass Spectrometry," Anal. Biochem. 488:6-8.

Klein, A.M. et al. (2015), "Droplet Barcoding for Single-Cell Transcriptomics Applied to Embryonic Stem Cells," Cell 161(5):1187-1201.

Knall, A-C. et al. (2014). "Kinetic Studies of Inverse Electron Demand Diels-Alder Reactions (Iedda) of Norbomenes and 3,6-Dipyrldin-2-Yl-1,2,4,5-Tetrazine," Tetrahedron Lett 55(34):4763-4766.

Kodal, A.L.B. et al. (2016). "DNA-Templated Introduction of an Aldehyde Handle in Proteins," ChemBioChem 17:1338-1342.

Korlach, J. et al. (2008). "Selective Aluminum Passivation for Targeted Immobilization of Single DNA Polymerase Molecules in Zero-Mode Waveguide Nanostructures," Proc. Natl. Acad. Sci. 105:1176-1181.

Krishna, R.G. et al. (1991). "N-Terminal Sequence Analysis of N Alpha-Acetylated Proteins After Unblocking With N-Acylaminoacyl-Peptide Hydrolase," Anal. Biochem. 199:45-50.

Kusser, W. et al. (2000). "Chemically Modified Nucleic Acid Aptamers for in Vitro Selections: Evolving Evolution," J. Biotechnol 74: 27-38.

Lahoud, G. et al. (2008). "Enzymatic Synthesis of Structure-Free DNA With Pseudo-Complementary Properties," Nucleic Acids Res. 36(10):3409-3419.

Laszlo, A.H. et al., (2014), "Decoding Long Nanopore Sequencing Reads of Natural DNA," Nat. Biotechnol. 32(8):829-833.

Laure, C. et al. (2016). "Coding in 2D: Using Intentional Dispersity to Enhance the Information Capacity of Sequence-Coded Polymer Barcodes," Angew. Chem. Int. Ed. 55(36):10722-10725.

Le, Z.G. et al. (2005). "Organic Reactions in Ionic Liquids: Ionic Liquid-promoted Efficient Synthesis of Disubstituted and Trisubstituted Thioureas Derivatives," Chinese Chemical Letters 16(2): 201-204.

Lesch, V. et al., (2015). "Peptides in the Presence of Aqueous Ionic Liquids: Tunable Co-Solutes as Denaturants or Protectants?" Phys Chem Phys 17(39): 26049-26053.

Li, G. et al. (2013). "Photoaffinity Labeling of Small-Molecule-Binding Proteins by DNA-Templated Chemistry," Angew Chem Int Ed Engl 52(36): 9544-9549.

Li, G. et al. (2014). "Multivalent Photoaffinity Probe for Labeling Small Molecule Binding Proteins," Bioconjug Chem. 25(6):1172-1180.

Li, L. et al. (Jan. 2014). "Structural Analysis and Optimization of the Covalent Association between SpyCatcher and a Peptide Tag," J Mol Biol. 426(2):309-317, 15 pages.

Liao, Y-D. et al. (2004). "Removal of N-Terminal Methionine From Recombinant Proteins by Engineered E. coli Methionine Aminopeptidase," Prot. Sci. 13:1802-1810.

Liebscher, S. et al. (2014). "N-1erminal Protein Modification by Substrate-Activated Reverse Proteolysis," Angew Chem Int Ed Engl 53:3024-3028.

Litovchick, A. et al. (2014). "Universal Strategies for the DNA-Encoding of Libraries of Small Molecules Using the Chemical Ligation of Oligonucleotide Tags," Artif DNA PNA XNA 5(1):e27896-1-e27896-11.

Liu, Y. et al. (2001). "Chemical Carboxyl-Terminal Sequence Analysis of Peptides and Proteins Using Tribenzylsilyl Isothiocyanate," J Protein Chem 20(7): 535-541.

Los, G.V. et al. (2008). "HaloTag: A Novel Protein Labeling Technology for Cell Imaging and Protein Analysis," ACS Chem. Biol. 3(6):373-382.

Lu, K. et al. (2010). "Chemical Strategies for the Synthesis of Peptide-Oligonucleotide Conjugates," Bioconjug. Chem. 21(2):187-202.

Lund, V. et al. (1988), "Assessment of Methods for Covalent Binding of Nucleic Acids to Magnetic Beads, Dynabeads, and the Characteristics of the Bound Nucleic Acids in Hybridization Reactions," Nucleic Acids Res. 16(22):10861-10880.

Lutz, J. F. (2015). "Coding Macromolecules: Inputting Information in Polymers Using Monomer-Based Alphabets," Macromolecules 48:4759-4767.

Macosko, E.Z. et al. (May 21, 2015). "Highly Parallel Genome-Wide Expression Profiling of Individual Cells Using Nanoliter Droplets," Cell 161:1202-1214.

Mamanova, L. et al. (2010). "Target-Enrichment Strategies for Next-Generation Sequencing," Nature Methods 7(2):111-118.

Mannironi, C. et al. (2000). "Molecular Recognition of Amino Acids by RNA Aptamers: The Evolution Into An L-Tyrosine Binder of a Dopamine-Binding RNA Motif," RNA 6:520-527.

Marx, V. (2015). "Mapping Proteins With Spatial Proteomics," Nat Methods 12(9):815-819.

Mashaghi, S. et al. (2015), "External Control Of Reactions in Microdroplets," Sci Rep 5(11837):1-8.

Maynard, J. et al. (2000). "Antibody Engineering," Annu Rev Biomed Eng 2:339-376.

McCormick, R.M. et al. (1989). "A Solid-Phase Extraction Procedure for DNA Purification," Anal Biochem 181(1):66-74.

McGregor, L.M. et al. (2014). "Identification of Ligand-Target Pairs from Combined Libraries of Small Molecules and Unpurified Protein Targets in Cell Lysates," Journal of the American Chemical Society 136:3264-3270.

McKay, C.S. et al. (Sep. 18, 2014). "Click Chemistry in Complex Mixtures: Bioorthogonal Bioconjugation," Chemistry & Biology 21:1015-1101.

Melkko, S. et al. (Jun. 2007). "Lead Discovery by DNA-Encoded Chemical Libraries," Drug Discovery Today 12(11/12):465-471, 7pages.

Mendoza, V.L. et al. (2009). "Probing Protein Structure by Amino Acid-Specific Covalent Labeling and Mass Spectrometry," Mass Spectrom Rev 28(5): 785-815.

Mertes, F. et al. (2011). "Targeted Enrichment of Genomic DNA Regions for Next-Generation Sequencing," Brief Funct. Genomics 10(6):374-386.

Mikami, T. et al. (2012). "N (alpha) Selective Acetylation of Peptides," Mass Spectrom 1(2): A0010, 1-3.

Moghaddam, M.J. et al. (2012). "Chelating DTPA Amphiphiles: Ion-Tunable Self-Assembly Structures and Gadolinium Complexes," Phys Chem Phys 14(37):12854-12862.

Muecke, M. et al. (2008). "Preparation of Multimilligram Quantities of Large, Linear DNA Molecules for Structural Studies," Structure 16:837-841.

Mukherjee et al. (2015). "A New Versatile Immobilization Tag Based on the Ultra High Affinity and Reversibility of the Calmodulin-Calmodulin Binding Peptide Interaction," J Mol Biol 427(16): 2707-2725.

Namimatsu, S. et al. (2005). "Reversing the Effects of Formalin Fixation With Citraconic Anhydride and Heat: A Universal Antigen Retrieval Method," J Histochem Cytochem 53(1): 3-11.

Nguyen, G.K.T. et al. (2014). "Butelase 1 Is an Asx-Specific Ligase Enabling Peptide Macrocyclization and Synthesis," Nat Chem Biol 10(9): 732-738.

Nguyen, G.K.T. et al. (2015). "Butelase 1: A Versatile Ligase for Peptide and Protein Macrocyclization," J Am Chem Soc. 137(49):15398-15401.

Nguyen, G.K.T. et al. (2015). "Site-Specific N-Terminal Labeling of Peptides and Proteins Using Butelase 1 and Thiodepsipeptide," Angew Chem Int Ed Engl 54(52):15694-15698.

Nguyen, G.K.T. et al. (2016). "Butelase-Mediated Cyclization and Ligation of Peptides and Proteins," Nat Protoc. 11(10):1977-1988.

Nilsson, M. et al. (1994). "Padlock Probes: Circularizing Oligonucleotides for Localized DNA Detection," Science 265:2085-2088.

Nishikawa, T. et al. (2012). "Directed Evolution of Proteins Through In Vitro Protein Synthesis in Liposomes" J Nucleic Acids. 2012(923214):1-11.

Nishizuka, S.S. et al. (2016). "New Era of Integrated Cancer Biomarker Discovery Using Reverse-Phase Protein Arrays," Druq Metab Pharmacokinet 31(1): 35-45.

Niu, J. et al. (2013). "Enzyme-Free Translation of DNA into Sequence-Defined Synthetic Polymers Structurally Unrelated to Nucleic Acids," Nat. Chem. 5(4):282-292.

(56) References Cited

OTHER PUBLICATIONS

Ohkubo, A. et al. (2008). "'Protected DNA Probes' Capable of Strong Hybridization Without Removal of Base Protecting Groups," Nucleic Acids Res 36(6):1952-1964.
Ohshiro, T. et al. (2012). "Single-Molecule Electrical Random Resequencing of DNA and RNA," Sci Rep 2(501):1 -7.
Ojha, B. et al. (2010). "2-Alkylmalonic Acid: Amphiphilic Chelator and a Potent Inhibitor of Metalloenzyme," J Phys Chem B 114(33):10835-10842.
Pan, H. et al. (2015). "A Simple Procedure to Improve the Surface Passivation for Single Molecule Fluorescence Studies," Phys. Biol. 12(045006):8 pages.
Park, J. et al. (2016). "Investigation of Specific Binding Proteins to Photoaffinity Linkers for Efficient Deconvolution of Target Protein," ACS Chem Biol. 11(1):44-52.
Parthasarathy, R. et al. (2007). "Sortase A as a Novel Molecular "Stapler" for Sequence-Specific Protein Conjugation," Bioconjugate Chem. 18(2):469-476.
Patel, D.J. et al. (2000). "Structure, Recognition and Discrimination in RNA Aptamer Complexes With Cofactors, Amino Acids, Drugs and Aminoglycoside Antibiotics," J. Biotech. 74:39-60.
Peng, X. et al. (2010). "A Template-Mediated Click-Click Reaction: PNA-DNA, PNA-PNA (or Peptide) Ligation, and Single Nucleotide Discrimination," European J Org Chem (22): 4194-4197, 12 pages.
Perbandt, M. et al. (2007). "High Resolution Structure of Streptavidin in Complex With a Novel High Affinity Peptide Tag Mimicking the Biotin Binding Motif," Proteins 67(4): 1147-1153.
Ponsard, I. et al. (2001), "Selection of Metalloenzymes by Catalytic Activity Using Phage Display and Catalytic Elution," Chembiochem. 2(4):253-259.
Prabakaran, S. et al. (2012). "Post-Translational Modification: Nature's Escape From Genetic Imprisonment and the Basis for Dynamic Information Encoding," Wiley Interdiscip Rev Syst Biol Med 4(6):565-583.
Rauth, S. et al. (2016). "High-Affinity Anticalins With Aggregation-Blocking Activity Directed Against the Alzheimer Beta-Amyloid Peptide," Biochem J 473(11):1563-1578.
Ray, A. et al. (2000). "Peptide Nucleic Acid (PNA): Its Medical and Biotechnical Applications and Promise for the Future," FASEB J 14(9):1041-1060.
Riley, N.M. et al. (2016). "Proteomics Moves Into the Fast Lane," Cell Svst 2(3):142-143.
Roloff, A. et al. (2013). "The Role of Reactivity in DNA Templated Native Chemical PNA Ligation During PCR," Bioorg Med Chem 21(12):3458-3464.
Roloff, A. et al. (2014). "DNA-Templated Native Chemical Ligation of Functionalized Peptide Nucleic Acids: A Versatile Tool for Single Base-Specific Detection of Nucleic Acids," Methods Mol Biol 1050:131-141.
Rosen, C.B. et al. (2014). "Template-Directed Covalent Conjugation of DNA to Native Antibodies, Transferrin and Other Metal-Binding Proteins," Nature Chemistry 6:804-809.
Roy, R.K. et al. (2015). "Design and Synthesis of Digitally Encoded Polymers That Can Be Decoded and Erased," Nat. Commun. 6(7237):1 -8.
Ryckelynck, M. et al. (2015). "Using Droplet-Based Microfluidics to Improve the Catalytic Properties of RNA Under Multiple-Turnover Conditions," RNA 21(3):458-469.
Sakurai, K. et al. (2005). "DNA-Templated Functional Group Transformations Enable Sequence-Programmed Synthesis Using Small-Molecule Reagents," J Am Chem Soc 127(6): 1660-1661.
Schneider, K. et al. (1995). "Increased Stability of Nucleic Acids Containing 7-Deaza-Guanosine and 7-Deaza-Adenosine May Enable Rapid DNA Sequencing by Matrix-Assisted Laser Desorption Mass Spectrometry," Nucleic Acids Res 23(9): 1570-1575.
Schutze, T. et al. (2011). "A Streamlined Protocol for Emulsion Polymerase Chain Reaction and Subsequent Purification," Anal Biochem. 410(1):155-157.
Selvaraj, R. et al. (2013). "Trans-Cyclooctene—A Stable, Voracious Dienophile for Bioorthogonal Labeling," Curr Opin Chem Biol 17(5): 753-760.
Seo, J. et al. (Jan. 2004). "Post-Translational Modifications and Their Biological Functions: Proteomic Analysis and Systematic Approaches," Biochemistry and Molecular Biology 37(1):35-44.
Service, R.F. (2006). "Gene Sequencing. The Race for the $1000 Genome," Science 311(5767):1544-1546.
Shagin, D.A. et al. (2002). "A Novel Method for SNP Detection Using a New Duplex-Specific Nuclease From Crab Hepatopancreas," Genome Res. 12:1935-1942.
Sharma, A.K. et al. (2012), "Enzyme-Linked Small-Molecule Detection Using Split Aptamer Ligation," Anal Chem 84(14): 6104-6109.
Shembekar, N. et al. (2016). "Droplet-Based Microfluidics in Drug Discovery, Transcriptomics and High-Throughput Molecular Genetics," Lab Chip 16(8): 1314-1331.
Shenoy, N.R. et al. (1993). "Studies in C-Terminal Sequencing: New Reagents for the Synthesis of Peptidylthiohydantoins," J Protein Chem 12(2): 195-205.
Shim, J. U. et al. (2013). "Ultrarapid Generation of Femtoliter Microfiuidic Droplets for Single-Molecule-Counting Immunoassays," ACS Nano 7(7): 5955-5964.
Shim, J.W. et al. (2009), "Single-Molecule Detection of Folding and Unfolding of the G-Quadruplex Aptamer in a Nanopore Nanocavity," Nucleic Acids Res 37(3): 972-982.
Shuman, S. (1994). "Novel Approach to Molecular Cloning and Polynucleotide Synthesis Using Vaccinia DNA Topoisomerase," J. Biol. Chem. 269(51):32678-32684.
Sidoli, S. et al. (2015). "Drawbacks in the Use of Unconventional Hydrophobic Anhydrides for Histone Derivatization in Bottom-Up Proteomics PTM Analysis," Proteomics 15(9): 1459-1469, 18 pages.
Skerra, A. (2008). "Alternative Binding Proteins: Anticalins—Harnessing the Structural Plasticity of the Lipocalin Ligand Pocket to Engineer Novel Binding Activities," FEBS J. 275(11):2677-2683.
Sletten, E.M. et al. (2009). "Bioorthogonal Chemistry: Fishing for Selectivity in a Sea of Functionality," Angew Chem Int Ed Engl 48(38): 6974-6998.
Smith, E. et al. (2015). "Photoaffinity Labeling in Target and Binding-Site Identification," Future Med Chem. 7(2):159-183.
Soellner, M.B. et al. (Oct. 1, 2003). "Site-Specific Protein Immobilization by Staudinger Ligation," J. Am. Chem. Soc. 125(39):11790-11791.
Spencer, S.J. et al. (Feb. 2016). "Massively Parallel Sequencing of Single Cells by Epicpcr Links Functional Genes With Phylogenetic Markers," ISME J 10(2):427-436.
Spicer, C.D. et al. (Sep. 5, 2014). "Selective Chemical Protein Modification," Nat Commun 5:4740, 1-14 pages.
Spiropulos, N.G. et al. (Jul. 1, 2012). "Templating Effect in DNA Proximity Ligation Enables Use of Non-Bioorthogonal Chemistry in Biological Fluids," Artif DNA PNA XNA 3(3):123-128.
Spungin, A. et al. (1989)."*Streptomyces griseus* Aminopeptidase is a Calcium-Activated Zinc Metalloprotein Purification and Properties of the Enzyme," Eur. J. Biochem. 183(2):471-477.
Stahl, P.L. et al. (Jul. 1, 2016). "Visualization and Analysis of Gene Expression in Tissue Sections by Spatial Transcriptomics," Science 353(6294):78-82.
Stavis, C. et al. (Jan. 18, 2011, e-pub. Sep. 30, 2010). "Surface Functionalization of Thin-Film Diamond for Highly Stable and Selective Biological Interfaces," Proc. Natl. Acad. Sci. USA 108(3):983-988.
Steinberg, G. et al. (Apr. 5, 2004). "Strategies for Covalent Attachment of DNA to Beads," Biopolymers 73(5):597-605.
Sun, X-L. et al. (Jan./Feb. 2006). "Carbohydrate and Protein Immobilization Onto Solid Surfaces by Sequential Diels-Alder and Azide-Alkyne Cycloadditions," Bioconjug. Chem. 17(1):52-57.
Swaminathan, J. et al., (Feb. 25, 2015, e-pub, Feb. 2015) "A Theoretical Justification for Single Molecule Peptide Sequencing," Plos Comput. Biol. 11(2):E1004080, 17 pages.
Switzar, L. et al. (Mar. 1, 2013, e-pub. Feb. 13, 2015). "Protein Digestion: An Overview of the Available Techniques and Recent Developments," J Proteome Res 12(3):1067-1077.

(56) References Cited

OTHER PUBLICATIONS

Tamminen, M.V. et al. (Mar. 11, 2015). "Single Gene-Based Distinction of Individual Microbial Genomes From a Mixed Population of Microbial Cells," Front Microbiol 6:195, 1-10 pages.
Tessler, L. (Jan. 1, 2011). "Digital Protein Analysis: Technologies for Protein Diagnostics and Proteomics Through Single-Molecule Detection." Washington University in St. Louis 147 Pages.
Tse, B.N. et al. (Nov. 19, 2008). "Translation of DNA Into a Library of 13,000 Synthetic Small-Molecule Macrocycles Suitable for In Vitro Selection," J Am Chem Soc. 130(46):15611-15626.
Tullman, J. et al. (Sep. 2020, e-pub. Jul. 2, 2020). "Leveraging Nature's Biomolecular Designs in Next-Generation Protein Sequencing Reagent Development," Applied Microbiology and Biotechnology 104(17):7261-7271.
Turner, D.J. et al. (2009), "High-Throughput Haplotype Determination Over Long Distances by Haplotype Fusion PCR and Ligation Haplotyping," Nat. Protoc. 4(12):1771-1783.
Tyson, J. et al. (Dec. 11, 2012). "Determination of Haplotypes at Structurally Complex Regions Using Emulsion Haplotype Fusion PCR," BMC Genomics 13:693, 1-12 pages.
Vandernoot, V.A. et al. (Dec. 2012). "cDNA Normalization by Hydroxyapatite Chromatography to Enrich Transcriptome Diversity in RNA-seq Applications," Biotechniques 53(6):373-380.
Varland, S. et al. (Jul. 2015, e-pub. Jun. 16, 2015). "N-Terminal Modifications of Cellular Proteins: The Enzymes Involved, Their Substrate Specificities and Biological Effects," Proteomics 15(14):2385-2401.
Vauquelin, G. et al. (Apr. 2013). "Exploring Avidity: Understanding the Potential Gains in Functional Affinity and Target Residence Time of Bivalent and Heterobivalent Ligands," Br J Pharmacol 168(8):1771-1785.
Veggiani, G. et al. (Feb. 2, 2016, e-pub. Jan. 19, 2016). "Programmable polyproteams built using twin peptide superglues," Proc Natl Acad Sci USA 113(5):1202-1207.
Vitak, S.A. et al. (Mar. 2017, e-pub. Jan. 30, 2017). "Sequencing thousands of single-cell genomes with combinatorial indexing," Nat Methods 14(3):302-308.
Wagner, A.M. et al. (Sep. 28, 2011, e-pub. Sep. 6, 2011). "N-Terminal Protein Modification Using Simple Aminoacyl Transferase Substrates," J Am Chem Soc 133(38):15139-15147.
Wang, D. et al. (Mar. 1, 2009). "N-Terminal Derivatization of Peptides With Isothiocyanate Analogues Promoting Edman-Type Cleavage and Enhancing Sensitivity in Electrospray Ionization Tandem Mass Spectrometry Analysis," Anal Chem 81(5):1893-1900.
Wang, K.H. et al. (Nov. 7, 2008). "The Molecular Basis of N-End Rule Recognition," Mol Cell 32(3):406-414.
Warren, W.C. et al. (Oct. 3, 1996). "Increased Production of Peptide Deformylase Eliminates Retention of Formylmethionine in Bovine Somatotropin Overproduced in *Escherichia coli*," Gene 174(2):235-238.
Watzke, A. et al. (Feb. 20, 2006). "Site-Selective Protein Immobilization by Staudinger Ligation," Angew Chem. Int. Ed. Engl 45(9):1408-1412.
Whiteaker, J.R. et al. (Mar. 1, 2007, e-pub. Dec. 20, 2006). "Antibody-Based Enrichment of Peptides on Magnetic Beads for Mass-Spectrometry-Based Quantification of Serum Biomarkers," Anal. Biochem 362(1):44-54.
Wilce, M.C. et al. (Mar. 31, 1998). "Structure and Mechanism of a Proline-Specific Aminopeptidase From *Escherichia coli*," Proc. Natl. Acad. Sci. USA 95(7):3472-3477.

Williams, B.A.R. et al. (Sep. 2010). "Synthesis of Peptide-Oligonucleotide Conjugates Using a Heterobifunctional Crosslinker," Curr Protoc Nucleic Acid Chem Chapter 4:Unit 4.41, 1-29 pages.
Williams, R. et al. (Jul. 2006). "Amplification of Complex Gene Libraries by Emulsion PCR," Nat Methods 3(7):545-550.
Written Opinion of the International Searching Authority for International Application PCT/US2018/058565, dated Jan. 29, 2019, filed Oct. 31, 2018, 25 pages.
Written Opinion of the International Searching Authority for International Application PCT/US2018/058575, dated Apr. 15, 2019, filed Oct. 31, 2018, 7 Pages.
Written Opinion of the International Searching Authority for International Application PCT/US2018/058583, dated Jan. 22, 2019, filed Oct. 31, 2018, 8 Pages.
Written Opinion of the International Searching Authority for International Patent Application PCT/US2017/30702, dated Sep. 8, 2017, filed May 2, 2017, 11 Pages.
Wu, H. et al. (Feb. 2016, e-pub. Dec. 22, 2015). "Inverse Electron-Demand Diels-Alder Bioorthogonal Reactions," Top Curr Chem 374(1):3, 1-22 pages.
Xiao, W. et al. (Jul. 2013). "Immobilized OBOC Combinatorial Bead Array to Facilitate Multiplicative Screening," Combinatorial Chemistry & High Throughput Screening 16(6):441-448.
Xiong, A-S. et al. (May 2008, e-pub. Apr. 2, 2008). "Chemical Gene Synthesis: Strategies, Softwares, Error Corrections, and Applications," FEMS Microbiol Rev 32(3):522-540.
Xu, B. et al. (Dec. 27, 2013). "Protein Complex Identification by Integrating Protein-Protein Interaction Evidence From Multiple Sources," Plos One 8(12):E83841, 1-12 pages.
Yang, S-W. et al. (Oct. 1, 2002). "Mutant Thermotoga Neapolitana DNA Polymerase I: Altered Catalytic Properties for Non-Templated Nucleotide Addition and incorporation of Correct Nucleotides," Nucleic Acids Res 30(19):4314-4320.
Yao, Y. et al. (Aug. 12, 2015). "Single-Molecule Protein Sequencing Through Fingerprinting: Computational Assessment," Phys Biol 12(5):055003, 7 pages.
Yazdi, S.M.H.T. et al. (2015). "A Rewritable, Random-Access DNA-Based Storage System," Sci Rep 5:14138, 1-10 pages.
Yazdi, S.M.H.T. et al. (Sep. 2015). "DNA-Based Storage: Trends and Methods," IEEE Transactions on Molecular, Biological and Muiti-Scale Communications 1(3):230-248.
Yoo, C. et al. (Oct. 8, 2010, e-pub. Sep. 7, 2010). "An Aminopeptidase From *Streptomyces* Sp. KK565 Degrades Beta Amyloid Monomers, Oligomers and Fibrils," FEBS Lett. 584(19):4157-4162.
Young, D.D. et al. (Jan. 28, 2008, e-pub. Nov. 14, 2007). "Light-Triggered Polymerase Chain Reaction," Chem Commun (Camb) (4):462-464.
Yuan, L. et al. (Sep. 2005). "Laboratory-Directed Protein Evolution," Microbiol. Mol. Biol. Rev. 69(3):373-392.
Zakeri, B. et al. (Mar. 20, 2012, e-pub. Feb. 24, 2012). "Peptide Tag Forming a Rapid Covalent Bond to a Protein, Through Engineering a Bacterial Adhesin," PNAS USA 109(12):E690-E697.
Zhang, L. et al. (2016, e-pub. Feb. 26, 2016). "The Use of Lectin Microarray for Assessing Glycosylation of Therapeutic Proteins," mAbs 8(3):524-535.
Zhang, L. et al. (Apr. 19, 2016, e-pub, Apr. 6, 2016). "Single-Molecule Analysis of Human Telomere Sequence Interactions With G-Quadruplex Ligand," Anal Chem 88(8):4533-4540.
Zhou, H. et al. (Jan. 17, 2012, e-pub. Nov. 15, 2011), "Advancements in Top-Down Proteomics," Anal Chem 84(2):720-734.
Zilionis, R. et al. (Jan. 2017, e-pub. Dec. 8, 2016). "Single-Cell Barcoding and Sequencing Using Droplet Microfluidics," Nat Protoc 12(1):44-73.

\* cited by examiner

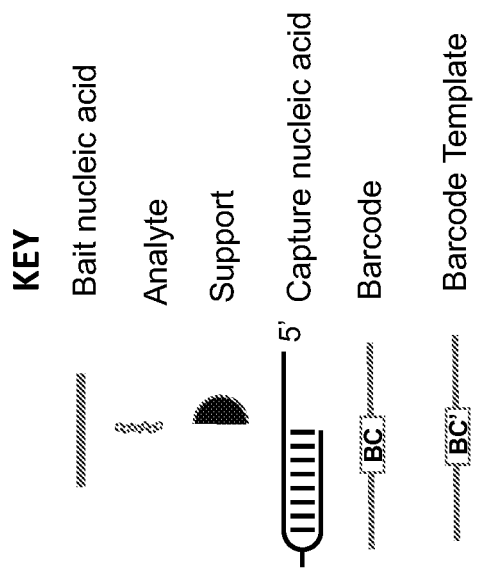
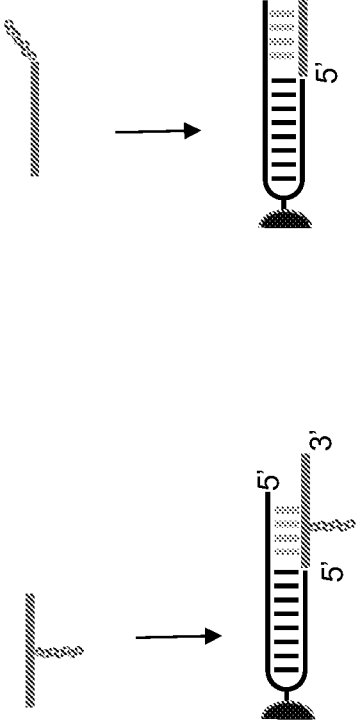
FIG. 1A
FIG. 1B
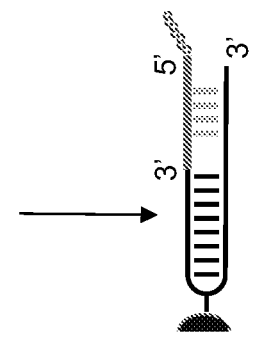
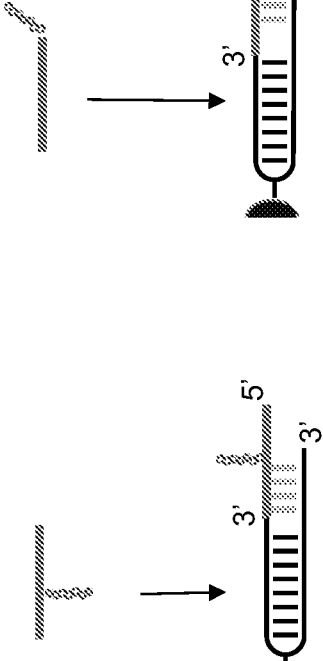
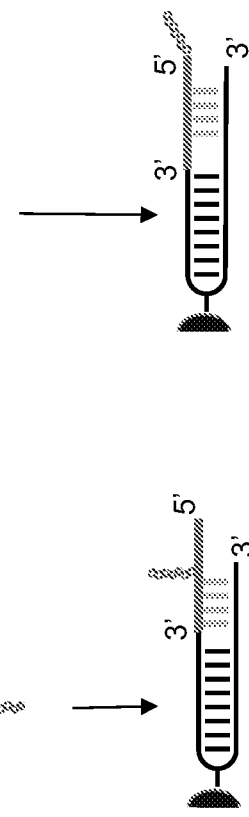
FIG. 1C
FIG. 1D

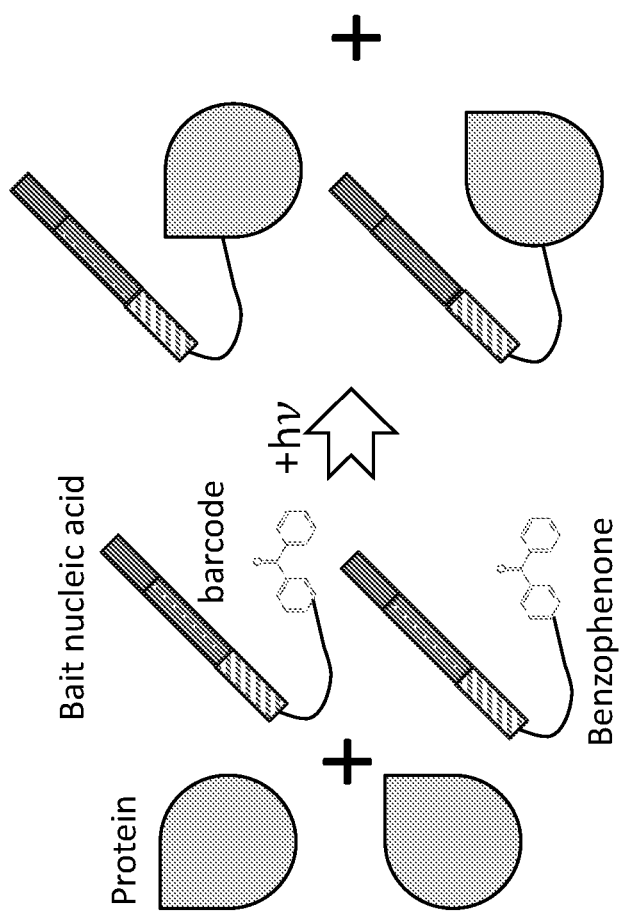
FIG. 2A Photoaffinity Label
FIG. 2B Hybridize
FIG. 2C Psoralen Cross-link

METHODS FOR PREPARING ANALYTES AND RELATED KITS

RELATED APPLICATION

The present application is a continuation application of International Patent Application Serial No. PCT/US2020/027840, filed on Apr. 10, 2020, entitled "METHODS FOR PREPARING ANALYTES AND RELATED KITS," which claims priority to U.S. provisional patent application Nos. 62/840,675, filed on Apr. 30, 2019, the disclosures and contents of which are incorporated by reference in their entireties for all purposes.

STATEMENT REGARDING FEDERALLY SPONSORED RESEARCH

This invention was made with government support awarded by the National Cancer Institute of the National Institutes of Health under Grant No. R44CA203629. The United States Government has certain rights in this invention pursuant to this grant.

SEQUENCE LISTING ON ASCII TEXT

This patent application file contains a Sequence Listing submitted in computer readable ASCII text format (file name: 4614-2001530_20210810_SeqList_ST25.txt, recorded: Aug. 10, 2021, size: 15,546 bytes). The content of the Sequence Listing file is incorporated herein by reference in its entirety.

TECHNICAL FIELD

The present disclosure relates to methods for preparing and treating an analyte (e.g., a macromolecule or a plurality of macromolecules, peptides, polypeptides, and proteins) for analysis. In some embodiments, the analyte is prepared and treated in a method that uses bait and capture nucleic acids, solid supports, and reaction mixtures including the bait and capture nucleic acids. In some embodiments, the analyte is coupled to a solid support. Also provided are kits containing components for performing the provided methods for preparing the analytes. In some embodiments, the methods and kits are for preparing an analyte for sequencing.

BACKGROUND

The present disclosure pertains to methods of preparing and treating analytes for assessment, for example preparing proteins for analysis (e.g., sequencing). From existing methodologies, DNA-directed immobilization of DNA-protein conjugates have been used to immobilize antibodies (Kim et al., Sensors (Basel) (2008) 8(10):6605-6641; Dahotre et al., PNAS (2018) 115(17):4357-4362; Jung et al., Anal. Chem (2007) 79(17):6534-6541). Other hybridization methods include using nucleic acids as probes to hybridize and detect target nucleic acids (U.S. Pat. No. 5,770,365).

However, methods for efficiently preparing analytes are needed to generate nucleic-acid analyte conjugate formats compatible with protein analysis (e.g., protein sequencing). For example, desirable methods of preparing analytes may be compatible with a degradation-based polypeptide sequencing assay. Furthermore, it may be advantageous for the analyte to be immobilized on the solid support such that the components remain attached and available for use in protein analysis assays that involve various chemical and/or enzymatic reactions. In some embodiments, the assay may involve multiple cycles and treatments with chemical reagents and/or enzymes. In some cases, the analyte and nucleic acid is prepared such that the nucleic acid components are available for use in a nucleic acid-based assay.

Accordingly, there remains a need for improved or new techniques relating to preparing analytes for analysis and/or sequencing, with applications to protein sequencing and/or analysis, as well as to products, methods and kits for accomplishing the same. There is a need for efficient methods to capture analytes in a format which allows for analyte assessment, e.g., nucleic acid-based assays. The present disclosure fulfills these and other related needs.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

Provided herein is a method for treating an analyte including attaching an analyte to a bait nucleic acid to generate a nucleic acid-analyte chimera; bringing the nucleic acid-analyte chimera into proximity with a solid support by hybridizing the bait nucleic acid in the nucleic acid-analyte chimera to a capture nucleic acid attached to the solid support; and covalently coupling the nucleic acid-analyte chimera to the solid support; wherein a plurality of the nucleic acid-analyte chimeras is coupled on the solid support and any adjacently coupled nucleic acid-analyte chimeras are spaced apart from each other at an average distance of about 50 nm or greater.

Provided herein is nucleic acid-analyte conjugate generated by attaching an analyte to a bait nucleic acid to generate a nucleic acid-analyte chimera; bringing the nucleic acid-analyte chimera into proximity with a solid support by hybridizing the bait nucleic acid in the nucleic acid-analyte chimera to a capture nucleic acid attached to the solid support; and covalently coupling the nucleic acid-analyte chimera to the solid support; wherein a plurality of nucleic acid-analyte chimeras is coupled on the solid support and any adjacently coupled nucleic acid-analyte chimeras are spaced apart at an average distance of about 50 nm or greater.

Provided herein are kits containing a plurality of bait nucleic acids, each of said bait nucleic acids is configured to be attached to an analyte; and a solid support comprising a plurality of attached capture nucleic acids, each of said capture nucleic acids comprising a sequence complementary to a corresponding bait nucleic acid, wherein any adjacently attached capture nucleic acids are spaced apart on the solid support at an average distance of about 50 nm or greater.

BRIEF DESCRIPTION OF THE DRAWINGS

Non-limiting embodiments of the present invention will be described by way of example with reference to the accompanying figures, which are schematic and are not intended to be drawn to scale. For purposes of illustration, not every component is labeled in every figure, nor is every component of each embodiment of the invention shown where illustration is not necessary to allow those of ordinary skill in the art to understand the invention.

FIG. 1A-1D depicts exemplary methods for attaching analytes to a bait nucleic acids and coupling the nucleic acid-analyte chimera to beads. In some examples, the analyte is attached directly or indirectly (e.g., via linkers) to the bait nucleic acid. In FIG. 1A, the analyte is attached to an internal position of the bait nucleic acid and the nucleic acid-analyte chimera is attached to the 3' end of the capture nucleic acid. In FIG. 1B, the analyte is attached to the 3' end of the bait nucleic acid and the nucleic acid-analyte chimera is attached to the 3' end of the capture nucleic acid. In FIG. 1C, the analyte is attached to an internal position of the bait nucleic acid and the nucleic acid-analyte chimera is attached to the 5' end of the capture nucleic acid. In FIG. 1D, the analyte is attached to the 5' end of the bait nucleic acid and the nucleic acid-analyte chimera is attached to the 5' end of the capture nucleic acid. In some embodiments, the attachment of the bait nucleic acid to the capture nucleic acid is by ligation.

FIG. 2A-C depicts a method for photoaffinity labeling and immobilization of protein analytes. Bait nucleic acids with a photoactive benzophenone moiety are used to randomly label proteins upon exposure to UV365 nm light, thereby forming nucleic acid-analyte chimeras (FIG. 2A). This process could also be done in a two-step procedure using an alkyne-benzophenone and azide-oligo. The nucleic acid-analyte chimeras are hybridized via their bait nucleic acid to a surface derivatized with complementary capture nucleic acids that have a reactive psoralen moiety (FIG. 2B). The complexes are covalently cross-linked with psoralen upon exposure to UV light (FIG. 2C).

FIG. 3 depicts the following steps for immobilizing the analyte: a barcode template (BC') hybridizes to the nucleic acid-analyte chimera; an extension reaction is used to extend the 3' end of the bait nucleic acid to include the barcode sequence; the nucleic acid-analyte chimera with the newly extended barcode is brought into proximity with a solid support by hybridizing the bait nucleic acid (with the analyte and barcode) to a capture nucleic acid attached to the solid support; the nucleic acid-analyte chimera is covalently coupled to the solid support by attaching (e.g., via ligation) the capture nucleic acid and the bait nucleic acid.

FIG. 4 depicts the following steps for immobilizing the analyte: the nucleic acid-analyte chimera is brought into proximity with a solid support by hybridizing the bait nucleic acid (with the analyte) to a capture nucleic acid attached to the solid support; the nucleic acid-analyte chimera is covalently coupled to the solid support by attaching (e.g., via ligation) the capture nucleic acid and the bait nucleic acid; a barcode template (BC') is used to perform an extension reaction to extend the 3' end of the bait nucleic acid to include the barcode sequence from the template; a digestion reaction is used to release the barcode template from the nucleic-acid analyte conjugate coupled on the solid support.

FIG. 5 depicts the following steps for immobilizing the analyte: a ligation reaction is used to attach the bait nucleic acid to the barcode; the nucleic acid-analyte chimera with the attached barcode is brought into proximity with a solid support by hybridizing the bait nucleic acid (with the analyte and barcode) to a capture nucleic acid attached to the solid support; the nucleic acid-analyte chimera is covalently coupled to the solid support by attaching (e.g., via ligation) the capture nucleic acid and the bait nucleic acid. In some embodiments, a splinted nucleic acid strand is used, wherein the splint bridges the bait nucleic acid and barcode via hybridization and enables efficient ligation or chemical coupling. In some embodiments, the splinted nucleic acid is separate from the bait nucleic acid.

FIGS. 6 and 7 depicts the attachment of a barcode to the 3' end of the capture nucleic acid (e.g., via ligation) and coupling of a nucleic acid-analyte chimera to the solid support by attaching (e.g., via ligation) the bait nucleic acid to the 5' capture nucleic acid. In FIG. 6, a barcode hybridizes to a region of the nucleic acid-analyte chimera and both are brought into proximity with a solid support by hybridizing the bait nucleic acid of the chimera to a capture nucleic acid attached to the solid support; the nucleic acid-analyte chimera is covalently coupled to the solid support by attaching (e.g., via ligation) the 5' end of the capture nucleic acid to the bait nucleic acid; the barcode is attached to the 3' end of the capture nucleic acid (e.g., via ligation). In FIG. 7, the nucleic acid-analyte chimera is brought into proximity with a solid support by hybridizing the bait nucleic acid of the chimera to the 5' end of a capture nucleic acid that is attached to the solid support and the capture nucleic acid includes a barcode sequence.

DETAILED DESCRIPTION

Figures 3, 4, 5:
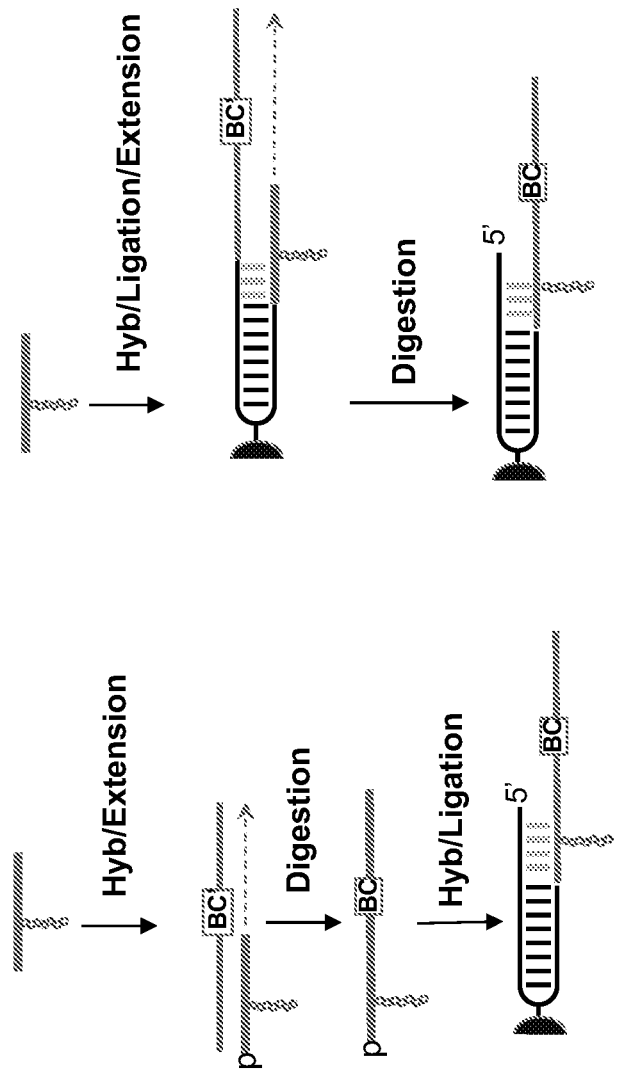
FIG. 3-7 depicts exemplary steps and configurations for forming a nucleic acid-analyte conjugate on a solid support including optionally adding a barcode sequence. In some cases, the barcode sequence may include a sample barcode, a fraction barcode, spatial barcode, a compartment tag, or any combinations thereof. Using similar methods, a UMI or other functional nucleic acid components can be added, e.g., a universal priming site, a spacer sequence that is complementary to a spacer sequence attached to another nucleic acid moiety, or any combinations thereof.

Provided herein are methods and kits for preparing an analyte (e.g., a macromolecule or a plurality of macromolecules, peptides, polypeptides, and proteins). In some embodiments, the methods and kits are for treating the analytes in preparation for sequencing and/or analysis. In some embodiments, the methods include attaching the analyte to a solid support. In some embodiments, the immobilized nucleic acid-analyte chimera is configured for analysis of the analyte, e.g., wherein the analysis employs barcoding and nucleic acid encoding of molecular recognition events, and/or detectable labels. In some embodiments, the methods include attaching an analyte to a bait nucleic acid to generate a nucleic acid-analyte chimera; bringing the nucleic acid-analyte chimera into proximity with a solid support by hybridizing the bait nucleic acid in the nucleic acid-analyte chimera to a capture nucleic acid attached to the solid support; and covalently coupling the nucleic acid-analyte chimera to the solid support, wherein a plurality of the nucleic acid-analyte chimeras is coupled on the solid support and any adjacently coupled nucleic acid-analyte chimeras are spaced apart from each other at an average distance of 50 nm or greater. In some embodiments, the analytes are obtained from a biological sample. In some cases, the analyte is a protein. In some embodiments, the analyte is a peptide, e.g., peptides generated from the fragmenting proteins obtained from a sample. Also provided are nucleic acid-analyte conjugates generated by any of the methods provided herein.

Also provided are kits containing components and/or reagents for performing the provided methods for treating and preparing analytes for sequencing and/or analysis. In some embodiments, the kits also include instructions for using the kit to perform any of the methods for preparing or treating analytes provided herein.

Existing methodologies for immobilizing and capturing analytes include DNA-directed immobilization of DNA-protein conjugates, including for immobilizing antibodies on solid surfaces (Kim et al., Sensors (Basel). (2008) 8(10): 6605-6641; Dahotre et al., PNAS (2018) 115(17):4357-4362; Jung et al., Anal. Chem (2007) 79(17):6534-6541). Other known hybridization methods include using nucleic acids as probes to hybridize and detect target nucleic acids (U.S. Pat. No. 5,770,365).

However, methods for efficiently preparing analytes are needed to generate nucleic-acid analyte conjugate formats that is compatible with protein analysis (e.g., protein sequencing). For example, it may be advantageous for the analyte to be immobilized on the solid support such that the analyte and nucleic acid components remain attached and/or immobilized throughout protein analysis assays that involve various chemical and/or enzymatic reactions. In some embodiments, the assay may involve multiple cycles and treatments with chemical reagents and/or enzymes. In some cases, the analyte and/or nucleic acid are coupled to a solid support such that both are and remain available during a protein analysis assay, including through multiple cycles of an assay. In some cases, the analyte and nucleic acid is prepared such that the nucleic acid components are available for use in a nucleic acid-based analyte assay. For example, the nucleic acids used may include components used in downstream analysis, such as components useful for downstream DNA sequencing.

Accordingly, there remains a need for improved techniques relating to preparing analytes for analysis and/or sequencing, with applications to protein sequencing and/or analysis, as well as to products, methods and kits for accomplishing the same. There is a need for efficient methods to capture analytes in a format which allows for analyte assessment, e.g., using nucleic acid-based assays. The present disclosure fulfills these and other related needs. In some embodiments, the present disclosure provides, in part, methods for preparing analytes to use with methods of highly-parallel, high throughput digital macromolecule (e.g., polypeptide) characterization and quantitation, with direct applications to protein and peptide characterization and sequencing.

In some embodiments, provided herein are methods for treating analytes including attaching an analyte to a bait nucleic acid to generate a nucleic acid-analyte chimera; bringing the nucleic acid-analyte chimera into proximity with a solid support by hybridizing the bait nucleic acid in the nucleic acid-analyte chimera to a capture nucleic acid attached to the solid support; and covalently coupling the nucleic acid-analyte chimera to the solid support; wherein a plurality of the nucleic acid-analyte chimeras is coupled on the solid support and any adjacently coupled nucleic acid-analyte chimeras are spaced apart from each other at an average distance of about 50 nm or greater. Also provided are nucleic-acid analyte conjugates generated by attaching an analyte to a bait nucleic acid to generate a nucleic acid-analyte chimera; bringing the nucleic acid-analyte chimera into proximity with a solid support by hybridizing the bait nucleic acid in the nucleic acid-analyte chimera to a capture nucleic acid attached to the solid support; and covalently coupling the nucleic acid-analyte chimera to the solid support; wherein a plurality of the nucleic acid-analyte chimeras is coupled on the solid support spaced apart and any adjacently coupled nucleic acid-analyte chimeras are spaced apart from each other at an average distance of 50 nm or greater. In some embodiments, the analyte comprises a plurality of macromolecules, e.g., proteins, polypeptides, peptides, or fragments thereof, obtained from a sample. In some embodiments, the sample is obtained from a subject. In some embodiments, the analytes are directly or indirectly coupled to the bait nucleic acid. In some embodiments, the analytes are directly or indirectly coupled to the solid support.

In some embodiments, the analyte is attached to the 3' end of the bait nucleic acid. In some embodiments, the analyte is attached to the 5' end of the bait nucleic acid. In some embodiments, the analyte is attached to an internal position of the bait nucleic acid. In some aspects, the capture nucleic acid, the nucleic acid-analyte chimera, and/or the bait nucleic acid further comprises a barcode. In some cases, the method for preparing and treating the analyte further comprises attaching a barcode to the nucleic acid-analyte chimera after it is coupled to the solid support. In some examples, the barcode comprises a compartment barcode, a partition barcode, a sample barcode, a fraction barcode, or any combination thereof.

In some embodiments, the nucleic acid-analyte conjugate is compatible for use with a nucleic acid-based analyte sequencing assay. In some embodiments, after conjugating the bait nucleic acid-analyte chimera to the solid support, the 5' end of the bait nucleic acid is available for reaction. In some embodiments, after conjugating the bait nucleic acid-analyte chimera to the solid support, the 5' end of the capture nucleic acid is available for reaction. In some embodiments, after conjugating the bait nucleic acid-analyte chimera to the solid support, the 3' end of the bait nucleic acid is available for reaction. In some embodiments, after conjugating the bait nucleic acid-analyte chimera to the solid support, the 3' end of the capture nucleic acid is available for reaction. In some examples, the nucleic acid is available for an extension reaction, e.g., a PCR extension reaction, and/or a ligation reaction.

In some embodiments, the method for treating the analytes described herein are compatible for analyzing the analyte using an assay which includes contacting the analyte with a binding agent capable of binding to the analyte, wherein the binding agent comprises a coding tag with identifying information regarding the binding agent; and transferring the identifying information of the coding tag to the bait nucleic acid or capture nucleic acid. In some examples, the nucleic acid-analyte conjugate on the solid support is generated such that after coupling, both the nucleic acid and analyte are available for use in an assay which includes contacting the analyte with a binding agent capable of binding to the analyte, wherein the binding agent comprises a coding tag with identifying information regarding the binding agent; and transferring the identifying information of the coding tag to the bait nucleic acid or capture nucleic acid. In some examples, the nucleic acid-analyte conjugate on the solid support is compatible for use with a sequencing assay which include one or more cycles of contacting with a binding agent and transferring identifying information.

Provided herein is a kit, comprising (a) a plurality of bait nucleic acids, each of said bait nucleic acids is configured to be attached to an analyte; and (b) a solid support comprising a plurality of attached capture nucleic acids, each of said capture nucleic acids comprising a sequence complementary to a corresponding bait nucleic acid, wherein any adjacently attached capture nucleic acids are spaced apart on the solid support at an average distance of about 50 nm or greater. In some embodiments, provided are kits comprising (a) a plurality of bait nucleic acids, each of said bait nucleic acids is configured to be attached to an analyte; and (b) a plurality of capture nucleic acids, each of said capture nucleic acids comprising a sequence complementary to a corresponding bait nucleic acid.

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

Definitions

Unless defined otherwise, all technical and scientific terms used herein have the same meaning as is commonly understood by one of ordinary skill in the art to which the present disclosure belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a," "an" and "the" include plural referents unless the context clearly dictates otherwise. Thus, for example, reference to "a peptide" includes one or more peptides, or mixtures of peptides. Reference to "an analyte" includes one or more analytes, or mixtures of analytes. Also, and unless specifically stated or obvious from context, as used herein, the term "or" is understood to be inclusive and covers both "or" and "and".

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X.

As used herein, the term "macromolecule" encompasses large molecules composed of smaller subunits. Examples of macromolecules include, but are not limited to peptides, polypeptides, proteins, nucleic acids, carbohydrates, lipids, macrocycles. A macromolecule also includes a chimeric macromolecule composed of a combination of two or more types of macromolecules, covalently linked together (e.g., a peptide linked to a nucleic acid). A macromolecule may also include a "macromolecule assembly", which is composed of non-covalent complexes of two or more macromolecules. A macromolecule assembly may be composed of the same type of macromolecule (e.g., protein-protein) or of two more different types of macromolecules (e.g., protein-DNA).

As used herein, the term "polypeptide" encompasses peptides and proteins, and refers to a molecule comprising a chain of two or more amino acids joined by peptide bonds. In some embodiments, a polypeptide comprises 2 to 50 amino acids, e.g., having more than 20-30 amino acids. In some embodiments, a peptide does not comprise a secondary, tertiary, or higher structure. In some embodiments, the polypeptide is a protein. In some embodiments, a protein comprises 30 or more amino acids, e.g. having more than 50 amino acids. In some embodiments, in addition to a primary structure, a protein comprises a secondary, tertiary, or higher structure. The amino acids of the polypeptides are most typically L-amino acids, but may also be D-amino acids, modified amino acids, amino acid analogs, amino acid mimetics, or any combination thereof. Polypeptides may be naturally occurring, synthetically produced, or recombinantly expressed. Polypeptides may be synthetically produced, isolated, recombinantly expressed, or be produced by a combination of methodologies as described above. Polypeptides may also comprise additional groups modifying the amino acid chain, for example, functional groups added via post-translational modification. The polymer may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, or any other manipulation or modification, such as conjugation with a labeling component.

As used herein, the term "amino acid" refers to an organic compound comprising an amine group, a carboxylic acid group, and a side-chain specific to each amino acid, which serve as a monomeric subunit of a peptide. An amino acid includes the 20 standard, naturally occurring or canonical amino acids as well as non-standard amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized. Examples of non-standard amino acids include, but are not limited to, selenocysteine, pyrrolysine, and N-formylmethionine, (3-amino acids, Homo-amino acids, Proline and Pyruvic acid derivatives, 3-substituted alanine derivatives, glycine derivatives, ring-substituted phenylalanine and tyrosine derivatives, linear core amino acids, N-methyl amino acids.

As used herein, the term "post-translational modification" refers to modifications that occur on a peptide after its translation by ribosomes is complete. A post-translational modification may be a covalent chemical modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini. The term post-translational modification can also include peptide modifications that include one or more detectable labels.

As used herein, the term "binding agent" refers to a nucleic acid molecule, a peptide, a polypeptide, a protein, carbohydrate, or a small molecule that binds to, associates, unites with, recognizes, or combines with an analyte, e.g., a polypeptide or a component or feature of a polypeptide. A binding agent may form a covalent association or non-covalent association with an analyte, e.g., the polypeptide or component or feature of a polypeptide. A binding agent may also be a chimeric binding agent, composed of two or more types of molecules, such as a nucleic acid molecule-peptide chimeric binding agent or a carbohydrate-peptide chimeric binding agent. A binding agent may be a naturally occurring, synthetically produced, or recombinantly expressed molecule. A binding agent may bind to a single monomer or subunit of a polypeptide (e.g., a single amino acid of a polypeptide) or bind to a plurality of linked subunits of a polypeptide (e.g., a di-peptide, tri-peptide, or higher order peptide of a longer peptide, polypeptide, or protein molecule). A binding agent may bind to a linear molecule or a molecule having a three-dimensional structure (also referred to as conformation). For example, an antibody binding agent may bind to linear peptide, polypeptide, or protein, or bind to a conformational peptide, polypeptide, or protein. A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may bind to an N-terminal or C-terminal diamino acid moiety. A binding agent may preferably bind to a chemically modified or labeled amino acid (e.g., an amino acid that has been functionalized by a reagent (e.g., a compound)) over a non-modified or unlabeled amino acid. For example, a binding agent may preferably bind to an amino acid that has been functionalized with an acetyl moiety, Cbz moiety, guanyl moiety, dansyl moiety, PTC moiety, DNP moiety, SNP moiety, diheterocyclic methanimine moiety, etc., over an amino acid that does not possess said moiety. A binding agent may bind to a post-translational modification of a peptide molecule. A binding agent may exhibit selective binding to a component or feature of a polypeptide (e.g., a binding agent may selectively bind to one of the 20 possible natural amino acid residues and with bind with very low affinity or not at all to the other 19 natural amino acid residues). A binding agent may exhibit less selective binding, where the binding agent is capable of binding a plurality of components or features of a polypeptide (e.g., a binding agent may bind with similar affinity to two or more different amino acid residues). A binding agent comprises or is attached to a coding tag, which may be joined to the binding agent by a linker.

As used herein, the term "linker" refers to one or more of a nucleotide, a nucleotide analog, an amino acid, a peptide, a polypeptide, or a non-nucleotide chemical moiety that is used to join two molecules. A linker may be used to join a binding agent with a coding tag, a bait nucleic acid with a polypeptide, a polypeptide with a solid support, a capture nucleic acid with a solid support, etc. In certain embodiments, a linker joins two molecules via enzymatic reaction or chemistry reaction (e.g., click chemistry).

As used herein, the term "proteome" can include the entire set of proteins, polypeptides, or peptides (including conjugates or complexes thereof) expressed by a genome, cell, tissue, or organism at a certain time, of any organism. In one aspect, it is the set of expressed proteins in a given type of cell or organism, at a given time, under defined conditions. Proteomics is the study of the proteome. For example, a "cellular proteome" may include the collection of proteins found in a particular cell type under a particular set of environmental conditions, such as exposure to hormone stimulation. An organism's complete proteome may include the complete set of proteins from all of the various cellular proteomes. A proteome may also include the collection of proteins in certain sub-cellular biological systems. For example, all of the proteins in a virus can be called a viral proteome. As used herein, the term "proteome" include subsets of a proteome, including but not limited to a kinome; a secretome; a receptome (e.g., GPCRome); an immunoproteome; a nutriproteome; a proteome subset defined by a post-translational modification (e.g., phosphorylation, ubiquitination, methylation, acetylation, glycosylation, oxidation, lipidation, and/or nitrosylation), such as a phosphoproteome (e.g., phosphotyrosine-proteome, tyrosine-kinome, and tyrosine-phosphatome), a glycoproteome, etc.; a proteome subset associated with a tissue or organ, a developmental stage, or a physiological or pathological condition; a proteome subset associated a cellular process, such as cell cycle, differentiation (or de-differentiation), cell death, senescence, cell migration, transformation, or metastasis; or any combination thereof. As used herein, the term "proteomics" refers to analysis of the proteome within cells, tissues, and bodily fluids, and the corresponding spatial distribution of the proteome within the cell and within tissues. In some embodiments, analysis may include quantitative and/or qualitative analysis. Additionally, proteomics studies include the dynamic state of the proteome, continually changing in time as a function of biology and defined biological or chemical stimuli.

The terminal amino acid at one end of the peptide chain that has a free amino group is referred to herein as the "N-terminal amino acid" (NTAA). The terminal amino acid at the other end of the chain that has a free carboxyl group is referred to herein as the "C-terminal amino acid" (CTAA). An N-terminal diamino acid is comprised of the N-terminal amino acid and the penultimate N-terminal amino acid. A C-terminal diamino acid is similarly defined for the C-terminus. The amino acids making up a peptide may be numbered in order, with the peptide being "n" amino acids in length. As used herein, NTAA is considered the $n^{th}$ amino acid (also referred to herein as the "n NTAA"). Using this nomenclature, the next amino acid is the n-1 amino acid, then the n-2 amino acid, and so on down the length of the peptide from the N-terminal end to C-terminal end. In certain embodiments, an NTAA, CTAA, or both may be functionalized with a chemical moiety.

As used herein, the term "barcode" refers to a nucleic acid molecule of about 2 to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) providing a unique identifier tag or origin information for a polypeptide, a binding agent, a set of binding agents from a binding cycle, a sample polypeptides, a set of samples, polypeptides within a compartment (e.g., droplet, bead, or separated location), polypeptides within a set of compartments, a fraction of polypeptides, a set of polypeptide fractions, a spatial region or set of spatial regions, a library of polypeptides, or a library of binding agents. A barcode can be an artificial sequence or a naturally occurring sequence. In certain embodiments, each barcode within a population of barcodes is different. In other embodiments, a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. In certain embodiments, a population of barcodes are error correcting barcodes. Barcodes can be used to in analysis and identify sequence reads derived from an individual polypeptide, sample, library, etc. A barcode can also be used for deconvolution of a collection of polypeptides that have been distributed into small compartments for enhanced mapping. For example, rather than mapping a peptide back to the proteome, the peptide is mapped back to its originating protein molecule or protein complex. BC' refers to spacer sequence complementary to a barcode (BC).

A "sample barcode", also referred to as "sample tag" identifies from which sample a polypeptide derives.

A "spatial barcode" identifies which region of a 2-D or 3-D tissue section from which a polypeptide derives. Spatial barcodes may be used for molecular pathology on tissue sections. A spatial barcode allows for multiplex sequencing of a plurality of samples or libraries from tissue section(s).

As used herein the term "binding cycle specific tag", "binding cycle specific barcode", or "binding cycle specific sequence" refers to a unique sequence used to identify a library of binding agents used within a particular binding cycle. A binding cycle specific tag may comprise about 2 bases to about 8 bases (e.g., 2, 3, 4, 5, 6, 7, or 8 bases) in length. A binding cycle specific tag may be incorporated within a binding agent's coding tag as part of a spacer sequence, part of an encoder sequence, part of a UMI, or as a separate component within the coding tag.

As used herein, the term "spacer" (Sp) refers to a nucleic acid molecule of about 1 base to about 20 bases (e.g., 1, 2, 3, 4, 5, 6, 7, 8, 9, 10, 11, 12, 13, 14, 15, 16, 17, 18, 19, or 20 bases) in length that is present on a terminus of a nucleic acid (e.g., bait nucleic acid or capture nucleic acid) or coding tag. In certain embodiments, a spacer sequence flanks an encoder sequence of a coding tag on one end or both ends. Following binding of a binding agent to a polypeptide, annealing between the complementary spacer sequences on the coding tag and on the bait or capture nucleic acid, allows transfer of binding information through a primer extension reaction or ligation to the nucleic acid constructs (e.g., bait or capture nucleic acid). Sp' refers to spacer sequence complementary to Sp. Preferably, spacer sequences within a library of binding agents possess the same number of bases. A common (shared or identical) spacer may be used in a library of binding agents. A spacer sequence may have a "cycle specific" sequence in order to track binding agents used in a particular binding cycle. The spacer sequence (Sp) can be constant across all binding cycles, be specific for a particular class of polypeptides, or be binding cycle number specific. Polypeptide class-specific spacers permit annealing of a cognate binding agent's coding tag information present in an extended nucleic acid from a completed binding/ extension cycle to the coding tag of another binding agent recognizing the same class of polypeptides in a subsequent binding cycle via the class-specific spacers. Only the sequential binding of correct cognate pairs results in interacting spacer elements and effective primer extension. A spacer sequence may comprise sufficient number of bases to anneal to a complementary spacer sequence in a nucleic acid to which the identifying information from the coding tag is to be transferred to (e.g., on the bait or capture nucleic acid) to initiate a primer extension (also referred to as polymerase extension) reaction, or provide a "splint" for a ligation reaction, or mediate a "sticky end" ligation reaction. A spacer sequence may comprise a fewer number of bases than the encoder sequence within a coding tag.

As used herein, the term "primer extension", also referred to as "polymerase extension", refers to a reaction catalyzed by a nucleic acid polymerase (e.g., DNA polymerase) whereby a nucleic acid molecule (e.g., oligonucleotide primer, spacer sequence) that anneals to a complementary strand is extended by the polymerase, using the complementary strand as template.

As used herein, the term "unique molecular identifier" or "UMI" refers to a nucleic acid molecule of about 3 to about 40 bases (3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases in length providing a unique identifier tag for each polypeptide or binding agent to which the UMI is linked. A polypeptide UMI can be used to computationally deconvolute sequencing data from a plurality of extended nucleic acids to identify extended nucleic acids that originated from an individual polypeptide. A polypeptide UMI can be used to accurately count originating polypeptide molecules by collapsing NGS reads to unique UMIs. A binding agent UMI can be used to identify each individual molecular binding agent that binds to a particular polypeptide. For example, a UMI can be used to identify the number of individual binding events for a binding agent specific for a single amino acid that occurs for a particular peptide molecule. It is understood that when UMI and barcode are both referenced in the context of a binding agent or polypeptide, that the barcode refers to identifying information other that the UMI for the individual binding agent or polypeptide (e.g., sample barcode, compartment barcode, binding cycle barcode).

As used herein, the term "universal priming site" or "universal primer" or "universal priming sequence" refers to a nucleic acid molecule, which may be used for library amplification and/or for sequencing reactions. A universal priming site may include, but is not limited to, a priming site (primer sequence) for PCR amplification, flow cell adaptor sequences that anneal to complementary oligonucleotides on flow cell surfaces enabling bridge amplification in some next generation sequencing platforms, a sequencing priming site, or a combination thereof. Universal priming sites can be used for other types of amplification, including those commonly used in conjunction with next generation digital sequencing. For example, extended nucleic acid molecules may be circularized and a universal priming site used for rolling circle amplification to form DNA nanoballs that can be used as sequencing templates (Drmanac et al., 2009, Science 327:78-81). Alternatively, nucleic acid molecules may be circularized and sequenced directly by polymerase extension from universal priming sites (Korlach et al., 2008, Proc. Natl. Acad. Sci. 105:1176-1181). The term "forward" when used in context with a "universal priming site" or "universal primer" may also be referred to as "5'" or "sense". The term "reverse" when used in context with a "universal priming site" or "universal primer" may also be referred to as "3'" or "antisense".

As used herein, the term "solid support", "solid surface", or "solid substrate", or "sequencing substrate", or "substrate" refers to any solid material, including porous and non-porous materials, to which a polypeptide can be associated directly or indirectly, by any means known in the art, including covalent and non-covalent interactions, or any combination thereof. A solid support may be two-dimensional (e.g., planar surface) or three-dimensional (e.g., gel matrix or bead). A solid support can be any support surface including, but not limited to, a bead, a microbead, an array, a glass surface, a silicon surface, a plastic surface, a filter, a membrane, a PTFE membrane, a PTFE membrane, a nitrocellulose membrane, a nitrocellulose-based polymer surface, nylon, a silicon wafer chip, a flow through chip, a flow cell, a biochip including signal transducing electronics, a channel, a microtiter well, an ELISA plate, a spinning interferometry disc, a polymer matrix, a nanoparticle, or a microsphere. Materials for a solid support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, dextran, or any combination thereof. Solid supports further include thin film, membrane, bottles, dishes, fibers, woven fibers, shaped polymers such as tubes, particles, beads, microspheres, microparticles, or any combination thereof. For example, when solid surface is a bead, the bead can include, but is not limited to, a ceramic bead, a polystyrene bead, a polymer bead, a polyacrylate bead, a methylstyrene bead, an agarose bead, a cellulose bead, a dextran bead, an acrylamide bead, a solid core bead, a porous bead, a paramagnetic bead, a glass bead, or a controlled pore bead, a silica-based bead, or any combinations thereof. A bead may be spherical or an irregularly shaped. A bead or support may be porous. A bead's size may range from nanometers, e.g., 100 nm, to millimeters, e.g., 1 mm. In certain embodiments, beads range in size from about 0.2 micron to about 200 microns, or from about 0.5 micron to about 5 micron. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 μm in diameter. In certain embodiments, "a bead" solid support may refer to an individual bead or a plurality of beads. In some embodiments, the solid surface is a nanoparticle. In certain embodiments, the nanoparticles range in size from about 1 nm to about 500 nm in diameter, for example, between about 1 nm and about 20 nm, between about 1 nm and about 50 nm, between about 1 nm and about 100 nm, between about 10 nm and about 50 nm, between about 10 nm and about 100 nm, between about 10 nm and about 200 nm, between about 50 nm and about 100 nm, between about 50 nm and about 150, between about 50 nm and about 200 nm, between about 100 nm and about 200 nm, or between about 200 nm and about 500 nm in diameter. In some embodiments, the nanoparticles can be about 10 nm, about 50 nm, about 100 nm, about 150 nm, about 200 nm, about 300 nm, or about 500 nm in diameter. In some embodiments, the nanoparticles are less than about 200 nm in diameter.

As used herein, the term "nucleic acid", "nucleic acid molecule" or "polynucleotide" refers to a single- or double-stranded polynucleotide containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), γPNAs, morpholino polynucleotides, locked nucleic acids (LNAs), threose nucleic acid (TNA), 2'-O-Methyl polynucleotides, 2'-O- alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding. In some embodiments, the nucleic acid molecule or oligonucleotide is a modified oligonucleotide. In some embodiments, the nucleic acid molecule or oligonucleotide is a DNA with pseudo-complementary bases, a DNA with protected bases, an RNA molecule, a BNA molecule, an XNA molecule, a LNA molecule, a PNA molecule, a γPNA molecule, or a morpholino DNA, or a combination thereof. In some embodiments, the nucleic acid molecule or oligonucleotide is backbone modified, sugar modified, or nucleobase modified. In some embodiments, the nucleic acid molecule or oligonucleotide has nucleobase protecting groups such as Alloc, electrophilic protecting groups such as thiranes, acetyl protecting groups, nitrobenzyl protecting groups, sulfonate protecting groups, or traditional base-labile protecting groups.

As used herein, "nucleic acid sequencing" means the determination of the order of nucleotides in a nucleic acid molecule or a sample of nucleic acid molecules.

As used herein, "next generation sequencing" refers to high-throughput sequencing methods that allow the sequencing of millions to billions of molecules in parallel. Examples of next generation sequencing methods include sequencing by synthesis, sequencing by ligation, sequencing by hybridization, polony sequencing, ion semiconductor sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, Thermo-Fisher, and Roche, including formats such as parallel bead arrays, sequencing by synthesis, sequencing by ligation, capillary electrophoresis, electronic microchips, "biochips," microarrays, parallel microchips, and single-molecule arrays, as reviewed by Service (*Science* 311:1544-1546, 2006).

As used herein, "single molecule sequencing" or "third generation sequencing" refers to next-generation sequencing methods wherein reads from single molecule sequencing instruments are generated by sequencing of a single molecule of DNA. Unlike next generation sequencing methods that rely on amplification to clone many DNA molecules in parallel for sequencing in a phased approach, single molecule sequencing interrogates single molecules of DNA and does not require amplification or synchronization. Single molecule sequencing includes methods that need to pause the sequencing reaction after each base incorporation ('wash-and-scan' cycle) and methods which do not need to halt between read steps. Examples of single molecule sequencing methods include single molecule real-time sequencing (Pacific Biosciences), nanopore-based sequencing (Oxford Nanopore), duplex interrupted nanopore sequencing, and direct imaging of DNA using advanced microscopy.

As used herein, "analyzing" the analyte (e.g., polypeptide) means to identify, quantify, characterize, distinguish, or a combination thereof, all or a portion of the components of the analyte, e.g., the polypeptide. For example, analyzing a peptide, polypeptide, or protein includes determining all or a portion of the amino acid sequence (contiguous or non-continuous) of the peptide. Analyzing a polypeptide also includes partial identification of a component of the polypeptide. For example, partial identification of amino acids in the polypeptide protein sequence can identify an amino acid in the protein as belonging to a subset of possible amino acids. Analysis typically begins with analysis of the n NTAA, and then proceeds to the next amino acid of the peptide (i.e., n-1, n-2, n-3, and so forth). This is accomplished by elimination of the n NTAA, thereby converting the n-1 amino acid of the peptide to an N-terminal amino acid (referred to herein as the "n-1 NTAA"). Analyzing the peptide may also include determining the presence and frequency of post-translational modifications on the peptide, which may or may not include information regarding the sequential order of the post-translational modifications on the peptide. Analyzing the peptide may also include determining the presence and frequency of epitopes in the peptide, which may or may not include information regarding the sequential order or location of the epitopes within the peptide. Analyzing the peptide may include combining different types of analysis, for example obtaining epitope information, amino acid sequence information, post-translational modification information, or any combination thereof.

As used herein, the term "compartment" refers to a physical area or volume that separates or isolates a subset of analytes (e.g., polypeptides) from a sample of polypeptides. For example, a compartment may separate an individual cell from other cells, or a subset of a sample's proteome from the rest of the sample's proteome. A compartment may be an aqueous compartment (e.g., microfluidic droplet), a solid compartment (e.g., picotiter well or microtiter well on a plate, tube, vial, gel bead), a bead surface, a porous bead interior, or a separated region on a surface. A compartment may comprise one or more beads to which polypeptides may be immobilized.

As used herein, the term "compartment tag" or "compartment barcode" refers to a single or double stranded nucleic acid molecule of about 4 bases to about 100 bases (including 4 bases, 100 bases, and any integer between) that comprises identifying information for the constituents (e.g., a single cell's proteome), within one or more compartments (e.g., microfluidic droplet, bead surface). A compartment barcode identifies a subset of polypeptides in a sample that have been separated into the same physical compartment or group of compartments from a plurality (e.g., millions to billions) of compartments. Thus, a compartment tag can be used to distinguish constituents derived from one or more compartments having the same compartment tag from those in another compartment having a different compartment tag, even after the constituents are pooled together. By labeling the proteins and/or peptides within each compartment or within a group of two or more compartments with a unique compartment tag, peptides derived from the same protein, protein complex, or cell within an individual compartment or group of compartments can be identified. A compartment tag comprises a barcode, which is optionally flanked by a spacer sequence on one or both sides, and an optional universal primer. The spacer sequence can be complementary to the spacer sequence of a nucleic acid to which the identifying information from the coding tag is transferred to, enabling transfer of compartment tag information to the nucleic acid. A compartment tag may also comprise a universal priming site, a unique molecular identifier (for providing identifying information for the peptide attached thereto), or both, particularly for embodiments where a compartment tag comprises a bait or capture nucleic acid to be used in downstream peptide analysis methods described herein. A compartment tag can comprise a functional moiety (e.g., aldehyde, NHS, mTet, alkyne, etc.) for coupling to a peptide. Alternatively, a compartment tag can comprise a peptide comprising a recognition sequence for a protein ligase to allow ligation of the compartment tag to a peptide of interest. A compartment can comprise a single compartment tag, a plurality of identical compartment tags save for an optional UMI sequence, or two or more different compartment tags. In certain embodiments each compartment comprises a unique compartment tag (one-to-one mapping). In other embodiments, multiple compartments from a larger population of compartments comprise the same compartment tag (many-to-one mapping). A compartment tag may be joined to a solid support within a compartment (e.g., bead) or joined to the surface of the compartment itself (e.g., surface of a picotiter well). Alternatively, a compartment tag may be free in solution within a compartment.

As used herein, the term "partition" refers to assignment of a unique barcode to a subpopulation of analytes (e.g., peptides) from a population of analytes within a sample. The assignment of the barcode may be random. In certain embodiments, partitioning may be achieved by distributing analytes into compartments. A partition may be comprised of the analytes within a single compartment or the analytes within multiple compartments from a population of compartments.

As used herein, a "partition tag" or "partition barcode" refers to a single or double stranded nucleic acid molecule of about 4 bases to about 100 bases (including 4 bases, 100 bases, and any integer between) that comprises identifying information for a partition. In certain embodiments, a partition tag for a polypeptide refers to identical compartment tags arising from the partitioning of polypeptides into compartment(s) labeled with the same barcode.

As used herein, the term "fraction" refers to a subset of analytes (e.g., polypeptides) within a sample that have been sorted from the rest of the sample or organelles using physical or chemical separation methods, such as fractionating by size, hydrophobicity, isoelectric point, affinity, and so on. Separation methods include HPLC separation, gel separation, affinity separation, cellular fractionation, cellular organelle fractionation, tissue fractionation, etc. Physical properties such as fluid flow, magnetism, electrical current, mass, density, or the like can also be used for separation.

As used herein, the term "fraction barcode" refers to a single or double stranded nucleic acid molecule of about 4 bases to about 100 bases (including 4 bases, 100 bases, and any integer therebetween) that comprises identifying information for the analytes (e.g., polypeptides) within a fraction.

As used herein, the term "coding tag" refers to a polynucleotide with any suitable length, e.g., a nucleic acid molecule of about 2 bases to about 100 bases, including any integer including 2 and 100 and in between, that comprises identifying information for its associated binding agent. A "coding tag" may also be made from a "sequenceable polymer" (see, e.g., Niu et al., 2013, Nat. Chem. 5:282-292; Roy et al., 2015, Nat. Commun. 6:7237; Lutz et al., 2015, Macromolecules 48:4759-4767; each of which are incorporated by reference in its entirety). A coding tag may comprise an encoder sequence, which is optionally flanked by one spacer on one side or optionally flanked by a spacer on each side. A coding tag may also be comprised of an optional UMI and/or an optional binding cycle-specific barcode. A coding tag may be single stranded or double stranded. A double stranded coding tag may comprise blunt ends, overhanging ends, or both. A coding tag may refer to the coding tag that is directly attached to a binding agent, to a complementary sequence hybridized to the coding tag directly attached to a binding agent (e.g., for double stranded coding tags), or to coding tag information present in an extended recording tag. In certain embodiments, a coding tag may further comprise a binding cycle specific spacer or barcode, a unique molecular identifier, a universal priming site, or any combination thereof.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

I. METHOD OF PREPARING ANALYTES AND GENERATING NUCLEIC ACID-ANALYTE CONJUGATES

Provided herein are methods and kits for preparing an analyte (e.g., a macromolecule or a plurality of macromolecules, peptides, polypeptides, and proteins). In some embodiments, the methods and kits are for treating the analytes in preparation for sequencing and/or analysis. In some embodiments, the methods include attaching the analyte to a solid support. In some embodiments, the nucleic acid-analyte conjugate is configured for analysis of the analyte, e.g., wherein the analysis employs barcoding and nucleic acid encoding of molecular recognition events, and/ or detectable labels. In some embodiments, the method includes attaching an analyte to a bait nucleic acid to generate a nucleic acid-analyte chimera. In some aspects, the methods further comprise bringing the nucleic acid-analyte chimera into proximity with a solid support by hybridizing the bait nucleic acid in the nucleic acid-analyte chimera to a capture nucleic acid attached to the solid support, and covalently coupling the nucleic acid-analyte chimera to the solid support. In some embodiments, a plurality of the nucleic acid-analyte chimeras is coupled on the solid support and any adjacently coupled nucleic acid-analyte chimeras are spaced apart from each other at an average distance of about 50 nm or greater. Adjacently coupled nucleic acid-analytes or adjacently coupled nucleic acid-analyte chimeras may refer to molecules that are adjacent to each other in any direction in a two dimensional space. In some cases, adjacently coupled nucleic acid-analytes or adjacently coupled nucleic acid-analyte chimeras may refer to molecules that are adjacent to each other in any direction in a three dimensional space. In some embodiments, the analyte comprises a plurality of analytes (e.g., two or more) that are obtained from a biological sample. In some cases, the analyte is a protein. In some embodiments, the analyte is a peptide, e.g., peptides generated from the fragmenting proteins obtained from a sample. Also provided are nucleic acid-analyte conjugates generated according to any of the methods described herein. In some embodiments, the methods and conjugates described herein are for preparing analytes compatible with protein analysis which employs barcoding and nucleic acid encoding of molecular recognition events, and/or detectable labels.

A. Analytes and Samples

In one aspect, the present disclosure relates to the preparation and treatment of analytes, e.g., macromolecules including proteins, polypeptides, and peptides. In some cases, a macromolecule is any large molecule composed of smaller subunits. In certain embodiments, a macromolecule is a protein, a protein complex, polypeptide, peptide, nucleic acid molecule, carbohydrate, lipid, macrocycle, or a chimeric macromolecule. In certain embodiments, a protein analyte is attached to the solid support via covalently coupling.

In some of any of the provided embodiments, the analytes (e.g., macromolecules, protein, polypeptide, peptide) prepared or treated according the kits and methods disclosed herein may be obtained from a suitable source or sample, including but not limited to: biological samples, such as cells (both primary cells and cultured cell lines), cell lysates or extracts, cell organelles or vesicles, including exosomes, tissues and tissue extracts; biopsy; fecal matter; bodily fluids (such as blood, whole blood, serum, plasma, urine, lymph, bile, cerebrospinal fluid, interstitial fluid, aqueous or vitreous humor, colostrum, sputum, amniotic fluid, saliva, anal and vaginal secretions, perspiration and semen, a transudate, an exudate (e.g., fluid obtained from an abscess or any other site of infection or inflammation) or fluid obtained from a joint (normal joint or a joint affected by disease such as rheumatoid arthritis, osteoarthritis, gout or septic arthritis) of virtually any organism, with mammalian-derived samples, including microbiome-containing samples, being preferred and human-derived samples, including microbiome-containing samples, being particularly preferred; environmental samples (such as air, agricultural, water and soil samples); microbial samples including samples derived from microbial biofilms and/or communities, as well as microbial spores; research samples including extracellular fluids, extracellular supernatants from cell cultures, inclusion bodies in bacteria, cellular and subcellular compartments including mitochondrial compartments, and cellular periplasm. In some cases, the analyte are obtained multiple samples, and the multiple samples are pooled.

In certain embodiments, the analyte is a protein, a protein complex, a polypeptide, or peptide. For example, assessment of the analyte may include determining amino acid sequence information and post-translational modifications of a peptide, polypeptide, or protein by generating a nucleic acid encoded library that can be analyzed via next generation sequencing methods. A peptide, polypeptide, protein, or protein complex may comprise a standard, naturally occurring amino acid, a modified amino acid (e.g., post-translational modification), an amino acid analog, an amino acid mimetic, or any combination thereof. In some embodiments, a peptide, polypeptide, or protein is naturally occurring, synthetically produced, or recombinantly expressed. In any of the aforementioned embodiments, a peptide, polypeptide, protein, or protein complex may further comprise a post-translational modification.

A post-translational modification (PTM) of a peptide, polypeptide, or protein may be a covalent modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation (e.g., N-linked, O-linked, C-linked, phosphoglycosylation), glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide, polypeptide, or protein. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is C1-C4 alkyl). A post-translational modification also includes modifications, such as but not limited to those described above, of amino acids falling between the amino and carboxy termini of a peptide, polypeptide, or protein. Post-translational modification can regulate a protein's "biology" within a cell, e.g., its activity, structure, stability, or localization. Phosphorylation is the most common post-translational modification and plays an important role in regulation of protein, particularly in cell signaling (Prabakaran et al., 2012, Wiley Interdiscip Rev Syst Biol Med 4: 565-583). The addition of sugars to proteins, such as glycosylation, has been shown to promote protein folding, improve stability, and modify regulatory function. The attachment of lipids to proteins enables targeting to the cell membrane. A post-translational modification can also include peptide, polypeptide, or protein modifications to include one or more detectable labels.

In certain embodiments, the analytes (e.g., peptides, polypeptides, or proteins) may be fragmented. For example, the fragmented peptide can be obtained by fragmenting a protein from a sample, such as a biological sample. The peptide, polypeptide, or protein can be fragmented by any means known in the art, including fragmentation by a protease or endopeptidase. For example, the analytes (e.g., peptides, polypeptides, or proteins) are treated with trypsin, LysN, or LysC.

In some embodiments, fragmentation of a peptide, polypeptide, or protein analyte is targeted by use of a specific protease or endopeptidase. A specific protease or endopeptidase binds and cleaves at a specific consensus sequence (e.g., TEV protease which is specific for ENLYFQ\S consensus sequence). In other embodiments, fragmentation of a peptide, polypeptide, or protein is non-targeted or random by use of a non-specific protease or endopeptidase. A non-specific protease may bind and cleave at a specific amino acid residue rather than a consensus sequence (e.g., proteinase K is a non-specific serine protease). Proteinases and endopeptidases are known in the art, and examples of such that can be used to cleave a protein or polypeptide into smaller peptide fragments include proteinase K, trypsin, chymotrypsin, pepsin, thermolysin, thrombin, Factor Xa, furin, endopeptidase, papain, pepsin, subtilisin, elastase, enterokinase, Genenase™ I, Endoproteinase LysC, Endoproteinase AspN, Endoproteinase GluC, etc. (Granvogl et al., 2007, Anal Bioanal Chem 389: 991-1002). In certain embodiments, a peptide, polypeptide, or protein is fragmented by proteinase K, or optionally, a thermolabile version of proteinase K to enable rapid inactivation. Proteinase K is quite stable in denaturing reagents, such as urea and SDS, enabling digestion of completely denatured proteins. Protein and polypeptide fragmentation into peptides can be performed before or after attachment to the bait nucleic acid or other nucleic acid components.

Chemical reagents can be used to digest proteins into peptide fragments. A chemical reagent may cleave at a specific amino acid residue (e.g., cyanogen bromide hydrolyzes peptide bonds at the C-terminus of methionine residues). Chemical reagents for fragmenting polypeptides or proteins into smaller peptides include cyanogen bromide (CNBr), hydroxylamine, hydrazine, formic acid, BNPS-skatole [2-(2-nitrophenylsulfenyl)-3-methylindole], iodosobenzoic acid, •NTCB+Ni (2-nitro-5-thiocyanobenzoic acid), etc.

In some embodiments, the analytes attached to the bait nucleic acid comprises fragmented protein or peptide. In certain embodiments, following enzymatic or chemical cleavage, the resulting peptide fragments are approximately the same desired length, e.g., from about 10 amino acids to about 70 amino acids, from about 10 amino acids to about 60 amino acids, from about 10 amino acids to about 50 amino acids, about 10 to about 40 amino acids, from about 10 to about 30 amino acids, from about 20 amino acids to about 70 amino acids, from about 20 amino acids to about 60 amino acids, from about 20 amino acids to about 50 amino acids, about 20 to about 40 amino acids, from about 20 to about 30 amino acids, from about 30 amino acids to about 70 amino acids, from about 30 amino acids to about 60 amino acids, from about 30 amino acids to about 50 amino acids, or from about 30 amino acids to about 40 amino acids. A cleavage reaction may be monitored, for example in real time, by spiking the protein or polypeptide sample with a short test FRET (fluorescence resonance energy transfer) peptide comprising a peptide sequence containing a proteinase or endopeptidase cleavage site. In the intact FRET peptide, a fluorescent group and a quencher group are attached to either end of the peptide sequence containing the cleavage site, and fluorescence resonance energy transfer between the quencher and the fluorophore leads to low fluorescence. Upon cleavage of the test peptide by a protease or endopeptidase, the quencher and fluorophore are separated giving a large increase in fluorescence. A cleavage reaction can be stopped when a certain fluorescence intensity is achieved, allowing a reproducible cleavage end point to be achieved.

In certain embodiments, a plurality of protein analytes is attached to the solid support. For example, a sample of proteins is obtained from a biological sample and fragmented. In some embodiments, a plurality of fragmented proteins are attached to the solid support (e.g., a plurality of solid supports) by performing any of the methods provided herein. In some embodiments, a plurality of fragmented peptides are attached to a bead. In some cases, the fragmented proteins attached to the solid support (e.g., a bead) is a random portion of the total fragmented proteins. In some cases, the identity of the analytes attached to the solid support is not known. In some embodiment, the analytes attached to the solid support are not targeted. In some embodiments, the analytes attached to the solid support are of unknown identity and the methods provided herein generate nucleic acid-analyte conjugates for use with an analysis method that can be used to characterize, assess, identify, analyze and/or sequence the analytes.

In some embodiments, the analytes are obtained from a sample, and the analytes may undergo protein fractionation methods prior to attachment to the bait nucleic acid. In some embodiments, the analytes are obtained from a sample, and the analytes may undergo protein fractionation methods after attachment to a bait nucleic acid. In some embodiments, the analytes are obtained from a sample, and the analytes may undergo protein fractionation methods prior to attachment to a solid support. In some embodiments, the analytes are obtained from a sample, and the analytes may undergo protein fractionation methods after attachment to a solid support.

In some embodiments, the analytes (e.g., proteins or peptides) are separated using one or more properties such as cellular location, molecular weight, hydrophobicity, or isoelectric point, or protein enrichment methods. Alternatively, or additionally, protein enrichment methods may be used to select for a specific protein or peptide (see, e.g., Whiteaker et al., 2007, Anal. Biochem. 362:44-54, incorporated by reference in its entirety) or to select for a particular post translational modification (see, e.g., Huang et al., 2014. J. Chromatogr. A 1372:1-17, incorporated by reference in its entirety). Alternatively, a particular class or classes of proteins such as immunoglobulins, or immunoglobulin (Ig) isotypes such as IgG, can be affinity enriched or selected for analysis. In the case of immunoglobulin molecules, analysis of the sequence and abundance or frequency of hypervariable sequences involved in affinity binding are of particular interest, particularly as they vary in response to disease progression or correlate with healthy, immune, and/or or disease phenotypes. Overly abundant proteins can also be subtracted from the sample using standard immunoaffinity methods. Depletion of abundant proteins can be useful for plasma samples where over 80% of the protein constituent is albumin and immunoglobulins. Several commercial products are available for depletion of plasma samples of overly abundant proteins, such as PROTIA and PROT20 (Sigma-Aldrich).

In certain embodiments, the analyte comprises a protein or polypeptide. In one embodiment, the protein or polypeptide analyte is attached to a nucleic acid polymer (e.g., bait nucleic acid). In some embodiments, the analyte is attached directly to the bait nucleic acid. In some embodiments, the analyte is attached indirectly the bait nucleic acid (e.g., via a linker). Various linkers are known in the art and can optionally be used to attach the analyte to the bait nucleic acid. In some embodiments, the protein or polypeptide is labeled with a reactive coupling moiety such as an amine-reactive coupling agent for attaching to the bait nucleic acid. For example, the lysine residues of the protein or polypeptide are labeled with a reactive coupling moiety.

In some embodiments, the analyte and/or bait nucleic comprises a reactive coupling moiety. A bait nucleic acid may be attached to the analyte in any suitable position and configuration, as long as the attachment is compatible with the method used to transfer coding tag information to the nucleic acid in a protein sequencing or analysis assay. In some embodiments, the analyte is attached to the bait nucleic acid (directly or using a suitable linker) at various positions of the bait nucleic acid such as at the 3' end or at the 5' end of the bait nucleic acid. In some embodiments, the analyte is attached to the bait nucleic acid (directly or using a suitable linker) at an internal position of the bait nucleic acid.

In some embodiments, the bait nucleic acid comprises a modified base (e.g., i5-Octadiynyl dU). For example, the modified base comprises an alkyne or the modified base is configured for inserting a reactive coupling moiety (e.g., an alkyne) to the bait nucleic acid. In some examples, the reactive coupling moiety is for attaching the bait nucleic acid to the analyte. In some embodiments, the analyte is attached to the bait nucleic acid using chemical ligation. The bait nucleic acid can be attached to the analyte using one or more linkers.

In a particular embodiment, the bait nucleic acid comprises a reactive coupling moiety (e.g., for conjugation to the analyte), a linker, a universal priming sequence, a barcode (e.g., compartment tag, partition barcode, sample barcode, fraction barcode, or any combination thereof), an optional UMI, and a spacer (Sp) sequence. In some embodiments, the bait nucleic acid comprises a spacer sequence for facilitating information transfer from another nucleic acid polymer.

B. Coupling the Analyte to the Solid Support Via Hybridization of the Bait Nucleic Acid and Capture Nucleic Acid In some aspects, the methods and conjugates provided herein comprise a treating an analyte including attaching an analyte to a bait nucleic acid to generate a nucleic acid-analyte chimera and bringing the nucleic acid-analyte chimera into proximity with a solid support by hybridizing the bait nucleic acid in the nucleic acid-analyte chimera to a capture nucleic acid attached to the solid support. In some embodiments, one or more of the capture nucleic acid, the nucleic acid-analyte chimera, and/or the bait nucleic acid further comprises a barcode or other nucleic acid components. In some cases, the methods provided include attaching a barcode to the coupled nucleic acid-analyte chimera on a solid support prior to coupling to the solid support.

In some embodiments, the nucleic acid components and nucleic acid tags (e.g., bait or capture nucleic acid, barcodes, UMI) may include a strand of DNA or RNA, or a chimeric DNA-RNA strand, or nucleic acid-like compounds such as peptide nucleic acids. In some embodiments, a nucleic acid strand can also include modified DNA or RNA bases, such as those known in the art.

In some embodiments, the bait nucleic acid comprises a single stranded region for hybridizing to the capture nucleic acid. In some embodiments, the bait nucleic acid comprises at least one nucleic acid region which is substantially complementary to a capture nucleic acid. In some examples, the bait nucleic acid comprises a sequence of nucleotides that binds selectively to the capture nucleic acid sequence. In some embodiments, the capture nucleic acid comprises a single stranded region which is substantially complementary to the bait nucleic acid. "Substantially complementary" refers to sequences that are capable of hybridizing to a target nucleic acid sequence under the conditions employed. In preferred embodiments, a "substantially complementary" single-stranded region is exactly complementary to a target nucleic acid sequence. For example, the single-stranded region of the capture nucleic acid complementary to the bait nucleic acid may have at least 5 bases, at least 6 bases, at least 7 bases, at least 8 bases, at least 9 bases, at least 10 bases, at least 12 bases, at least 14 bases, at least 16 bases, at least 20 bases, at least 24 bases, at least 30 bases, or at least 34 bases. In some embodiments, the single-stranded region of the capture nucleic acid complementary to the bait nucleic acid has fewer than 40 bases, fewer than 30 bases, or fewer than 25 bases.

In some cases, the hybridization of the bait nucleic acid to the capture nucleic comprises hybridization of 8 or more complementary bases, 16 or more complementary bases, 18 or more complementary bases, 24 or more complementary bases, 34 or more complementary bases. In one embodiment, the hybridization of the bait nucleic acid to the capture nucleic comprises hybridization of 16 or more complementary bases. In some embodiments, the hybridization of the bait nucleic acid to the capture nucleic comprises hybridization of 18 or more complementary bases. In some embodiments, the hybridization of the bait nucleic acid to the capture nucleic comprises hybridization of 20 or more complementary bases. In some embodiments, the hybridization of the bait nucleic acid to the capture nucleic comprises hybridization of 24 or more complementary bases. One skilled in the art may select complementary regions with number of bases that is sufficient for forming stable hybridization regions between the bait nucleic acid and the capture nucleic acid. In some embodiments, the region of the capture nucleic acid for hybridizing to the bait nucleic acid is located at the 3' or the 5' end of the capture nucleic acid.

In some embodiments, the capture nucleic acid comprises a splinted nucleic acid strand, wherein the splint bridges the capture nucleic acid and bait via hybridization and enables efficient ligation or chemical coupling. In some embodiments, the splinted nucleic acid is separate from the capture nucleic acid. In some embodiments, the bait nucleic acid comprises a splinted nucleic acid strand, wherein the splint bridges the capture nucleic acid and bait via hybridization and enables efficient ligation or chemical coupling. In some embodiments, the splinted nucleic acid is separate from the bait nucleic acid.

In some provided embodiments, the bait nucleic acid is coupled to the capture nucleic acid. In some examples, the coupling of the bait nucleic acid to the capture nucleic acid is through covalent coupling. In some examples, the 5' end of the bait nucleic acid is coupled to the 3' end of the capture nucleic acid. In some cases, the 3' end of the bait nucleic acid is coupled to the 5' end of the capture nucleic acid. For example, the analyte-bait nucleic acid conjugate hybridizes to the nucleic acid-analyte chimera and is attached to the 5' end of the capture nucleic acid (FIG. 1C-1D).

In some cases, the capture nucleic acid is immobilized on solid support, directly or indirectly. In some embodiments, the capture nucleic acid is attached to the solid support prior to bringing the hybridizing the bait nucleic acid to the capture nucleic acid. The hybridization of the bait and capture nucleic acids increases efficiency of the immobilization, such as compared to chemical coupling. In some embodiments, the capture nucleic acid comprises a reactive coupling moiety. In some embodiments, the solid support comprises a reactive coupling moiety. In some embodiments, the reactive coupling moiety is attached to the solid support prior to or simultaneously with attaching the solid support to the capture nucleic acid.

In some embodiments, the capture and/or bait nucleic acid comprises a reactive coupling moiety. For example, the reactive coupling moiety is for covalently coupling the bait and capture nucleic acids. In some embodiments, the bait nucleic acid is coupled to the capture nucleic acid using chemical linkage. Standard chemical ligation or "click chemistry" may be used to couple the bait nucleic acid and capture nucleic acid (Gunderson et al., Genome Res (1998) 8(11): 1142-1153; Peng et al., European J Org Chem (2010)

(22): 4194-4197; El-Sagheer et al., Proc Natl Acad Sci USA (2011) 108(28): 11338-11343; El-Sagheer et al., Org Biomol Chem (2011) 9(1): 232-235; Sharma et al., Anal Chem (2012) 84(14): 6104-6109; Roloff et al., Bioorg Med Chem (2013) 21(12): 3458-3464; Litovchick et al., Artif DNA PNA XNA (2014) 5(1): e27896; Roloff et al., Methods Mol Biol (2014) 1050:131-141). In some embodiments, the bait nucleic acid is coupled to the capture nucleic acid using photo- or light-activated linkage (e.g., photo cross-linkage). One skilled in the art may determine methods to couple various linkage moieties to the bait nucleic acid. For example, the bait nucleic acid or nucleic acid-analyte chimera comprises a photoactive moiety. In some embodiments, cell lines may be engineered to produce specific moieties for attachment. In some embodiments, a photoactive benzophenone moiety is added to the bait nucleic acid. In some specific cases, the photoactive benzophenone moiety is attached to the bait nucleic acid using an alkyne-benzophenone and azide-oligo. In some examples, the capture nucleic acids attached to a solid support comprises a reactive psoralen moiety. In some embodiments, the analytes are immobilized to a surface derivatized with complementary capture nucleic acids by hybridization of bait nucleic acids to the complementary capture nucleic acids. The capture nucleic acids may comprise a reactive psoralen moiety and exposure to UV light covalently couples the bait nucleic acid and capture nucleic acids (FIG. 2A-2C).

In one embodiment, the bait and capture nucleic acid do not comprise a nucleic acid hairpin. In some embodiments, the hybridized bait and capture nucleic acid forms a double stranded nucleic acid structure. In one embodiment, the bait nucleic acid hybridizes to the capture nucleic acid and the nucleic acid-analyte chimera directly or indirectly attaches to the solid support.

In some cases, the bait nucleic acid is attached to the capture nucleic acid using ligation. For enzymatic ligation of DNA, a 5' phosphate of the capture nucleic acid is required to ligate to the 3' hydroxyl of the bait nucleic acid. In some other cases, a 5' phosphate of the bait nucleic acid is required to ligate to the 3' hydroxyl of the capture nucleic acid. In some of any of the provided embodiments, the attachment may be to an additional nucleic acid sequence (e.g., a barcode, UMI, spacer) that is attached to the bait or capture nucleic acid.

In one embodiment, the bait or capture nucleic acid comprises a splinted nucleic acid strand, wherein the splint bridges the bait and capture nucleic acid via hybridization and enables efficient ligation or chemical coupling. In some embodiments, the capture nucleic acid comprises a splinted nucleic acid strand. In some embodiments, the splint nucleic acid strand is transiently used. In some embodiments, the splint nucleic acid strand is removed after the bait nucleic acid-analyte chimera is attached or coupled to a solid support, a bead, via the capture nucleic acid. In another embodiment, the bait or capture nucleic acid comprises a nucleic acid hairpin (see e.g., Riccelli et al., Nucleic Acids Res. (2001) 29(4): 996-1004). The nucleic acid hairpin is a unimolecular nucleic acid-containing structure which comprises at least two mutually complementary nucleic acid regions such that at least one intramolecular duplex can form (see e.g., U.S. Pat. No. 5,770,365). In certain embodiments, the mutually complementary nucleic acid regions are connected through a nucleic acid strand. In some examples, the hairpin comprises a single strand of nucleic acid.

In some specific examples, the hairpin of the capture nucleic acid forms at least one intramolecular duplex having at least 2 base pairs, at least 4 base pairs, at least 8 base pairs, at least 16 base pairs, at least 24 base pairs, at least 32 base pairs, and at least 40 base pairs in length. One skilled in the art will be able to adjust the size, number of base pairs in the duplex region and the configuration to achieve any desired relative stability of duplex formation. In some embodiments, the intramolecular duplex comprises less than about 40 base pairs, less than 30 base pairs, or less than 20 base pairs in length. In some examples, the hairpin of the capture nucleic acid forms at least one intramolecular duplex comprising 16 base pairs in length.

In some embodiments, the capture nucleic acid comprises a region which connects regions of mutual complementarity, referred to herein as a "loop" or "linker". In preferred embodiments, a loop comprises a strand of nucleic acid or modified nucleic acid. In some examples, the nucleic acid loop comprises 2-20 nucleotides, such as 3-8 nucleotides. In other embodiments, the loop comprises a linker region which is not nucleic-acid-based. Various non-nucleic-acid linkers suitable for use in the loop region are known in the art including, for example, alkyl chains (see, e.g., Doktycz et al. (1993) Biopolymers 33:1765). In some embodiments, the size, composition, and configuration of the loop or linker is selected to allow the regions of mutual complementarity to form an intramolecular duplex. In some cases, the hairpin is capable of forming more than one loop.

In some embodiments, at least one of the bait nucleic acids further comprises a barcode. In some embodiments, at least one of the bait nucleic acids further comprises a unique molecule identifier (UMI). In some embodiments, at least one of the capture nucleic acids further comprises a barcode. In some embodiments, at least one of the capture nucleic acids further comprises a unique molecule identifier (UMI). In some embodiments, the barcode comprises a UMI. In some embodiments, the barcode comprises a sample barcode, a fraction barcode, spatial barcode, a compartment tag, or any combinations thereof. In some examples, the barcode and/or UMI comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof.

The UMI may be a unique identifier tag for each analyte (e.g., macromolecule, protein, polypeptide, peptide). A UMI can be about 3 to about 40 bases, about 3 to about 30 bases, about 3 to about 20 bases, or about 3 to about 10 bases, or about 3 to about 8 bases. In some embodiments, a UMI is about 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 25 bases, 30 bases, 35 bases, or 40 bases in length. A UMI can be used to de-convolute sequencing data from methods used to determine the sequence of the analyte, to identify sequence reads from individual analytes. In some embodiments, within a library of analytes, each analyte is associated with a single unique UMI. In other embodiments, analytes might be fragmented and multiple portions of the analyte may be associated with the same UMI. In some embodiments, a UMI has a different base sequence than the spacer or other barcode sequences to facilitate distinguishing these components during sequence analysis.

In some embodiments, the one or more barcodes is attached to the bait nucleic acid, the capture nucleic acid, and/or the nucleic acid-analyte conjugate. In some other embodiments, the one or more barcodes is attached or installed to the nucleic acid-analyte conjugate coupled to the solid support. In some embodiments, the nucleic acid-analyte chimera can be labeled with a nucleic acid tag, such as a barcode, such as prior to coupling to the solid support. In some examples, the nucleic acid-analyte chimera can be first labeled with a universal DNA tag. In some cases, the barcode may comprise information representing a sample, a compartment, a physical location, a spatial barcode, etc. See e.g., International Patent Publication No. WO 2014/201273. In some cases, the barcode or other nucleic acid tags are attached to the protein through and enzymatic or chemical coupling step.

In some embodiments, the capture nucleic acid includes a hairpin which may include one or more barcode sequences for various types of identifying information. For example, a capture nucleic acid may include a barcode with information regarding the support (e.g., bead) to which the polypeptide was immobilized. In some embodiments, the bait nucleic acid may include one or more barcode sequences for various types of identifying information. For example, a bait nucleic acid may include a sample barcode and/or a barcode useful for identifying control peptides. The capture nucleic acid and/or bait nucleic acid may contain an optional UMI sequence in addition to one or more barcode sequences.

In some embodiments, the methods provided herein for preparing the analyte further comprises attaching one or more barcodes to the bait nucleic acid. In some embodiments, the methods provided herein for preparing the analyte further comprises attaching one or more barcodes to the capture nucleic acid. The attaching of the one or more barcodes comprises a enzymatic or chemical method. In some embodiments, the barcode is attached using nucleic acid extension (e.g., PCR extension). In some embodiments, the barcode is attached to the bait or capture nucleic acid using a ligation reaction. In some examples, two or more barcodes are attached to the bait nucleic acid. In some examples, two or more barcodes are attached to the capture nucleic acid.

In some embodiments, the barcode is attached to the 5' end of the bait nucleic acid. In some embodiments, the barcode is attached to the 3' end of the bait nucleic acid. In some embodiments, the barcode is attached to the 5' end of the capture nucleic acid. In some embodiments, the barcode is attached to the 3' end of the capture nucleic acid. In some embodiments, the barcode is attached to the 5' end of the nucleic acid-analyte chimera. In some embodiments, the barcode is attached to the 3' end of the nucleic acid-analyte chimera. In some embodiments, the barcode is attached to the 5' end of the nucleic acid-analyte conjugate coupled to the solid support. In some embodiments, the barcode is attached to the 3' end of the nucleic acid-analyte conjugate coupled to the solid support. In some specific embodiments, the 5' end of the barcode is phosphorylated.

In some embodiments, the methods provided herein are used to prepare solid supports coupled with bait nucleic acids with analytes attached such that the analyte is barcoded. In some embodiments, the solid support is coupled with a plurality of nucleic acids associated with each analyte, and the barcodes used comprises a variety of barcode sequences.

The barcode may be added using a barcode template (BC') that comprises a nucleic acid sequence that is complementary to the bait nucleic acid. In some embodiments, the barcode template is or comprises DNA. In some embodiments, the barcode template is or comprises RNA. In some embodiments, the barcode template used for attaching a barcode to the bait or capture nucleic acid is configured to hybridize to the bait or capture nucleic acid. In some embodiments, the method for attaching the barcode may further comprises a digestion reaction. In some embodiments, the digestion reaction is performed after the barcode has been transferred from the barcode template. In some embodiments, a barcode is attached to the bait nucleic acid prior to attaching the analyte to the bait nucleic acid. In some embodiments, a barcode is attached to the bait nucleic acid after attaching the analyte to the bait nucleic acid. In some examples, the attachment of the barcode can be performed using extension, primer extension, or ligation. In some embodiments, the nucleic acid-analyte chimera with the newly installed barcode is washed, treated with a digestion enzyme, and/or treated with heat.

FIG. 3-9 are schematics depicting exemplary methods for attaching a barcode to the bait nucleic acid, the capture nucleic acid, the nucleic acid-analyte chimera, or the nucleic acid-analyte conjugate coupled to the solid support.

In some specific embodiments, the analyte is attached to the bait nucleic acid; a barcode template (BC') hybridizes to the nucleic acid-analyte chimera; an extension reaction is used to extend the 3' end of the bait nucleic acid to include the barcode sequence; the nucleic acid-analyte chimera with the newly extended barcode is brought into proximity with a solid support by hybridizing the bait nucleic acid (with the analyte and barcode) to a capture nucleic acid attached to the solid support; the nucleic acid-analyte chimera is covalently coupled to the solid support by attaching (e.g., via ligation) the capture nucleic acid and the bait nucleic acid (FIG. 3).

In some specific embodiments, the analyte is attached to the bait nucleic acid; the nucleic acid-analyte chimera is brought into proximity with a solid support by hybridizing the bait nucleic acid (with the analyte) to a capture nucleic acid attached to the solid support; the nucleic acid-analyte chimera is covalently coupled to the solid support by attaching (e.g., via ligation) the capture nucleic acid and the bait nucleic acid; a barcode template (BC') is used to extend the 3' end of the bait nucleic acid to include the barcode sequence; a digestion reaction is used to release the barcode template from the nucleic-acid analyte conjugate coupled on the solid support (FIG. 4).

In some aspects, attaching the barcode may comprise primer extension. In some examples, primer extension is performed by incubating at 25° C.-37° C. with a reaction solution that comprises Klenow fragment (exo-) and a template barcode such that the barcode is installed on the bait nucleic acid. In some examples, the barcode template comprises a dU-containing nucleic acid. In some embodiments, a washing step is performed after the barcode is installed. In some aspects, the capture nucleic acid comprises a sequence of nucleic acids complementary to the barcode template. In some cases, the bait or capture nucleic acid is configured to allow hybridization to the barcode template. In some examples, an extension reaction is performed by incubating the nucleic-acid analyte conjugates coupled to the solid support at 25° C.-37° C. for 5 min with a reaction solution including Klenow fragment (exo-) to extend the bait nucleic acid to install the barcode. In some embodiments, the nucleic acid-analyte conjugate with the barcode installed by extension is washed and treated with USER enzyme (New England Biolabs) to remove any digested strand for assay.

In some specific embodiments, the analyte is attached to the bait nucleic acid; a ligation reaction is used to attach the bait nucleic acid to the barcode; the nucleic acid-analyte chimera with the attached barcode is brought into proximity with a solid support by hybridizing the bait nucleic acid (with the analyte and barcode) to a capture nucleic acid attached to the solid support; the nucleic acid-analyte chimera is covalently coupled to the solid support by attaching (e.g., via ligation) the capture nucleic acid and the bait nucleic acid. In one embodiment, the bait nucleic acid comprises a splinted nucleic acid strand, wherein the splint bridges the bait nucleic acid and barcode via hybridization and enables efficient ligation or chemical coupling. (FIG. 5).

Figure 7:
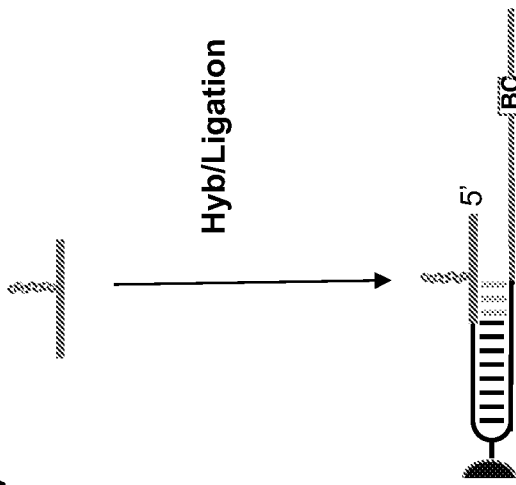
Figure 6:
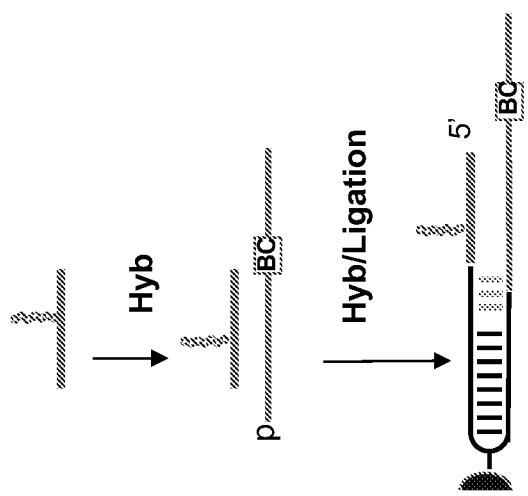

FIGS. 6 and 7 depicts the attachment of a barcode to the 3' end of the capture nucleic acid and coupling of a nucleic acid-analyte chimera to the solid support by attaching the bait nucleic acid to the 5' capture nucleic acid. In some specific embodiments, the analyte is attached to the bait nucleic acid; the nucleic acid-analyte chimera is brought into proximity with a solid support by hybridizing the bait nucleic acid to a capture nucleic acid attached to the solid support; the nucleic acid-analyte chimera is covalently coupled to the solid support by attaching (e.g., via ligation) the 5' end of the capture nucleic acid and the 3' bait nucleic acid; a barcode is attached to the 3' end of the capture nucleic acid (e.g., via ligation) (FIG. 6). In some embodiments, the bait nucleic acid of the nucleic acid-analyte chimera is attached to the 5' end of a capture nucleic acid that is attached to the solid support and the capture nucleic acid includes a barcode sequence (FIG. 7).

Figures 8, 9:
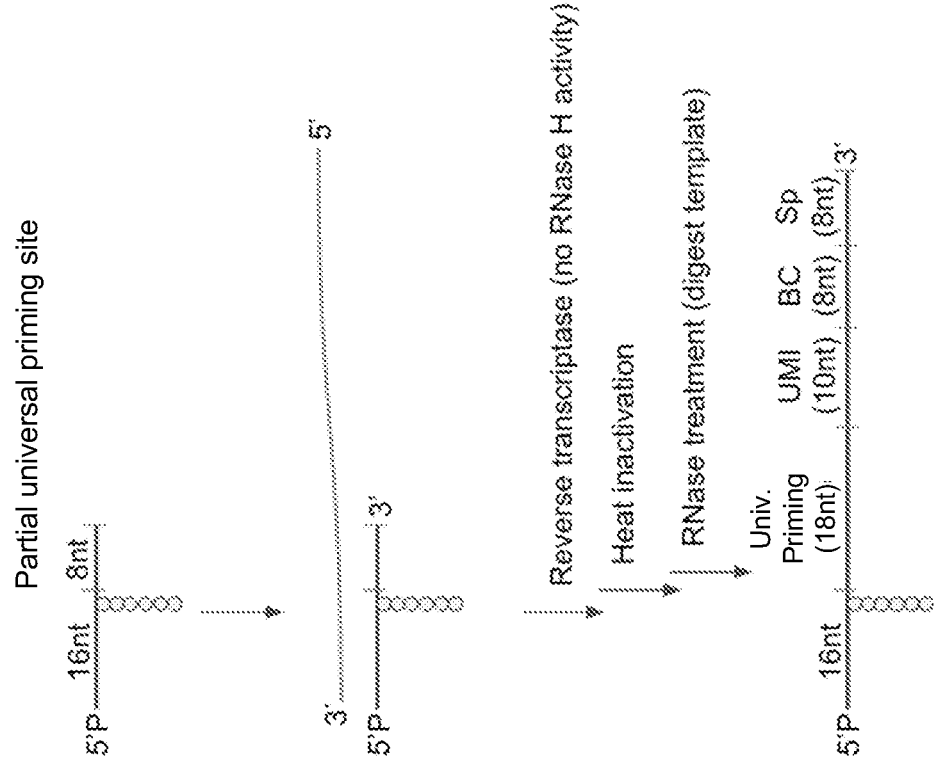
FIG. 8 depicts steps for installing a barcode and optionally other nucleic acid components onto the bait nucleic acid. A nucleic acid-analyte chimera is hybridized to nucleic acid template containing multiple dU, UMI, barcode and/or spacer sequences; primer extension is performed in a reaction (e.g., including Klenow fragment (exo-) at 25° C.) to install the UMI, barcode and/or spacer from the template barcode onto the bait nucleic acid (attached to an analyte); the resulting dsDNA is treated with USER enzyme to digest the dU sites, and heated to remove the digested fragment. The bait nucleic acid in some cases includes a universal priming site or a portion thereof.
FIG. 9 depicts steps for installing a barcode and optionally other nucleic acid components onto the bait nucleic acid using reverse transcription. A RNA barcode template containing a UMI, barcode and/or spacer sequence is used and reverse transcription is performed in a reaction with reverse transcriptase (RNase H-) at about 50° C. for about 1 hour to install the UMI, barcode and/or spacer sequences onto the bait nucleic acid); the resulting RNA/DNA hybrid is treated with RNase to digest the RNA barcode template. The bait nucleic acid in some cases includes a universal priming site or a portion thereof.

In some aspects, attaching the barcode may comprise using a dU-containing nucleic acid barcode template. In some aspects, attaching the barcode may further comprise treating the bait nucleic acid, capture nucleic acid, or nucleic acid-analyte chimera with an USER enzyme. In some aspects, the provided methods for attaching or installing a barcode comprise treating a nucleic acid with an installed barcode with an USER enzyme. For example, the chimera is hybridized to nucleic acid barcode template containing multiple dU, UMI, barcode and/or spacer sequences; primer extension is performed in a reaction including Klenow fragment (exo-) at 25° C.-37° C. to install the UMI, barcode and/or spacer from the template onto the bait nucleic acid (attached to an analyte); the resulting dsDNA is treated with USER enzyme (New England Biolabs) to digest the dU sites, and heated to remove the digested fragment (FIG. 8).

In some aspects, attaching the barcode may comprise using an RNA barcode template. For example, a reverse transcription reaction can be used to install the barcode onto the bait nucleic acid. In some aspects, the barcode template may include using an RNA template containing a UMI, barcode and/or spacer sequence. For example, reverse transcription is performed in a reaction containing reverse transcriptase (RNase H-) to install the UMI, barcode and/or spacer sequences onto the bait nucleic acid. In some cases, the reaction with the reverse transcriptase can be treated with heat to inactivate the reverse transcriptase. In some cases, the resulting RNA/DNA hybrid is treated with RNase A and Ti cocktail (Thermo Fisher) and RNase H to digest RNA barcode template (FIG. 9). In some embodiments, the nucleic acid-analyte chimera with the newly installed barcode is then brought into proximity with a solid support by hybridizing the bait nucleic acid (with the analyte and barcode) to a capture nucleic acid attached to the solid support; the nucleic acid-analyte chimera is covalently coupled to the solid support by attaching (e.g., via ligation) the capture nucleic acid and the bait nucleic acid.

The bait nucleic acid and/or capture nucleic acid may further comprise other functional components, e.g., a universal priming site, a spacer sequence that is complementary to a spacer sequence attached to another nucleic acid moiety, or any combination thereof. In some embodiments, the capture nucleic acid comprises an adaptor sequence for use in a downstream sequencing step (e.g., flow cell adaptor sequences that anneal to complementary oligonucleotides on flow cell surfaces for next generation sequencing platforms). In certain embodiments, a universal DNA sequence is a universal priming sequence. Upon hybridization of the universal sequence on the labeled protein to complementary sequence of the bait or capture nucleic acid (e.g., bound to beads), the annealed universal sequence may be extended via primer extension. In some embodiments, the universal priming site comprises a priming site for amplification, sequencing, or both. In some embodiments, the universal reverse priming site is an Illumina P7 primer (5'-CAAGCAGAAGACGGCATACGAGAT-3'-SEQ ID NO:2) or an Illumina P5 primer (5'-AATGATACGGCGAC-CACCGA-3'-SEQ ID NO: 1). In some embodiments, the universal priming sites used comprises the sequences 5'-ACACTCTTTCCCTACACGACGCTCTTCCGATCT-3' (SEQ ID NO: 32) and 5'-GACTGGAGTTCA-GACGTGTGCTCTTCCGATCT-3' (SEQ ID NO: 33).

In some embodiments, a downstream sequencing step may use an adapter to one or both ends of the recording tag nucleic acid. The sequencing can be achieved by any of the commercially available sequencing instruments or by any known methods. In some examples, the capture nucleic acid comprises an index sequence, an adaptor sequence, a nucleic acid domain that specifically binds to a surface-attached sequencing platform oligonucleotide, or any combinations thereof. In one example, an adapter is included in the capture nucleic acid and is designed to be used with an Illumina sequencing machine. Sequencing platforms of interest may include, but are not limited to, the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other sequencing platform.

In some embodiments, the bait nucleic acid comprises the spacer polymer at its 5'-terminus and/or 3'-terminus. In some embodiments, the capture nucleic acid comprises the spacer polymer at its 5'-terminus and/or 3'-terminus. The spacer sequence is, in some examples, at the 3'-end of the bait nucleic acid. The spacer sequence is, in some examples, at the 5'-end of the bait nucleic acid. In some embodiments, the spacer sequence is configured to allow transfer of nucleic acid information using polymerase extension to the bait or capture nucleic acid. In some embodiments, the spacer sequence is configured to allow transfer of nucleic acid information using polymerase extension to the nucleic acid-analyte conjugate coupled to the solid support.

In some embodiments, the spacer polymer comprises at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 15 nucleotides, or at least 20 or more nucleotides. The spacer polymer may comprise any suitable nucleic acid, for example, a DNA molecule, DNA with pseudo-complementary bases, an RNA molecule, a BNA molecule, an XNA molecule, a LNA molecule, a PNA molecule, a γPNA molecule; a non-nucleic acid sequenceable polymer, e.g., a polysaccharide, a polypeptide, a peptide, or a polyamide, or a combination thereof.

In some particular embodiments, the bait nucleic acid further comprises the following at its 5' or 3' end: a universal primer site for PCR reaction, a UMI, a sample barcode, and a spacer (universal sequence). In some particular embodiments, the capture nucleic acid further comprises the following at its 5' or 3' end: a spacer (universal sequence), a sample barcode, a UMI, and a universal primer site for PCR reaction. In some aspects, the order of the nucleic acid components may be combined in various ways. In some preferred embodiments, a spacer sequence is preferably at the 3'-end of the nucleic acid to which the identifying information from the binding agent is transferred to, in embodiments where polymerase extension is used to transfer coding tag information to the nucleic acid associated with the analyte.

A solid support can be any support surface including, but not limited to, a bead, a microbead, an array, a glass surface, a silicon surface, a plastic surface, a filter, a membrane, a PTFE membrane, nylon, a silicon wafer chip, a flow cell, a flow through chip, a biochip including signal transducing electronics, a microtiter well, an ELISA plate, a spinning interferometry disc, a nitrocellulose membrane, a nitrocellulose-based polymer surface, a nanoparticle, or a microsphere. Materials for a solid support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, nylon, silicon rubber, silica, polyanhydrides, polyglycolic acid, polyvinylchloride, polylactic acid, polyorthoesters, functionalized silane, polypropylfumerate, collagen, glycosaminoglycans, polyamino acids, or any combination thereof. In certain embodiments, a solid support is a bead, for example, a polystyrene bead, a polymer bead, a polyacrylate bead, an agarose bead, a cellulose bead, a dextran bead, an acrylamide bead, a solid core bead, a porous bead, a paramagnetic bead, a glass bead, a silica-based bead, or a controlled pore bead, or any combinations thereof.

In some embodiments, the capture nucleic acid is derivatized or comprises a moiety (e.g., a reactive coupling moiety) to allow binding to a solid support. In some embodiments, the capture nucleic acid comprises a moiety (e.g., a reactive coupling moiety) to allow binding to the bait nucleic acid. In some other embodiments, the bait nucleic acid is derivatized or comprises a moiety (e.g., a reactive coupling moiety) to allow binding to a solid support. Methods of derivatizing a nucleic acid for binding to a solid support and reagents for accomplishing the same are known in the art. For this purpose, any reaction which is preferably rapid and substantially irreversible can be used to attach nucleic acids to the solid support. The capture nucleic acid may be bound to a solid support through covalent or non-covalent bonds. In a preferred embodiment, the capture nucleic acid is covalently bound to biotin to form a biotinylated conjugate. The biotinylated conjugate is then bound to a solid surface, for example, by binding to a solid, insoluble support derivatized with avidin or streptavidin. The capture nucleic acid can be derivatized for binding to a solid support by incorporating modified nucleic acids in the loop region. In other embodiments, the capture moiety is derivatized in a region other than the loop region.

Exemplary reactions include the copper catalyzed reaction of an azide and alkyne to form a triazole (Huisgen 1, 3-dipolar cycloaddition), strain-promoted azide alkyne cycloaddition (SPAAC), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse electron demand Diels-Alder (IEDDA) reaction (e.g., m-tetrazine (mTet) or phenyl tetrazine (pTet) and trans-cyclooctene (TCO); or pTet and an alkene), alkene and tetrazole photoreaction, Staudinger ligation of azides and phosphines, and various displacement reactions, such as displacement of a leaving group by nucleophilic attack on an electrophilic atom (Horisawa 2014, Knall, Hollauf et al. 2014). Exemplary displacement reactions include reaction of an amine with: an activated ester; an N-hydroxysuccinimide ester; an isocyanate; an isothioscyanate, an aldehyde, an epoxide, or the like.

In some embodiments, iEDDA click chemistry is used for immobilizing polypeptides to a solid support since it is rapid and delivers high yields at low input concentrations. In another embodiment, m-tetrazine rather than tetrazine is used in an iEDDA click chemistry reaction, as m-tetrazine has improved bond stability. In another embodiment, phenyl tetrazine (pTet) is used in an iEDDA click chemistry reaction.

In some embodiments, a plurality of capture nucleic acids are coupled to the solid support. In some cases, the sequence region that is complementary to the bait nucleic acid on the capture nucleic acids is the same among the plurality of capture nucleic acids. In some cases, the bait nucleic acid attached to various analytes comprises the same complementary sequence to the capture nucleic acid.

In some embodiments, the surface of the solid support is passivated (blocked). A "passivated" surface refers to a surface that has been treated with outer layer of material. Methods of passivating surfaces include standard methods from the fluorescent single molecule analysis literature, including passivating surfaces with polymer like polyethylene glycol (PEG) (Pan et al., 2015, Phys. Biol. 12:045006), polysiloxane (e.g., Pluronic F-127), star polymers (e.g., star PEG) (Groll et al., 2010, Methods Enzymol. 472:1-18), hydrophobic dichlorodimethylsilane (DDS)+self-assembled Tween-20 (Hua et al., 2014, Nat. Methods 11:1233-1236), diamond-like carbon (DLC), DLC+PEG (Stavis et al., 2011, Proc. Natl. Acad. Sci. USA 108:983-988), and zwitterionic moieties (e.g., U.S. Patent Application Publication US 2006/0183863). In addition to covalent surface modifications, a number of passivating agents can be employed as well including surfactants like Tween-20, polysiloxane in solution (Pluronic series), poly vinyl alcohol (PVA), and proteins like BSA and casein. Alternatively, density of analytes (e.g., proteins, polypeptide, or peptides) can be titrated on the surface or within the volume of a solid substrate by spiking a competitor or "dummy" reactive molecule when immobilizing the proteins, polypeptides or peptides to the solid substrate. In some embodiments, PEGs of various molecular weights can also be used for passivation from molecular weights of about 300 Da to 50 kDa or more.

In certain embodiments where multiple nucleic acid-analyte chimeras are immobilized on the same solid support, the nucleic acid-analyte chimeras can be spaced appropriately to accommodate methods of analysis to be used to assess the analytes. For example, it may be advantageous to space the nucleic acid-analyte chimeras that optimally to allow a nucleic acid-based method for assessing and sequencing the analytes to be performed. In some embodiments, the method for assessing and sequencing the analytes involve a binding agent which binds to the analyte and the binding agent comprises a coding tag with information that is transferred to a nucleic acid attached to the analyte (e.g., the bait or capture nucleic acid). In some cases, information transfer from a coding tag of a binding agent bound to one analyte may reach a neighboring analyte.

To control analyte (e.g., protein, polypeptide, or peptide spacing) or nucleic acid-analyte chimera spacing on the solid support, the density of functional coupling groups (e.g., TCO) may be titrated on the substrate surface. In some embodiments, adjacently coupled analytes or nucleic acid-analyte chimeras are spaced apart from each other on the surface or within the volume (e.g., porous supports) of a solid support at an average distance of about 50 nm to about 500 nm, or about 50 nm to about 400 nm, or about 50 nm to about 300 nm, or about 50 nm to about 200 nm, or about 50 nm to about 100 nm. In some embodiments, adjacently coupled analytes or nucleic acid-analyte chimeras are spaced apart from each other on the surface of a solid support with an average distance of at least 50 nm, at least 60 nm, at least 70 nm, at least 80 nm, at least 90 nm, at least 100 nm, at least 150 nm, at least 200 nm, at least 250 nm, at least 300 nm, at least 350 nm, at least 400 nm, at least 450 nm, or at least 500 nm. In some embodiments, adjacently coupled analytes or nucleic acid-analyte chimeras are spaced apart from each other on the surface of a solid support with an average distance of at least 50 nm. In some embodiments, adjacently coupled analytes or nucleic acid-analyte chimeras are spaced apart from each other on the surface or within the volume of a solid support such that, empirically, the relative frequency of inter- to intra-molecular events (e.g. transfer of information) is <1:10; <1:100; <1:1,000; or <1:10,000.

In some embodiments, the plurality of nucleic acid-analyte chimera is coupled on the solid support such that any adjacently coupled nucleic acid-analyte chimeras are spaced apart from each other at an average distance which ranges from about 50 to 100 nm, from about 50 to 250 nm, from about 50 to 500 nm, from about 50 to 750 nm, from about 50 to 1000 nm, from about 50 to 1500 nm, from about 50 to 2000 nm, from about 100 to 250 nm, from about 100 to 500 nm, from about 200 to 500 nm, from about 300 to 500 nm, from about 100 to 1000 nm, from about 500 to 600 nm, from about 500 to 700 nm, from about 500 to 800 nm, from about 500 to 900 nm, from about 500 to 1000 nm, from about 500 to 2000 nm, from about 500 to 5000 nm, from about 1000 to 5000 nm, or from about 3000 to 5000 nm.

In some embodiments, the spacing of the analyte on the solid support is achieved by controlling the concentration and/or number of capture nucleic acids on the solid support. In some embodiments, any adjacently coupled capture nucleic acids are spaced apart from each other on the surface or within the volume (e.g., porous supports) of a solid support at a distance of about 50 nm to about 500 nm, or about 50 nm to about 400 nm, or about 50 nm to about 300 nm, or about 50 nm to about 200 nm, or about 50 nm to about 100 nm. In some embodiments, any adjacently coupled capture nucleic acids are spaced apart from each other a on the surface of a solid support with an average distance of at least 50 nm, at least 60 nm, at least 70 nm, at least 80 nm, at least 90 nm, at least 100 nm, at least 150 nm, at least 200 nm, at least 250 nm, at least 300 nm, at least 350 nm, at least 400 nm, at least 450 nm, or at least 500 nm. In some embodiments, any adjacently coupled capture nucleic acids are spaced apart from each other on the surface of a solid support with an average distance of at least 50 nm. In some embodiments, any adjacently coupled capture nucleic acids are spaced apart from each other on the surface or within the volume of a solid support such that, empirically, the relative frequency of inter- to intra-molecular events (e.g. transfer of information) is <1:10; <1:100; <1:1,000; or <1:10,000.

A suitable spacing frequency can be determined empirically using a functional assay and can be accomplished by dilution and/or by spiking a "dummy" spacer molecule that competes for attachments sites on the substrate surface. For example, PEG-5000 (MW ~5000) is used to block the interstitial space between peptides on the substrate surface (e.g., bead surface). In addition, the peptide is coupled to a functional moiety that is also attached to a PEG-5000 molecule. In some embodiments, the functional moiety is an aldehyde, an azide/alkyne, or a malemide/thiol, or an epoxide/nucleophile, or an inverse electron demand Diels-Alder (iEDDA) group, or a moiety for a Staudinger reaction. In some embodiments, the functional moiety is an aldehyde group.

In a preferred embodiment, this is accomplished by coupling a mixture of NETS-PEG-5000-TCO+NHS-PEG-5000-Methyl to amine-derivatized beads. The stoichiometric ratio between the two PEGs (TCO vs. methyl) is titrated to generate an appropriate density of functional coupling moieties (TCO groups) on the substrate surface; the methyl-PEG is inert to coupling. The effective spacing between TCO groups can be calculated by measuring the density of TCO groups on the surface. In certain embodiments, the mean spacing between coupling moieties (e.g., TCO) on the solid surface is at least 50 nm, at least 100 nm, at least 250 nm, or at least 500 nm. After PEG5000-TCO/methyl derivatization of the beads, the excess $NH_2$ groups on the surface are quenched with a reactive anhydride (e.g. acetic or succinic anhydride).

In some embodiments, the spacing is accomplished by titrating the ratio of available attachment molecules on the substrate surface. In some examples, the substrate surface (e.g., bead surface) is functionalized with a carboxyl group (COOH) which is treated with an activating agent (e.g., activating agent is EDC and Sulfo-NHS). In some examples, the substrate surface (e.g., bead surface) comprises NHS moieties. In some embodiments, a mixture of $mPEG_n$-$NH_2$ and $NH_2$-$PEG_n$-mTet is added to the activated beads (wherein n is any number, e.g., any number from n=1 to n=100 or more). In one example, the ratio between the $mPEG_3$-$NH_2$ (not available for coupling) and $NH_2$-$PEG_4$-mTet (available for coupling) is titrated to generate an appropriate density of functional moieties available to attach the analyte on the substrate surface. In certain embodiments, the mean spacing between coupling moieties (e.g., $NH_2$-$PEG_4$-mTet) on the solid surface is at least 50 nm, at least 100 nm, at least 250 nm, or at least 500 nm. In some specific embodiments, the ratio of $NH_2$-$PEG_n$-mTet to $mPEG_n$-$NH_2$ is about or greater than 1:1000, about or greater than 1:10,000, about or greater than 1:100,000, or about or greater than 1:1,000,000. In some further embodiments, the capture nucleic acid attaches to the $NH_2$-$PEG_n$-mTet.

In some embodiments, the spacing of the analyte on the solid support is achieved by controlling the concentration and/or number of available capture nucleic acids on the solid support. In some embodiments, the spacing of the analyte on the solid support is achieved by controlling the concentration and/or number of available COOH or other functional groups on the solid support. In some specific examples, capture nucleic acids can be made unavailable by binding to bait nucleic acids that are not attached to an analyte. In some cases, the ratio of available and unavailable capture nucleic acids is titrated and determined.

II. EXEMPLARY USES OF THE PREPARED OR TREATED ANALYTE IN A PROTEIN ANALYSIS ASSAY

Provided here are methods of treating an analyte and immobilizing the analyte in formats that are compatible for analysis. For example, the prepared analyte immobilized on the solid support is in a format that is compatible with a degradation-based polypeptide sequencing assay. In some cases, the format of the nucleic acid-analyte conjugate coupled to the support is available for the addition of other macromolecules. The added macromolecules may contain information regarding the sequence of the analyte (or a portion thereof). In some examples, the added macromolecule is a nucleic acid added to the bait or capture nucleic acid. In some specific embodiments, for this purpose, the nucleic acid components of the nucleic acid-analyte conjugate coupled to the solid support is able to hold, copy, or store information.

In some embodiments, the analysis methods are for determining the sequence of at least a portion of the analyte (e.g., polypeptide or peptides). In some cases, the analysis method may include performing any of the methods as described in International Patent Publication NOs. WO 2017/192633, WO 2019/089836, WO 2019/089846, and WO 2019/089851. In some cases, the sequence of a polypeptide is analyzed by construction of an extended nucleic acid sequence which represents the polypeptide sequence, such as an extended nucleic acid onto the bait or capture nucleic acid (or any additional barcodes or tags attached thereto). In some cases, the methods provided herein for treating an analyte can apply to or be used in combination with a ProteoCode assay.

In some embodiments, it is desired that the components (nucleic acids and analytes) remain attached or immobilized and available for use in protein analysis assays that involve various chemical and/or enzymatic reactions. In some embodiments, the assay may involve multiple cycles and treatments with chemical reagents and/or enzymes.

In some embodiments, the methods provided herein for treating the analyte further comprises contacting the analyte with a binding agent capable of binding to the analyte, wherein the binding agent comprises a coding tag with identifying information regarding the binding agent; and transferring the identifying information of the coding tag to the bait nucleic acid or capture nucleic acid. In some embodiments, the transferring of the identifying information to the bait or capture nucleic acid forms an extended nucleic acid. This extended nucleic acid may also be attached to the bead (e.g., indirectly). In some cases, the method includes further steps of contacting the analyte with an additional binding agent capable of binding to the analyte, wherein the additional binding agent comprises a coding tag with identifying information regarding the additional binding agent; and transferring the identifying information of the coding tag regarding the additional binding agent to the bait nucleic acid or capture nucleic acid (or extensions thereof) that are repeated one or more times. In some examples, the transferring of the identifying information of the coding tag to the bait nucleic acid or capture nucleic acid is mediated by a ligase (e.g., DNA ligase). In some examples, the transferring of the identifying information of the coding tag to the bait nucleic acid or capture nucleic acid is mediated by a polymerase (e.g., DNA polymerase). In some examples, the transferring of the identifying information of the coding tag to the bait nucleic acid or capture nucleic acid is mediated by chemical ligation.

A. Characterization of Polypeptides Via Cyclic Rounds of Amino Acid Recognition, Information Transfer, and Amino Acid Removal In an exemplary workflow for analysis of the polypeptide analytes, the treatment and analysis of the polypeptides is as follows: a large collection of polypeptides (e.g., 50 million-1 billion or more) from a proteolytic digest are attached to bait nucleic acids to form nucleic acid-analyte chimeras, and the nucleic acid-analyte chimeras are immobilized randomly on a single molecule sequencing substrate (e.g., beads) at an appropriate intramolecular spacing. The immobilization of the peptide analytes onto the beads is performed using any of the methods described in Section I. In a cyclic manner, the terminal amino acid (e.g., N-terminal amino acid) of each peptide analyte is labeled (e.g., PTC, modified-PTC, Cbz, DNP, SNP, acetyl, guanidinyl, diheterocyclic methanimine). In some cases, the labeling of the terminal amino acid can be performed as a later step. The N-terminal amino acid (or labeled N-terminal amino acid, e.g., PITC-NTAA, Cbz-NTAA, DNP-NTAA, SNP-NTAA, acetyl-NTAA, guanidinylated-NTAA, diheterocyclic methanimine modified-NTAA) of each immobilized peptide is bound by a cognate NTAA binding agent which is attached to a coding tag, and identifying information from the coding tag associated with the bound NTAA binding agent is transferred to the bait or capture nucleic acid associated with the immobilized peptide analyte, thereby generating an extended nucleic acid containing information from the coding tag. In some embodiments, the one or more binding agents is removed or released from the polypeptides. The labeled NTAA is removed enzymatically or chemically. One or more cycles of the labeling, contacting with the binding agent, transferring identifying information, and removal of the terminal amino acid can be performed.

As described herein, the nucleic acids to which the identifying information from the coding tag is transferred to can be the bait nucleic acid, the capture nucleic acid, or a portion thereof. In some embodiments, the identifying information from the coding tag is transferred to a barcode or other nucleic acid components attached to the bait or capture nucleic acids. In some embodiments, the identifying information from the coding tag is transferred to an extended nucleic acid on the bait or capture nucleic acid which is a portion of the bait or capture nucleic acid. In some embodiments, the bait nucleic acid or the capture nucleic acid (including any additional barcodes, or other nucleic acid components attached thereto), or a portion thereof, may function as a "recording tag." The "recording tag" or the portion of the bait or capture nucleic acid which comprises a nucleic acid sequence for use as a recording tag refers to or can be a moiety, e.g., a chemical coupling moiety, a nucleic acid molecule, a polynucleotide sequence, or a sequenceable polymer molecule (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety) to which identifying information of a coding tag can be transferred. A recording tag may comprise DNA, RNA, or polynucleotide analogs including PNA, gPNA, GNA, HNA, BNA, XNA, TNA, or a combination thereof. The identifying information of a coding tag may be transferred to a bait or capture nucleic acid that also contains other nucleic acid components. Identifying information can comprise any information characterizing a molecule such as information pertaining to identity, sample, fraction, partition, spatial location, interacting neighboring molecule(s), cycle number, etc. Additionally, the presence of UMI information can also be classified as identifying information. In certain embodiments, after a binding agent binds to a polypeptide, information from a coding tag linked to a binding agent can be transferred to the bait or capture nucleic acid (or a portion thereof) associated with the polypeptide while the binding agent is bound to the polypeptide. In other embodiments, after a binding agent binds to a polypeptide, information from a recording tag associated with the polypeptide can be transferred to the coding tag linked to the binding agent while the binding agent is bound to the polypeptide. In some embodiment, the identifying information of a coding tag is transferred to the 3'-end of the bait or capture nucleic acid in embodiments where polymerase extension is used to transfer coding tag information.

The coding tag associated with the binding agent is or comprises a polynucleotide with any suitable length, e.g., a nucleic acid molecule of about 2 bases to about 100 bases, including any integer including 2 and 100 and in between, that comprises identifying information for its associated binding agent. A "coding tag" may also be made from a "sequenceable polymer" (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety). A coding tag may comprise an encoder sequence or a sequence with identifying information, which is optionally flanked by one spacer on one side or optionally flanked by a spacer on each side. A coding tag may also be comprised of an optional UMI and/or an optional binding cycle-specific barcode. A coding tag may be single stranded or double stranded. A double stranded coding tag may comprise blunt ends, overhanging ends, or both. A coding tag may refer to the coding tag that is directly attached to a binding agent, to a complementary sequence hybridized to the coding tag directly attached to a binding agent (e.g., for double stranded coding tags), or to coding tag information present in an extended nucleic acid on the bait or capture nucleic acid. In certain embodiments, a coding tag may further comprise a binding cycle specific spacer or barcode, a unique molecular identifier, a universal priming site, or any combination thereof.

In some embodiments, the order of the steps in the process for a degradation-based peptide or polypeptide sequencing assay can be reversed or be performed in various orders. For example, in some embodiments, the terminal amino acid labeling can be conducted before and/or after the polypeptide is bound to the binding agent.

In some embodiments, the identifying information from the coding tag comprises information regarding the identity of the amino acid on the analyte bound by the binding agent.

In some examples, the final extended nucleic acid (bait or capture nucleic acid including any additional barcodes attached thereto) containing information from one or more binding agents is optionally flanked by sequences (e.g., adaptor sequences and/or universal priming sites) to facilitate downstream amplification and/or DNA sequencing. The forward universal priming site (e.g., Illumina's P5-S1 sequence) can be part of the original design of the bait or capture nucleic acid and the reverse universal priming site (e.g., Illumina's P7-S2' sequence) can be added as a final step in the extension of the nucleic acid. In some embodiments, the universal priming sites used include any of the sequences set forth in SEQ ID NO: 1, 2, 32, and 33. In some embodiments, the addition of forward and reverse priming sites can be done independently of a binding agent.

In the methods described herein, upon binding of a binding agent to a polypeptide analyte, identifying information of its linked coding tag is transferred to a nucleic acid associated with the polypeptide analyte, thereby generating an extended nucleic acid. The nucleic acid associated with the polypeptide analyte can be the bait nucleic acid or capture nucleic acid as described in Section I. In some embodiments, the bait nucleic acid or capture nucleic acid further comprises barcodes and/or other nucleic acid components. In particular embodiments, the identifying information from the coding tag of the binding agent is transferred to the bait nucleic acid or capture nucleic acid or added to any existing barcodes (or other nucleic acid components) attached thereto. The transfer of the identifying information of the coding tag to the nucleic acid associated with the analyte may be performed using extension or ligation. In some embodiments, a spacer is added to the end of the capture or bait nucleic acid, and the spacer comprises a sequence that is capable of hybridizing with a sequence on the coding tag to facilitate transfer of the identifying information.

The bait or capture nucleic acid, or a part thereof, configured to be used as a recording tag can be a moiety, e.g., a chemical coupling moiety, a nucleic acid molecule, or a sequenceable polymer molecule (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety) to which identifying information of a coding tag can be transferred, or from which identifying information about the macromolecule (e.g., UMI information) associated with the recording tag can be transferred to the coding tag. In certain embodiments, after a binding agent binds a polypeptide, information from a coding tag linked to a binding agent can be transferred to the nucleic acid associated with the polypeptide while the binding agent is bound to the polypeptide.

An extended nucleic acid associated with the analyte with identifying information from the coding tag may comprise information from a binding agent's coding tag representing each binding cycle performed. However, in some cases, an extended nucleic acid may also experience a "missed" binding cycle, e.g., if a binding agent fails to bind to the polypeptide analyte, because the coding tag was missing, damaged, or defective, because the primer extension reaction failed. Even if a binding event occurs, transfer of information from the coding tag may be incomplete or less than 100% accurate, e.g., because a coding tag was damaged or defective, because errors were introduced in the primer extension reaction). Thus, an extended nucleic acid may represent 100%, or up to 95%, 90%, 85%, 80%, 75%, 70%, 65%, 60%, 65%, 55%, 50%, 45%, 40%, 35%, 30%, or any subrange thereof, of binding events that have occurred on its associated polypeptide. Moreover, the coding tag information present in the extended nucleic acid may have at least 30%, 35%, 40%, 45%, 50%, 55%, 60%, 65%, 70%, 75%, 80%, 85%, 90%, 95%, or 100% identity the corresponding coding tags.

In certain embodiments, an extended nucleic acid on the bait or capture nucleic acid associated with the immobilized peptide analyte may comprise information from multiple coding tags representing multiple, successive binding events. In these embodiments, a single, concatenated extended nucleic acid on the bait or capture nucleic acid associated with the immobilized peptide analyte can be representative of a single polypeptide. As referred to herein, transfer of coding tag information to the bait or capture nucleic acid associated with the immobilized peptide analyte also includes transfer to an extended nucleic acid on the bait or capture nucleic acid as would occur in methods involving multiple, successive binding events.

In certain embodiments, the binding event information is transferred from a coding tag to the bait or capture nucleic acid associated with the immobilized peptide analyte in a cyclic fashion. Cross-reactive binding events can be informatically filtered out after sequencing by requiring that at least two different coding tags, identifying two or more independent binding events, map to the same class of binding agents (cognate to a particular protein). The coding tag may contain an optional UMI sequence in addition to one or more spacer sequences. Universal priming sequences may also be included in extended nucleic acids on the bait or capture nucleic acid associated with the immobilized peptide analyte for amplification and NGS sequencing.

Coding tag information associated with a specific binding agent may be transferred using a variety of methods. In certain embodiments, information of a coding tag is transferred to a nucleic acid on the bait or capture nucleic acid associated with the immobilized peptide analyte via primer extension (Chan et al., 2015, Curr Opin Chem Biol. 26: 55-61). A spacer sequence on the 3'-terminus of a bait or capture nucleic acid or an nucleic acid attached to the bait or capture nucleic acid anneals with complementary spacer sequence on the 3' terminus of a coding tag and a polymerase (e.g., strand-displacing polymerase) extends the nucleic acid sequence on the bait or capture nucleic acid, using the annealed coding tag as a template. In some embodiments, oligonucleotides complementary to coding tag encoder sequence and 5' spacer can be pre-annealed to the coding tags to prevent hybridization of the coding tag to internal encoder and spacer sequences present in an extended nucleic acid. The 3' terminal spacer, on the coding tag, remaining single stranded, preferably binds to the terminal 3' spacer on the bait or capture nucleic acids (or any barcodes or other nucleic acid components). In other embodiments, a nascent nucleic acid on the bait or capture nucleic acid associated with the immobilized peptide analyte can be coated with a single stranded binding protein to prevent annealing of the coding tag to internal sites. Alternatively, the nascent nucleic acid can also be coated with RecA (or related homologues such as uvsX) to facilitate invasion of the 3' terminus into a completely double stranded coding tag (Bell et al., 2012, Nature 491:274-278). This configuration prevents the double stranded coding tag from interacting with internal nucleic acid elements on the bait or capture nucleic acid associated with the immobilized peptide analyte, yet is susceptible to strand invasion by the RecA coated 3' tail of the extended nucleic acid (Bell, et al., 2015, Elife 4: e08646). The presence of a single-stranded binding protein can facilitate the strand displacement reaction.

In some embodiments, a DNA polymerase that is used for primer extension possesses strand-displacement activity and has limited or is devoid of 3'-5 exonuclease activity. Several of many examples of such polymerases include Klenow exo- (Klenow fragment of DNA Pol 1), T4 DNA polymerase exo-, T7 DNA polymerase exo (Sequenase 2.0), Pfu exo-, Vent exo-, Deep Vent exo-, Bst DNA polymerase large fragment exo-, Bca Pol, 9° N Pol, and Phi29 Pol exo-. In a preferred embodiment, the DNA polymerase is active at room temperature and up to 45° C. In another embodiment, a "warm start" version of a thermophilic polymerase is employed such that the polymerase is activated and is used at about 40° C.-50° C. An exemplary warm start polymerase is Bst 2.0 Warm Start DNA Polymerase (New England Biolabs).

Additives useful in strand-displacement replication include any of a number of single-stranded DNA binding proteins (SSB proteins) of bacterial, viral, or eukaryotic origin, such as SSB protein of E. coli, phage T4 gene 32 product, phage T7 gene 2.5 protein, phage Pf3 SSB, replication protein A RPA32 and RPA14 subunits (Wold, 1997); other DNA binding proteins, such as adenovirus DNA-binding protein, herpes simplex protein ICP8, BMRF1 polymerase accessory subunit, herpes virus UL29 SSB-like protein; any of a number of replication complex proteins known to participate in DNA replication, such as phage T7 helicase/primase, phage T4 gene 41 helicase, E. coli Rep helicase, E. coli recBCD helicase, recA, E. coli and eukaryotic topoisomerases (Annu Rev Biochem. (2001) 70:369-413).

Mis-priming or self-priming events, such as when the terminal spacer sequence of the recoding tag primes extension self-extension may be minimized by inclusion of single stranded binding proteins (T4 gene 32, E. coli SSB, etc.), DMSO (1-10%), formamide (1-10%), BSA (10-100 ug/ml), TMAC1 (1-5 mM), ammonium sulfate (10-50 mM), betaine (1-3 M), glycerol (5-40%), or ethylene glycol (5-40%), in the primer extension reaction.

Most type A polymerases are devoid of 3' exonuclease activity (endogenous or engineered removal), such as Klenow exo-, T7 DNA polymerase exo- (Sequenase 2.0), and Taq polymerase catalyzes non-templated addition of a nucleotide, preferably an adenosine base (to lesser degree a G base, dependent on sequence context) to the 3' blunt end of a duplex amplification product. For Taq polymerase, a 3' pyrimidine (C>T) minimizes non-templated adenosine addition, whereas a 3' purine nucleotide (G>A) favours non-templated adenosine addition. In some embodiments, using Taq polymerase for primer extension, placement of a thymidine base in the coding tag between the spacer sequence distal from the binding agent and the adjacent barcode sequence (e.g., encoder sequence or cycle specific sequence) accommodates the sporadic inclusion of a non-templated adenosine nucleotide on the 3' terminus of the spacer sequence of the bait or capture nucleic acid. In this manner, the extended nucleic acid on the bait or capture nucleic acid associated with the immobilized peptide analyte (with or without a non-templated adenosine base) can anneal to the coding tag and undergo primer extension.

Alternatively, addition of non-templated base can be reduced by employing a mutant polymerase (mesophilic or thermophilic) in which non-templated terminal transferase activity has been greatly reduced by one or more point mutations, especially in the 0-helix region (see U.S. Pat. No. 7,501,237) (Yang et al., Nucleic Acids Res. (2002) 30(19): 4314-4320). Pfu exo-, which is 3' exonuclease deficient and has strand-displacing ability, also does not have non-templated terminal transferase activity.

In another embodiment, polymerase extension buffers are comprised of 40-120 mM buffering agent such as Tris-Acetate, Tris-HCl, HEPES, etc. at a pH of 6-9.

Self-priming/mis-priming events initiated by self-annealing of the terminal spacer sequence of the extended nucleic acid with internal regions of the extended nucleic acid may be minimized by including pseudo-complementary bases in the nucleic acid on the bait or capture nucleic acid (or extended nucleic acids attached) (Lahoud et al., Nucleic Acids Res. (2008) 36:3409-3419), (Hoshika et al., Angew Chem Int Ed Engl (2010) 49(32): 5554-5557). Pseudo-complementary bases show significantly reduced hybridization affinities for the formation of duplexes with each other due the presence of chemical modification. However, many pseudo-complementary modified bases can form strong base pairs with natural DNA or RNA sequences.

In certain embodiments, the coding tag spacer sequence is comprised of multiple A and T bases, and commercially available pseudo-complementary bases 2-aminoadenine and 2-thiothymine are incorporated in the bait or capture nucleic acids using phosphoramidite oligonucleotide synthesis. Additional pseudocomplementary bases can be incorporated into the extended nucleic during primer extension by adding pseudo-complementary nucleotides to the reaction (Gamper et al., Biochemistry. (2006) 45(22):6978-86).

In some embodiments, to minimize non-specific interaction of the coding tag labeled binding agents in solution with the nucleic acids of immobilized protein analytes, competitor (also referred to as blocking) oligonucleotides complementary to nucleic acids containing spacer sequences (e.g., on the bait or capture nucleic acids or extensions thereof) can be added to binding reactions to minimize non-specific interactions. In some embodiments, the blocking oligonucleotide contains a sequence that is complementary to the coding tag attached to the binding agent or a portion thereof. For example, the blocking oligonucleotide contains a sequence that is complementary to a spacer and/or barcode sequence of the coding tag. In some embodiments, blocking oligonucleotides are relatively short. Excess competitor oligonucleotides are washed from the binding reaction prior to primer extension, which effectively dissociates the annealed competitor oligonucleotides from the nucleic acids on the bait or capture nucleic acid, especially when exposed to slightly elevated temperatures (e.g., 30-50° C.). Blocking oligonucleotides may comprise a terminator nucleotide at its 3' end to prevent primer extension.

In certain embodiments, the annealing of the spacer sequence on the bait or capture nucleic acid to the complementary spacer sequence on the coding tag is metastable under the primer extension reaction conditions (i.e., the annealing Tm is similar to the reaction temperature). This allows the spacer sequence of the coding tag to displace any blocking oligonucleotide annealed to the spacer sequence of the bait or capture nucleic acid (or extensions thereof).

Coding tag information associated with a specific binding agent may also be transferred to a nucleic acid on the bait or capture nucleic acid associated with the immobilized peptide analyte via ligation. Ligation may be a blunt end ligation or sticky end ligation. Ligation may be an enzymatic ligation reaction. Examples of ligases include, but are not limited to CV DNA ligase, T4 DNA ligase, T7 DNA ligase, T3 DNA ligase, Taq DNA ligase, E. coli DNA ligase, 9° N DNA ligase, Electroligase® (See e.g., U.S. Patent Publication No. US20140378315). Alternatively, a ligation may be a chemical ligation reaction. In some embodiments as illustrated in International Patent Publication No. WO 2017/192633, a spacer-less ligation is accomplished by using hybridization of a "recording helper" sequence with an arm on the coding tag. The annealed complement sequences are chemically ligated using standard chemical ligation or "click chemistry" (Gunderson et al., Genome Res (1998) 8(11): 1142-1153; Peng et al., European J Org Chem (2010) (22): 4194-4197; El-Sagheer et al., Proc Natl Acad Sci USA (2011) 108(28): 11338-11343; El-Sagheer et al., Org Biomol Chem (2011) 9(1): 232-235; Sharma et al., Anal Chem (2012) 84(14): 6104-6109; Roloff et al., Bioorg Med Chem (2013) 21(12): 3458-3464; Litovchick et al., Artif DNA PNA XNA (2014) 5(1): e27896; Roloff et al., Methods Mol Biol (2014) 1050: 131-141).

In another embodiment, transfer of PNAs can be accomplished with chemical ligation using published techniques. The structure of PNA is such that it has a 5' N-terminal amine group and an unreactive 3' C-terminal amide. Chemical ligation of PNA requires that the termini be modified to be chemically active. This is typically done by derivatizing the 5' N-terminus with a cysteinyl moiety and the 3' C-terminus with a thioester moiety. Such modified PNAs easily couple using standard native chemical ligation conditions (Roloff et al., (2013) Bioorgan. Med. Chem. 21:3458-3464).

In some embodiments, coding tag information can be transferred using topoisomerase. Topoisomerase can be used be used to ligate a topo-charged 3' phosphate on the bait or capture nucleic acid (or extensions thereof or any nucleic acids attached) to the 5' end of the coding tag, or complement thereof (Shuman et al., 1994, J. Biol. Chem. 269: 32678-32684).

As described herein, a binding agent may bind to a post-translationally modified amino acid. Thus, in certain embodiments, an extended nucleic acid associated with the analyte comprises coding tag information relating to amino acid sequence and post-translational modifications of the polypeptide analyte. In some embodiments, detection of internal post-translationally modified amino acids (e.g., phosphorylation, glycosylation, succinylation, ubiquitination, S-Nitrosylation, methylation, N-acetylation, lipidation, etc.) is be accomplished prior to detection and elimination of terminal amino acids (e.g., NTAA or CTAA). In one example, a peptide is contacted with binding agents for PTM modifications, and associated coding tag information are transferred to the nucleic acid on the bait or capture nucleic acid associated with the immobilized peptide analyte. Once the detection and transfer of coding tag information relating to amino acid modifications is complete, the PTM modifying groups can be removed before detection and transfer of coding tag information for the primary amino acid sequence using N-terminal or C-terminal degradation methods. Thus, resulting extended nucleic acids indicate the presence of post-translational modifications in a peptide sequence, though not the sequential order, along with primary amino acid sequence information.

In some embodiments, detection of internal post-translationally modified amino acids may occur concurrently with detection of primary amino acid sequence. In one example, an NTAA (or CTAA) is contacted with a binding agent specific for a post-translationally modified amino acid, either alone or as part of a library of binding agents (e.g., library composed of binding agents for the 20 standard amino acids and selected post-translational modified amino acids). Successive cycles of terminal amino acid elimination and contact with a binding agent (or library of binding agents) follow. Thus, resulting extended nucleic acids on the bait or capture nucleic acid associated with the immobilized peptide analyte indicate the presence and order of post-translational modifications in the context of a primary amino acid sequence.

In certain embodiments, an ensemble of nucleic acids on the bait or capture nucleic acid may be employed per polypeptide to improve the overall robustness and efficiency of coding tag information transfer. The use of an ensemble of nucleic acids associated with a given polypeptide rather than a single nucleic acid may improve the efficiency of library construction.

For embodiments involving analysis of denatured analytes including proteins, polypeptides, and peptides, the bound binding agent and annealed coding tag can be removed following transfer of the identifying information (e.g., primer extension) by using highly denaturing conditions (e.g., 0.1-0.2 N NaOH, 6M Urea, 2.4 M guanidinium isothiocyanate, 95% formamide, etc.).

In certain embodiments relating to analyzing peptides, following binding of a binding agent and transfer of coding tag information, the terminal amino acid is removed or cleaved from the peptide to expose a new terminal amino acid. In some embodiments, the terminal amino acid is an NTAA. In other embodiments, the terminal amino acid is a CTAA. Cleavage of a terminal amino acid can be accomplished by any number of known techniques, including chemical cleavage and enzymatic cleavage.

In some embodiments, an engineered enzyme that catalyzes or reagent that promotes the removal of the modified or labeled N-terminal amino acid is used. In some embodiments, the terminal amino acid is removed or eliminated using any of the methods as described in International Patent Publication No. WO 2019/089846 or U.S. provisional patent application No. 62/841,171. In some embodiments, cleavage of a terminal amino uses a carboxypeptidase, an aminopeptidase, a dipeptidyl peptidase, a dipeptidyl aminopeptidase or a variant, mutant, or modified protein thereof; a hydrolase or a variant, mutant, or modified protein thereof; a mild Edman degradation reagent; an Edmanase enzyme; anhydrous TFA, a base; or any combination thereof.

In some embodiments, the mild Edman degradation uses a dichloro or monochloro acid; the mild Edman degradation uses TFA, TCA, or DCA; or the mild Edman degradation uses triethylamine, triethanolamine, or triethylammonium acetate ($Et_3NHOAc$). In some cases, the reagent for removing the amino acid comprises a base. In some embodiments, the base is a hydroxide, an alkylated amine, a cyclic amine, a carbonate buffer, trisodium phosphate buffer, or a metal salt. In some examples, the hydroxide is sodium hydroxide; the alkylated amine is selected from methylamine, ethylamine, propylamine, dimethylamine, diethylamine, dipropylamine, trimethylamine, triethylamine, tripropylamine, cyclohexylamine, benzylamine, aniline, diphenylamine, N,N-Diisopropylethylamine (DIPEA), and lithium diisopropylamide (LDA); the cyclic amine is selected from pyridine, pyrimidine, imidazole, pyrrole, indole, piperidine, prolidine, 1,8-diazabicyclo[5.4.0]undec-7-ene (DBU), and 1,5-diazabicyclo[4.3.0]non-5-ene (DBN); the carbonate buffer comprises sodium carbonate, potassium carbonate, calcium carbonate, sodium bicarbonate, potassium bicarbonate, or calcium bicarbonate; the metal salt comprises silver; or the metal salt is $AgClO_4$.

In some cases, enzymatic cleavage of a NTAA may be accomplished by an aminopeptidase or other peptidases. Aminopeptidases naturally occur as monomeric and multimeric enzymes, and may be metal or ATP-dependent. Natural aminopeptidases have very limited specificity, and generically cleave N-terminal amino acids in a processive manner, cleaving one amino acid off after another. For the methods described here, aminopeptidases (e.g., metalloenzymatic aminopeptidase) may be engineered to possess specific binding or catalytic activity to the NTAA only when modified with an N-terminal label. For example, an aminopeptidase may be engineered such than it only cleaves an N-terminal amino acid if it is modified by a group such as PTC, modified-PTC, Cbz, DNP, SNP, acetyl, guanidinyl, diheterocyclic methanimine, etc. In this way, the aminopeptidase cleaves only a single amino acid at a time from the N-terminus, and allows control of the degradation cycle. In some embodiments, the modified aminopeptidase is non-selective as to amino acid residue identity while being selective for the N-terminal label. In other embodiments, the modified aminopeptidase is selective for both amino acid residue identity and the N-terminal label.

In some embodiments, the method further comprises contacting the polypeptide with a proline aminopeptidase under conditions suitable to cleave an N-terminal proline before step (b). In some examples, a proline aminopeptidase (PAP) is an enzyme that is capable of specifically cleaving an N-terminal proline from a polypeptide. PAP enzymes that cleave N-terminal prolines are also referred to as proline iminopeptidases (PIPs). Known monomeric PAPs include family members from *B. coagulans, L. delbrueckii, N. gonorrhoeae, F. meningosepticum, S. marcescens, T. acidophilum, L. plantarum* (MEROPS 533.001) Nakajima et al., J Bacteriol. (2006) 188(4):1599-606; Kitazono et al., Bacteriol (1992) 174(24):7919-7925). Known multimeric PAPs include *D. hansenii* (Bolumar et al., (2003) 86(1-2): 141-151) and similar homologues from other species (Basten et al., Mol Genet Genomics (2005) 272(6):673-679). Either native or engineered variants/mutants of PAPs may be employed.

For embodiments relating to CTAA binding agents, methods of cleaving CTAA from peptides are also known in the art. For example, U.S. Pat. No. 6,046,053 discloses a method of reacting the peptide or protein with an alkyl acid anhydride to convert the carboxy-terminal into oxazolone, liberating the C-terminal amino acid by reaction with acid and alcohol or with ester. Enzymatic cleavage of a CTAA may also be accomplished by a carboxypeptidase. Several carboxypeptidases exhibit amino acid preferences, e.g., carboxypeptidase B preferentially cleaves at basic amino acids, such as arginine and lysine. As described above, carboxypeptidases may also be modified in the same fashion as aminopeptidases to engineer carboxypeptidases that specifically bind to CTAAs having a C-terminal label. In this way, the carboxypeptidase cleaves only a single amino acid at a time from the C-terminus, and allows control of the degradation cycle. In some embodiments, the modified carboxypeptidase is non-selective as to amino acid residue identity while being selective for the C-terminal label. In other embodiments, the modified carboxypeptidase is selective for both amino acid residue identity and the C-terminal label.

B. Binding Agents for Amino Acid Recognition

In certain embodiments, the methods for analyzing a polypeptide provided in the present disclosure comprise multiple binding cycles, where the polypeptide analyte is contacted with a plurality of binding agents, and successive binding of binding agents transfers historical binding information in the form of a nucleic acid based coding tag to at least one nucleic acid (e.g., bait or capture nucleic acid) associated with the polypeptide. In this way, a historical record containing information about multiple binding events is generated in a nucleic acid format.

In some embodiments, a binding agent may be a cognate binding agent of the analyte or any portion of the analyte. In certain embodiments, a binding agent may bind to an epitope, an NTAA, a CTAA, an intervening amino acid, dipeptide (sequence of two amino acids), tripeptide (sequence of three amino acids), or higher order peptide of a peptide molecule. In some embodiments, each binding agent in a library of binding agents selectively binds to a particular amino acid, for example one of the twenty standard naturally occurring amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). In some embodiments, the binding agent binds to an unmodified or native amino acid. In some examples, the binding agent binds to an unmodified or native dipeptide (sequence of two amino acids), tripeptide (sequence of three amino acids), or higher order peptide of a peptide molecule. A binding agent may be engineered for high affinity for a native or unmodified NTAA, high specificity for a native or unmodified NTAA, or both. In some embodiments, binding agents can be developed through directed evolution of promising affinity scaffolds using phage display.

A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may bind to an N-terminal or C-terminal diamino acid moiety. A binding agent may preferably bind to a chemically modified or labeled amino acid. For example, a binding agent may preferably bind to an amino acid that has been functionalized with an acetyl moiety, Cbz moiety, guanyl moiety, dansyl moiety, PTC moiety, DNP moiety, SNP moiety, heterocyclic methanimine moiety, etc., over an amino acid that does not possess said moiety. A modified or labeled NTAA can be one that is functionalized with phenylisothiocyanate, PITC, 1-fluoro-2,4-dinitrobenzene (Sanger's reagent, DNFB), benzyloxycarbonyl chloride or carbobenzoxy chloride (Cbz-Cl), N-(Benzyloxycarbonyloxy)succinimide (Cbz-OSu or Cbz-O-NHS), dansyl chloride (DNS-Cl, or 1-dimethylaminonaphthalene-5-sulfonyl chloride), 4-sulfonyl-2-nitrofluorobenzene (SNFB), N-Acetyl-Isatoic Anhydride, Isatoic Anhydride, 2-Pyridinecarboxaldehyde, 2-Formylphenylboronic acid, 2-Acetylphenylboronic acid, 1-Fluoro-2,4-dinitrobenzene, Succinic anhydride, 4-Chloro-7-nitrobenzofurazan, Pentafluorophenylisothiocyanate, 4-(Trifluoromethoxy)-phenylisothiocyanate, 4-(Trifluoromethyl)-phenylisothiocyanate, 3-(Carboxylic acid)-phenylisothiocyanate, 3-(Trifluoromethyl)-phenylisothiocyanate, 1-Naphthylisothiocyanate, N-nitroimidazole-1-carboximidamide, N,N,Ä≤-Bis(pivaloyl)-1H-pyrazole-1-carboxamidine, N,N,Ä≤-Bis(benzyloxycarbonyl)-1H-pyrazole-1-carboxamidine, an acetylating reagent, a guanidinylation reagent, a thioacylation reagent, a thioacetylation reagent, or a thiobenzylation reagent, or a diheterocyclic methanimine reagent. In some examples, the binding agent binds to an amino acid labeled by contacting with a reagent or using a method as described in International Patent Publication No. WO 2019/089846 or U.S. provisional patent application No. 62/841,171. In some cases, the binding agent binds to an amino acid labeled by an amine modifying reagent.

In some embodiments, the binding agent is partially specific or selective. In some aspects, the binding agent preferentially binds to one or more amino acids. For example, a binding agent may preferentially bind to the amino acids A, C, and G over other amino acids. In some other examples, the binding agent may selectively or specifically bind to more than one amino acid. In some aspects, the binding agent may also have a preference for one or more amino acids at the second, third, fourth, fifth, etc. positions from the terminal amino acid. In some cases, the binding agent preferentially binds to a specific terminal amino acid and one or more penultimate amino acid. In some cases, the binding agent preferentially binds to one or more specific terminal amino acid(s) and one penultimate amino acid. For example, a binding agent may preferentially bind to AA, AC, and AG or a binding agent may preferentially bind to AA, CA, and GA. In some specific examples, binding agents with different specificities can share the same coding tag.

In certain embodiments, the concentration of the binding agents in a solution is controlled to reduce background and/or false positive results of the assay.

In some embodiments, the concentration of a binding agent can be at any suitable concentration, e.g., at about 0.0001 nM, about 0.001 nM, about 0.01 nM, about 0.1 nM, about 1 nM, about 2 nM, about 5 nM, about 10 nM, about 20 nM, about 50 nM, about 100 nM, about 200 nM, about 500 nM, or about 1000 nM. In other embodiments, the concentration of a soluble conjugate used in the assay is between about 0.0001 nM and about 0.001 nM, between about 0.001 nM and about 0.01 nM, between about 0.01 nM and about 0.1 nM, between about 0.1 nM and about 1 nM, between about 1 nM and about 2 nM, between about 2 nM and about 5 nM, between about 5 nM and about 10 nM, between about 10 nM and about 20 nM, between about 20 nM and about 50 nM, between about 50 nM and about 100 nM, between about 100 nM and about 200 nM, between about 200 nM and about 500 nM, between about 500 nM and about 1000 nM, or more than about 1000 nM.

In some embodiments, the ratio between the soluble binding agent molecules and the immobilized polypeptides and/or the nucleic acids (e.g., of the nucleic acid-analyte conjugate) can be at any suitable range, e.g., at about 0.00001:1, about 0.0001:1, about 0.001:1, about 0.01:1, about 0.1:1, about 1:1, about 2:1, about 5:1, about 10:1, about 15:1, about 20:1, about 25:1, about 30:1, about 35:1, about 40:1, about 45:1, about 50:1, about 55:1, about 60:1, about 65:1, about 70:1, about 75:1, about 80:1, about 85:1, about 90:1, about 95:1, about 100:1, about $10^4$:1, about $10^5$:1, about $10^6$:1, or higher, or any ratio in between the above listed ratios. Higher ratios between the soluble binding agent molecules and the immobilized polypeptide(s) and/or the nucleic acids (e.g., of the nucleic acid-analyte conjugate) can be used to drive the binding and/or the coding tag information transfer to completion. This may be particularly useful for detecting and/or analyzing low abundance polypeptides in a sample.

In certain embodiments, a binding agent has a $K_d$ of or less than about 500 nM, of or less than about 200 nM, of or less than about 100 nM, of or less than about 50 nM, of or less than about 10 nM, of or less than about 5 nM, of or less than about 1 nM, of or less than about 0.5 nM, or of or less than about 0.1 nM. In a particular embodiment, the binding agent is added to the macromolecule at a concentration >10×, >100×, or >1000× its $K_d$ to drive binding to completion. In particular, a high binding affinity with a low off-rate may be efficacious for information transfer between the coding tag and recording tag.

In embodiments relating to methods of analyzing peptides or polypeptides using an N-terminal degradation based approach, following contacting and binding of a first binding agent to an n NTAA of a peptide of n amino acids and transfer of the first binding agent's coding tag information to a nucleic acid associated with the peptide, thereby generating a first order extended nucleic acid (e.g., on the bait or capture nucleic acid), the n NTAA is eliminated as described herein. Removal of the n labeled NTAA by contacting with an enzyme or chemical reagents converts the n-1 amino acid of the peptide to an N-terminal amino acid, which is referred to herein as an n-1 NTAA. A second binding agent is contacted with the peptide and binds to the n-1 NTAA, and the second binding agent's coding tag information is transferred to the first order extended nucleic acid thereby generating a second order extended nucleic acid (e.g., for generating a concatenated $n^{th}$ order extended nucleic acid representing the peptide). Elimination of the n-1 labeled NTAA converts the n-2 amino acid of the peptide to an N-terminal amino acid, which is referred to herein as n-2 NTAA. Additional binding, transfer, labeling, and removal, can occur as described above up to n amino acids to generate an $n^{th}$ order extended nucleic acid or n separate extended nucleic acids, which collectively represent the peptide. As used herein, an n "order" when used in reference to a binding agent, coding tag, or extended nucleic acid, refers to the n binding cycle, wherein the binding agent and its associated coding tag is used or the n binding cycle where the extended nucleic acid is created (e.g. on the bait or capture nucleic acid). In some embodiments, steps including the NTAA in the described exemplary approach can be performed instead with a C terminal amino acid (CTAA).

In some embodiments, contacting of the first binding agent and second binding agent to the polypeptide analyte, and optionally any further binding agents (e.g., third binding agent, fourth binding agent, fifth binding agent, and so on), are performed at the same time. For example, the first binding agent and second binding agent, and optionally any further order binding agents, can be pooled together, for example to form a library of binding agents. In another example, the first binding agent and second binding agent, and optionally any further order binding agents, rather than being pooled together, are added simultaneously to the polypeptide. In one embodiment, a library of binding agents comprises at least 20 binding agents that selectively bind to the 20 standard, naturally occurring amino acids. In some embodiments, a library of binding agents may comprise binding agents that selectively bind to the modified amino acids.

In other embodiments, the first binding agent and second binding agent, and optionally any further order binding agents, are each contacted with the polypeptide in separate binding cycles, added in sequential order. In certain embodiments, multiple binding agents are used at the same time, in parallel. This parallel approach saves time and reduces non-specific binding by non-cognate binding agents to a site that is bound by a cognate binding agent (because the binding agents are in competition).

The length of the final extended nucleic acids (e.g., on the bait or capture nucleic acid) generated by the methods described herein is dependent upon multiple factors, including the length of the coding tag (e.g., encoder sequence and spacer), the length of the nucleic acids (e.g., on the bait or capture nucleic acid, optionally including any unique molecular identifier, spacer, universal priming site, barcode, or combinations thereof), the number of binding cycles performed, and whether coding tags from each binding cycle are transferred to the same extended nucleic acid or to multiple extended nucleic acids. In some examples, if the coding tag has an encoder sequence of 5 bases that is flanked on each side by a spacer of 5 bases, the coding tag information on the final extended nucleic acid, which represents the peptide's binding agent history, is 10 bases×number of cycles.

After the final binding cycle and transfer of the final binding agent's coding tag information to the extended nucleic acid (e.g., on the bait or capture nucleic acid), the tag can be capped by addition of a universal reverse priming site via ligation, primer extension or other methods known in the art. In some embodiments, the universal forward priming site in the nucleic acid (e.g., on the bait or capture nucleic acid) is compatible with the universal reverse priming site that is appended to the final extended nucleic acid. In some embodiments, after the final transfer to the extended nucleic acid, a capping barcode may be introduced with the addition of the universal reverse priming site. In some cases, an optional UMI may be added to the extended nucleic acid. In some embodiments, a universal reverse priming site is an Illumina P7 primer (5'-CAAGCAGAAGACGGCAT-ACGAGAT-3'-SEQ ID NO:2) or an Illumina P5 primer (5'-AATGATACGGCGACCACCGA-3'-SEQ ID NO:1) or a sequence set forth in SEQ ID NO: 32 or 33. The sense or antisense P7 may be appended, depending on strand sense of the nucleic acid to which the identifying information from the coding tag is transferred to. An extended nucleic acid library can be cleaved or amplified directly from the solid support (e.g., beads) and used in traditional next generation sequencing assays and protocols.

In some embodiments, a primer extension reaction is performed on a library of single stranded extended nucleic acids (e.g., extended on the bait or capture nucleic acid) to copy complementary strands thereof. In some embodiments, the peptide sequencing assay (e.g., ProteoCode assay), comprises several chemical and enzymatic steps in a cyclical progression. In some cases, one advantage of a single molecule assay is the robustness to inefficiencies in the various cyclical chemical/enzymatic steps. In some embodiments, the use of cycle-specific barcodes present in the coding tag sequence allows an advantage to the assay.

C. Processing and Analysis of Tags

Extended nucleic acids associated with the analyte with identifying information from one or more coding tags and any other tags (barcodes, UMI, etc.) representing the polypeptide(s) of interest can be processed and analysed using a variety of nucleic acid sequencing methods. In some embodiments, the method includes analyzing the identifying information regarding the binding agent transferred to the bait nucleic acid or the capture nucleic acid. Examples of sequencing methods include, but are not limited to, chain termination sequencing (Sanger sequencing); next generation sequencing methods, such as sequencing by synthesis, sequencing by ligation, sequencing by hybridization, polony sequencing, ion semiconductor sequencing, and pyrosequencing; and third generation sequencing methods, such as single molecule real time sequencing, nanopore-based sequencing, duplex interrupted sequencing, and direct imaging of DNA using advanced microscopy.

Suitable sequencing methods for use in the invention include, but are not limited to, sequencing by hybridization, sequencing by synthesis technology (e.g., HiSeg™ and Solexa™, Illumina), SMRT™ (Single Molecule Real Time) technology (Pacific Biosciences), true single molecule sequencing (e.g., HeliScope™, Helicos Biosciences), massively parallel next generation sequencing (e.g., SOLiD™, Applied Biosciences; Solexa and HiSeg™ Illumina), massively parallel semiconductor sequencing (e.g., Ion Torrent), pyrosequencing technology (e.g., GS FLX and GS Junior Systems, Roche/454), and nanopore sequence (e.g., Oxford Nanopore Technologies).

A library of nucleic acids (e.g., extended nucleic acids) may be amplified in a variety of ways. A library of nucleic acids (e.g., extended nucleic acids) undergo exponential amplification, e.g., via PCR or emulsion PCR. Emulsion PCR is known to produce more uniform amplification (Hori, Fukano et al., Biochem Biophys Res Commun (2007) 352 (2): 323-328). Alternatively, a library of nucleic acids (e.g., extended nucleic acids) may undergo linear amplification, e.g., via in vitro transcription of template DNA using T7 RNA polymerase. The library of nucleic acids (e.g., extended nucleic acids) can be amplified using primers compatible with the universal forward priming site and universal reverse priming site contained therein. A library of extended nucleic acids (e.g., on the bait or capture nucleic acid) can also be amplified using tailed primers to add sequence to either the 5'-end, 3'-end or both ends of the extended nucleic acids. Sequences that can be added to the termini of the extended nucleic acids include library specific index sequences to allow multiplexing of multiple libraries in a single sequencing run, adaptor sequences, read primer sequences, or any other sequences for making the library of extended nucleic acids compatible for a sequencing platform. An example of a library amplification in preparation for next generation sequencing is as follows: a 20 µl PCR reaction volume is set up using an extended nucleic acid library eluted from ~1 mg of beads (~10 ng), 200 µM dNTP, 1 µM of each forward and reverse amplification primers, 0.5 µl (1 U) of Phusion Hot Start enzyme (New England Biolabs) and subjected to the following cycling conditions: 98° C. for 30 sec followed by 20 cycles of 98° C. for 10 sec, 60° C. for 30 sec, 72° C. for 30 sec, followed by 72° C. for 7 min, then hold at 4° C.

In certain embodiments, either before, during or following amplification, the library of nucleic acids (e.g., extended nucleic acids) can undergo target enrichment. In some embodiments, target enrichment can be used to selectively capture or amplify extended nucleic acids representing polypeptides of interest from a library of extended nucleic acids before sequencing. In some aspects, target enrichment for protein sequencing is challenging because of the high cost and difficulty in producing highly-specific binding agents for target proteins. In some cases, antibodies are notoriously non-specific and difficult to scale production across thousands of proteins. In some embodiments, the methods of the present disclosure circumvent this problem by converting the protein code into a nucleic acid code which can then make use of a wide range of targeted DNA enrichment strategies available for DNA libraries. In some cases, peptides of interest can be enriched in a sample by enriching their corresponding extended nucleic acids. Methods of targeted enrichment are known in the art, and include hybrid capture assays, PCR-based assays such as TruSeq custom Amplicon (Illumina), padlock probes (also referred to as molecular inversion probes), and the like (see, Mamanova et al., (2010) Nature Methods 7: 111-118; Bodi et al., J. Biomol. Tech. (2013) 24:73-86; Ballester et al., (2016) Expert Review of Molecular Diagnostics 357-372; Mertes et al., (2011) Brief Funct. Genomics 10:374-386; Nilsson et al., (1994) Science 265:2085-8; each of which are incorporated herein by reference in their entirety).

In one embodiment, a library of nucleic acids (e.g., extended nucleic acids) is enriched via a hybrid capture-based assay. In a hybrid-capture based assay, the library of extended nucleic acids is hybridized to target-specific oligonucleotides that are labeled with an affinity tag (e.g., biotin). Extended nucleic acids hybridized to the target-specific oligonucleotides are "pulled down" via their affinity tags using an affinity ligand (e.g., streptavidin coated beads), and background (non-specific) extended nucleic acids are washed away. The enriched extended nucleic acids (e.g., extended nucleic acids) are then obtained for positive enrichment (e.g., eluted from the beads). In some embodiments, oligonucleotides complementary to the corresponding extended nucleic acid library representations of peptides of interest can be used in a hybrid capture assay. In some embodiments, sequential rounds or enrichment can also be carried out, with the same or different bait sets.

To enrich the entire length of a polypeptide in a library of extended nucleic acids representing fragments thereof (e.g., peptides), "tiled" bait oligonucleotides can be designed across the entire nucleic acid representation of the protein.

In another embodiment, primer extension and ligation-based mediated amplification enrichment (AmpliSeq, PCR, TruSeq TSCA, etc.) can be used to select and module fraction enriched of library elements representing a subset of polypeptides. Competing oligonucleotides can also be employed to tune the degree of primer extension, ligation, or amplification. In the simplest implementation, this can be accomplished by having a mix of target specific primers comprising a universal primer tail and competing primers lacking a 5' universal primer tail. After an initial primer extension, only primers with the 5' universal primer sequence can be amplified. The ratio of primer with and without the universal primer sequence controls the fraction of target amplified. In other embodiments, the inclusion of hybridizing but non-extending primers can be used to modulate the fraction of library elements undergoing primer extension, ligation, or amplification.

Targeted enrichment methods can also be used in a negative selection mode to selectively remove extended nucleic acids from a library before sequencing. Examples of undesirable extended nucleic acids that can be removed are those representing over abundant polypeptide species, e.g., for proteins, albumin, immunoglobulins, etc.

A competitor oligonucleotide bait, hybridizing to the target but lacking a biotin moiety, can also be used in the hybrid capture step to modulate the fraction of any particular locus enriched. The competitor oligonucleotide bait competes for hybridization to the target with the standard biotinylated bait effectively modulating the fraction of target pulled down during enrichment. The ten orders dynamic range of protein expression can be compressed by several orders using this competitive suppression approach, especially for the overly abundant species such as albumin. Thus, the fraction of library elements captured for a given locus relative to standard hybrid capture can be modulated from 100% down to 0% enrichment.

Additionally, library normalization techniques can be used to remove overly abundant species from the extended nucleic acid library. This approach works best for defined length libraries originating from peptides generated by site-specific protease digestion such as trypsin, LysC, GluC, etc. In one example, normalization can be accomplished by denaturing a double-stranded library and allowing the library elements to re-anneal. The abundant library elements re-anneal more quickly than less abundant elements due to the second-order rate constant of bimolecular hybridization kinetics (Bochman, Paeschke et al. 2012). The ssDNA library elements can be separated from the abundant dsDNA library elements using methods known in the art, such as chromatography on hydroxyapatite columns (VanderNoot, et al., 2012, Biotechniques 53:373-380) or treatment of the library with a duplex-specific nuclease (DSN) from Kamchatka crab (Shagin et al., (2002) Genome Res. 12:1935-42) which destroys the dsDNA library elements.

Any combination of fractionation, enrichment, and subtraction methods, of the polypeptides before attachment to the solid support and/or of the resulting extended nucleic acid library can economize sequencing reads and improve measurement of low abundance species.

In some embodiments, a library of nucleic acids (e.g., extended nucleic acids) is concatenated by ligation or end-complementary PCR to create a long DNA molecule comprising multiple different extended recorder tags, extended coding tags, or di-tags, respectively (Du et al., (2003) BioTechniques 35:66-72; Muecke et al., (2008) Structure 16:837-841; U.S. Pat. No. 5,834,252, each of which is incorporated by reference in its entirety). This embodiment is preferable for nanopore sequencing in which long strands of DNA are analyzed by the nanopore sequencing device.

In some embodiments, direct single molecule analysis is performed on the nucleic acids (e.g., extended nucleic acids)

(see, e.g., Harris et al., (2008) Science 320:106-109). The nucleic acids (e.g., extended nucleic acids) can be analysed directly on the solid support, such as a flow cell or beads that are compatible for loading onto a flow cell surface (optionally microcell patterned), wherein the flow cell or beads can integrate with a single molecule sequencer or a single molecule decoding instrument. For single molecule decoding, hybridization of several rounds of pooled fluorescently-labeled of decoding oligonucleotides (Gunderson et al., (2004) Genome Res. 14:970-7) can be used to ascertain both the identity and order of the coding tags within the extended nucleic acids (e.g., on the bait or capture nucleic acid). In some embodiments, the binding agents may be labeled with cycle-specific coding tags as described above (see also, Gunderson et al., (2004) Genome Res. 14:970-7). Cycle-specific coding tags will work for both a single, concatenated extended nucleic acids representing a single polypeptide, or for a collection of extended nucleic acids representing a single polypeptide.

Following sequencing of the nucleic acid libraries (e.g., of extended nucleic acids), the resulting sequences can be collapsed by their UMIs and then associated to their corresponding polypeptides and aligned to the totality of the proteome. Resulting sequences can also be collapsed by their compartment tags and associated to their corresponding compartmental proteome, which in a particular embodiment contains only a single or a very limited number of protein molecules. Both protein identification and quantification can easily be derived from this digital peptide information.

In some embodiments, the coding tag sequence can be optimized for the particular sequencing analysis platform. In a particular embodiment, the sequencing platform is nanopore sequencing. In some embodiments, the sequencing platform has a per base error rate of >1%, >5%, >10%, >15%, >20%, >25%, or >30%. For example, if the extended nucleic acid is to be analyzed using a nanopore sequencing instrument, the barcode sequences (e.g., sequences comprising identifying information from the coding tag) can be designed to be optimally electrically distinguishable in transit through a nanopore. Moreover, a technique called duplex interrupted nanopore sequencing (DI) can be employed with nanopore strand sequencing without the need for a molecular motor, greatly simplifying the system design (Derrington et al., Proc Natl Acad Sci USA (2010) 107(37): 16060-16065). Readout of the extended nucleic acids via DI nanopore sequencing requires that the spacer elements in the concatenated extended nucleic acid library be annealed with complementary oligonucleotides. The oligonucleotides used herein may comprise LNAs, or other modified nucleic acids or analogs to increase the effective Tm of the resultant duplexes. As the single-stranded extended nucleic acid decorated with these duplex spacer regions is passed through the pore, the double strand region will become transiently stalled at the constriction zone enabling a current readout of about three bases adjacent to the duplex region. In a particular embodiment for DI nanopore sequencing, the encoder sequence comprising identifying information from the coding tag is designed in such a way that the three bases adjacent to the spacer element create maximally electrically distinguishable nanopore signals (Derrington et al., Proc Natl Acad Sci USA (2010) 107(37): 16060-16065). As an alternative to motor-free DI sequencing, the spacer element can be designed to adopt a secondary structure such as a G-quartet, which will transiently stall the extended nucleic acid as it passes through the nanopore enabling readout of the adjacent encoder sequence (Shim et al., Nucleic Acids Res (2009) 37(3): 972-982; Zhang et al., mAbs (2016) 8, 524-535). After proceeding past the stall, the next spacer will again create a transient stall, enabling readout of the next encoder sequence, and so forth.

The methods disclosed herein can be used for analysis, including detection, identification, quantitation and/or sequencing, of a plurality of polypeptide analytes simultaneously (multiplexing). Multiplexing as used herein refers to analysis of a plurality of polypeptides in the same assay. The plurality of polypeptides can be derived from the same sample or different samples. The plurality of polypeptides can be derived from the same subject or different subjects. The plurality of polypeptides that are analyzed can be different polypeptides, or the same polypeptide derived from different samples. A plurality of polypeptides includes 2 or more polypeptides, 5 or more polypeptides, 10 or more polypeptides, 50 or more polypeptides, 100 or more polypeptides, 500 or more polypeptides, 1000 or more polypeptides, 5,000 or more polypeptides, 10,000 or more polypeptides, 50,000 or more polypeptides, 100,000 or more polypeptides, 500,000 or more polypeptides, or 1,000,000 or more polypeptides.

Sample multiplexing can be achieved by upfront barcoding of the nucleic acid (e.g., bait or capture nucleic acids) associated with the polypeptide samples. Each barcode represents a different sample, and samples can be pooled prior to cyclic binding assays or sequence analysis. In some embodiments, polypeptides immobilized on the same bead are barcoded with a bead barcode. For example, the capture nucleic acid may include a bead barcode that allows the samples with different bead barcodes to be combined and processed for some or all steps of the protein analysis assay. In this way, many barcode-labeled samples can be simultaneously processed in a single tube. This approach is a significant improvement on immunoassays conducted on reverse phase protein arrays (RPPA) (Akbani et al., Mol Cell Proteomics (2014) 13(7): 1625-1643; Creighton et al., Drug Des Devel Ther (2015) 9: 3519-3527; Nishizuka et al., Drug Metab Pharmacokinet (2016) 31(1): 35-45). In this way, the present disclosure essentially provides a highly digital sample and analyte multiplexed alternative to the RPPA assay with a simple workflow.

III. KITS, COMPONENTS, AND ARTICLES OF MANUFACTURE

Provided herein are kits and articles of manufacture comprising components for treating or preparing analytes. In some embodiments, the kit comprises a plurality of bait nucleic acids configured to be attached to an analyte and a solid support comprising a plurality of attached capture nucleic acids, each of said capture nucleic acids comprising a sequence complementary to a corresponding bait nucleic acid, wherein any adjacently attached capture nucleic acids are spaced apart on the solid support at an average distance of about 50 nm or greater. In some embodiments, the kits also include instructions for using the components for preparing and treating analytes. In some embodiments, the kits provided herein are for use in treating analytes comprising peptides, polypeptides, and proteins for sequencing and/or analysis. In some embodiments, the kits provided herein are for preparing analytes for protein analysis which employs barcoding and nucleic acid encoding of molecular recognition events, and/or detectable labels. In some embodiments, the kits also include other components for treating the polypeptides and analysis of the polypeptides, including other reagents for polypeptide analysis.

In one aspect, provided herein are components used to prepare a reaction mixture. In preferred embodiments, the reaction mixture is a solution. In some preferred embodiments, the reaction mixture includes one or more of the following: a capture nucleic acid (e.g., attached to a solid or insoluble support) and a bait nucleic acid. In some embodiments, the kits are for preparing a plurality of analytes obtained from a sample, such as any samples described in Section IA. In some embodiments, the capture nucleic acids are provided on the solid support in a format that is compatible for performing a ProteoCode assay.

In some of any of the provided embodiments, the kit comprises a plurality of bait nucleic acids and a plurality of capture nucleic acids. In some embodiments, the kit comprises any of the bait nucleic acids described in Section I. In some embodiments, the bait nucleic acid is configured to allow the analyte to be attached to the 3' end of the bait nucleic acid. In some embodiments, the bait nucleic acid is configured to allow the analyte to be attached to the 5' end of the bait nucleic acid. In some cases, the bait nucleic acid is configured to allow the analyte to be attached to an internal position of the bait nucleic acid. In some embodiments, the bait nucleic acid comprises a reactive coupling moiety. In some examples, the reactive coupling moiety is activated by applying a light energy, a chemical reagent or an enzymatic reagent.

In some embodiments, the kit comprises any of the capture nucleic acids described in Section I. In some embodiments, the capture nucleic acids are provided on a solid support. In some embodiments, the capture nucleic acids comprise one or more components for downstream sequencing, including a universal priming site and/or an adaptor sequence. The capture nucleic acid maybe be provided in a format that enables desired spacing of the analytes, e.g., analytes in the form of nucleic acid-analyte chimeras, on the solid support. In some embodiments of the kits, the concentration of capture nucleic acids may be titrated on the substrate surface. For example, the capture nucleic acid is configured to couple the analyte to the solid support such that any adjacently coupled analytes, e.g., analytes in the form of nucleic acid-analyte chimeras, are spaced apart from each other on the solid support at an average distance of ≥60 nm, ≥70 nm, ≥80 nm, ≥90 nm, ≥100 nm, ≥200 nm, ≥300 nm, ≥400 nm, ≥500 nm, or ≥1000 nm. In some cases, the capture nucleic acid is configured to couple the analyte to the solid support such that any adjacently coupled analytes, e.g., analytes in the form of nucleic acid-analyte chimeras, are spaced apart from each other on the solid support at an average distance which ranges from about 50 to 100 nm, from about 50 to 250 nm, from about 50 to 500 nm, from about 50 to 750 nm, from about 50 to 1000 nm, from about 50 to 1500 nm, from about 50 to 2000 nm, from about 100 to 250 nm, from about 100 to 500 nm, from about 200 to 500 nm, from about 300 to 500 nm, from about 100 to 1000 nm, from about 500 to 600 nm, from about 500 to 700 nm, from about 500 to 800 nm, from about 500 to 900 nm, from about 500 to 1000 nm, from about 500 to 2000 nm, from about 500 to 5000 nm, from about 1000 to 5000 nm, or from about 3000 to 5000 nm. In some preferred embodiments, the capture nucleic acid is configured to couple the analyte to the solid support such that any adjacently coupled analytes, e.g., analytes in the form of nucleic acid-analyte chimeras, are spaced apart from each other on the solid support at an average distance which ranges from about 50 to 500 nm.

In some embodiments, any adjacently coupled capture nucleic acids are spaced apart from each other on the surface or within the volume (e.g., porous supports) of a solid support at a distance of about 50 nm to about 500 nm, or about 50 nm to about 400 nm, or about 50 nm to about 300 nm, or about 50 nm to about 200 nm, or about 50 nm to about 100 nm. In some embodiments, any adjacently coupled analytes, e.g., analytes in the form of nucleic acid-analyte chimeras, are spaced apart from each other on the surface of a solid support with an average distance of at least 50 nm, at least 60 nm, at least 70 nm, at least 80 nm, at least 90 nm, at least 100 nm, at least 150 nm, at least 200 nm, at least 250 nm, at least 300 nm, at least 350 nm, at least 400 nm, at least 450 nm, or at least 500 nm. In some embodiments, any adjacently coupled analytes, e.g., analytes in the form of nucleic acid-analyte chimeras, are spaced apart from each other on the surface of a solid support with an average distance of at least 50 nm.

In some embodiments, the kit comprises substrates or solid supports with capture nucleic acids attached. The solid supports may be selected from the group consisting of a bead, a porous bead, a magnetic bead, a paramagnetic bead, a porous matrix, an array, a surface, a glass surface, a silicon surface, a plastic surface, a slide, a filter, nylon, a chip, a silicon wafer chip, a flow through chip, a biochip including signal transducing electronics, a well, a microtitre well, a plate, an ELISA plate, a disc, a spinning interferometry disc, a membrane, a PTFE membrane, a nitrocellulose membrane, a nitrocellulose-based polymer surface, a nanoparticle (e.g., comprising a metal such as magnetic nanoparticles ($Fe_3O_4$), gold nanoparticles, and/or silver nanoparticles), quantum dots, a nanoshell, a nanocage, a microsphere, or any combination thereof. In some embodiments, the kit comprises a plurality of substrates. In some cases, the surface of the solid support comprises a reactive coupling moiety. In some embodiments, the capture nucleic acid comprises a reactive coupling moiety.

In some embodiments, the kits and articles of manufacture further comprise a plurality of barcodes. The barcode may include a compartment barcode, a partition barcode, a sample barcode, a fraction barcode, or any combination thereof. In some cases, the barcode comprises a unique molecule identifier (UMI). In some examples, the barcode comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof.

In some embodiments, the barcodes in the kit are attached to the bait nucleic acid and/or attached to the capture nucleic acid. In some embodiments, the barcodes in the kit are attached to the capture nucleic acids attached to the solid support (e.g., beads). In some cases, the barcodes are configured to be attached to the bait nucleic acid or the capture nucleic acid. In certain embodiments, each population of nucleic acid species is in a separate container. For example, the barcodes are provided in individual containers wherein each container holds a plurality of barcodes that are the same. The barcodes may also be provided in any suitable material or structure with compartments, such that various barcodes are spatially separated from each other. For example, a microplate is used to provide 96 barcodes with each well containing a plurality of the same barcode. Any suitable container for providing the barcodes may be used, including but not limited to microplates having 6, 24, 96, 384, 1536, 3456, or 9600 wells. In some embodiments, the kits and articles of manufacture further comprise a plurality of UMIs (e.g., polynucleotides comprising UMIs).

In some embodiments, the kits and articles of manufacture further comprise a coupling reagent. For example, the coupling reagent may be an enzyme or a chemical coupling reagent. The reagent may be used to attach the bait nucleic acid to the capture nucleic acid, to attach the bait nucleic acid to the solid support, to attach the analyte to the bait nucleic acid, and/or to attach any two or more nucleic acid components. The kits may further comprise any related components needed to activate the coupling reagent. In some specific embodiments, the kit further comprises a ligase.

In some embodiments, the kit further comprises reagents for treating the analytes. Any combination of fractionation, enrichment, and subtraction methods, of the analytes may be performed. For example, the reagent may be used to fragment or digest the analytes. In some cases, the kit comprises reagents and components to fractionate, isolate, subtract, enrich analytes. In some examples, the kits further comprises a protease such as trypsin, LysN, or LysC.

In some embodiments, the kit also comprises one or more buffers or reaction fluids necessary for any of the desired reaction to occur. Buffers including wash buffers, reaction buffers, and binding buffers, elution buffers and the like are known to those or ordinary skill in the arts. In some embodiments, the kits further include buffers and other components to accompany other reagents described herein. The reagents, buffers, and other components may be provided in vials (such as sealed vials), vessels, ampules, bottles, jars, flexible packaging (e.g., sealed Mylar or plastic bags), and the like. Any of the components of the kits may be sterilized and/or sealed.

In some embodiments, the kit includes one or more reagents for nucleic acid sequence analysis. In some examples, the reagent for sequence analysis is for use in sequencing by synthesis, sequencing by ligation, sequencing by hybridization, polony sequencing, ion semiconductor sequencing, pyrosequencing, single molecule real-time sequencing, nanopore-based sequencing, or direct imaging of DNA using advanced microscopy, or any combination thereof.

In some embodiments, the kits or articles of manufacture may further comprise instruction(s) on the methods and uses described herein. In some embodiments, the instructions are directed to methods of preparing and treating polypeptides. The kits described herein may also include other materials desirable from a commercial and user standpoint, including other buffers, diluents, filters, syringes, and package inserts with instructions for performing any methods described herein.

Any of the above-mentioned kit components, and any molecule, molecular complex or conjugate, reagent (e.g., chemical or biological reagents), agent, structure (e.g., support, surface, particle, or bead), reaction intermediate, reaction product, binding complex, or any other article of manufacture disclosed and/or used in the exemplary kits and methods, may be provided separately or in any suitable combination in order to form a kit.

IV. EXEMPLARY EMBODIMENTS

Among the provided embodiments are:
1. A method for treating an analyte, comprising:
attaching an analyte to a bait nucleic acid to generate a nucleic acid-analyte chimera;
bringing the nucleic acid-analyte chimera into proximity with a solid support by hybridizing the bait nucleic acid in the nucleic acid-analyte chimera to a capture nucleic acid attached to the solid support; and
covalently coupling the nucleic acid-analyte chimera to the solid support;
wherein a plurality of the nucleic acid-analyte chimeras is coupled on the solid support and any adjacently coupled nucleic acid-analyte chimeras are spaced apart from each other at an average distance of about 50 nm or greater.

2. The method of embodiment 1, wherein the analyte is attached to the 3' end of the bait nucleic acid.

3. The method of embodiment 1, wherein the analyte is attached to the 5' end of the bait nucleic acid.

4. The method of embodiment 1, wherein the analyte is attached to an internal position of the bait nucleic acid.

5. The method of any one of embodiments 1-4, wherein any adjacently coupled nucleic acid-analyte chimeras are spaced apart at an average distance of about ≥60 nm, ≥70 nm, ≥80 nm, ≥90 nm, ≥100 nm, ≥200 nm, ≥300 nm, ≥400 nm, ≥500 nm, or ≥1000 nm.

6. The method of any one of embodiments 1-4, wherein any adjacently coupled nucleic acid-analyte chimeras are spaced apart at an average distance which ranges from about 50 to 100 nm, from about 50 to 250 nm, from about 50 to 500 nm, from about 50 to 750 nm, from about 50 to 1000 nm, from about 50 to 1500 nm, from about 50 to 2000 nm, from about 100 to 250 nm, from about 100 to 500 nm, from about 200 to 500 nm, from about 300 to 500 nm, from about 100 to 1000 nm, from about 500 to 600 nm, from about 500 to 700 nm, from about 500 to 800 nm, from about 500 to 900 nm, from about 500 to 1000 nm, from about 500 to 2000 nm, from about 500 to 5000 nm, from about 1000 to 5000 nm, or from about 3000 to 5000 nm.

7. The method of any one of embodiments 1-4, wherein any adjacently coupled nucleic acid-analyte chimeras are spaced apart at an average distance which ranges from about 50 to 500 nm.

8. The method of any one of embodiments 1-7, wherein the capture nucleic acid, the nucleic acid-analyte chimera, and/or the bait nucleic acid further comprises a barcode.

9. The method of any one of embodiments 1-8, further comprising attaching a barcode to the coupled nucleic acid-analyte chimera.

10. The method of embodiment 8 or embodiment 9, wherein the barcode comprises a compartment barcode, a partition barcode, a sample barcode, a fraction barcode, or any combination thereof.

11. The method of any one of embodiments 8-10, wherein the barcode comprises a unique molecule identifier (UMI).

12. The method of any one of embodiments 1-11, wherein the capture nucleic acid, the nucleic acid-analyte chimera, the bait nucleic acid, and/or the coupled nucleic acid-analyte chimera further comprises a unique molecule identifier (UMI).

13. The method of any one of embodiments 9-12, wherein the barcode comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof.

14. The method of any one of embodiments 1-13, wherein the nucleic acid-analyte chimera is covalently coupled directly or indirectly to the solid support.

15. The method of any one of embodiments 1-14, wherein the bait nucleic acid is covalently coupled to the capture nucleic acid.

16. The method of embodiment 15, wherein the covalent coupling is performed using a ligation reagent.

17. The method of embodiment 15 or embodiment 16, wherein the 5' end of the bait nucleic acid is coupled to the 3' end of the capture nucleic acid.

18. The method of embodiment 15 or embodiment 16, wherein the 3' end of the bait nucleic acid is coupled to the 5' end of the capture nucleic acid.

19. The method of any one of embodiments 1-18, wherein the capture nucleic acid comprises a nucleic acid hairpin.

20. The method of any one of embodiments 1-19, wherein the capture nucleic acid comprises a splinted nucleic acid.

21. The method of embodiment 20, wherein the splinted nucleic acid comprises a sequence complementary to the capture nucleic acid and/or the bait nucleic acid.

22. The method of any one of embodiments 1-21, wherein the capture nucleic acid comprises a reactive coupling moiety.

23. The method of embodiment 22, wherein the capture nucleic acid is attached to the solid support via the reactive coupling moiety.

24. The method of embodiment 22, wherein the capture nucleic acid is attached to the bait nucleic acid via the reactive coupling moiety.

25. The method of any one of embodiments 1-24, wherein the analyte is obtained from a biological sample.

26. The method of any one of embodiments 1-25, wherein the hybridization of the bait nucleic acid to the capture nucleic comprises hybridization of 8 or more complementary bases, 16 or more complementary bases, 24 or more complementary bases, 34 or more complementary bases.

27. The method of any one of embodiments 1-26, wherein the hybridization of the bait nucleic acid to the capture nucleic comprises hybridization of 18 or more complementary bases.

28. The method of any one of embodiments 1-27, wherein the analyte is a polypeptide.

29. The method of embodiment 28, wherein the analyte is a protein or peptide.

30. The method of embodiment 29, wherein the peptide is obtained by fragmenting protein(s), e.g., protein(s) from a biological sample.

31. The method of embodiment 30, wherein the fragmenting is performed by contacting the protein(s) with a protease.

32. The method of embodiment 31, wherein the protease is trypsin, LysN, or LysC.

33. The method of any one of embodiments 1-32, wherein the analyte comprises analytes from multiple, pooled samples.

34. The method of any one of embodiments 1-33, wherein the analyte and/or bait nucleic comprises a reactive coupling moiety.

35. The method of any one of embodiments 1-34, wherein the analyte is attached to the bait nucleic acid using chemical ligation.

36. The method of any one of embodiments 1-35, wherein the analyte is directly or indirectly attached to the bait nucleic acid.

37. The method of any one of embodiments 1-36, wherein after the coupling of the nucleic acid-analyte chimera to the solid support:
the 5' end of the bait nucleic acid is available for reaction;
the 5' end of the capture nucleic acid is available for reaction;
the 3' end of the bait nucleic acid is available for reaction; and/or the 3' end of the capture nucleic acid is available for reaction.

38. The method of embodiment 37, wherein the nucleic acid is available for an extension reaction, e.g., a PCR extension reaction, and/or a ligation reaction.

39. The method of any one of embodiments 1-38, wherein the bait nucleic acid and/or capture nucleic acid further comprises a spacer polymer.

40. The method of embodiment 39, wherein the spacer polymer comprises at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 15 nucleotides, or at least 20 or more nucleotides.

41. The method of embodiment 39 and embodiment 40, wherein the spacer polymer comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof.

42. The method of any one of embodiments 39-41, wherein the bait nucleic acid comprises the spacer polymer at its 5'-terminus and/or 3'-terminus.

43. The method of any one of embodiments 39-41, wherein the capture nucleic acid comprises the spacer polymer at its 5'-terminus and/or 3'-terminus.

44. The method of any one of embodiments 1-43, wherein the bait nucleic acid and/or capture nucleic acid further comprises a universal priming site.

45. The method of embodiment 44, wherein the universal priming site comprises a priming site for amplification, sequencing, or both.

46. The method of any one of embodiments 1-45, wherein the capture nucleic acid comprises an adapter nucleic acid sequence for use in sequencing.

47. The method of embodiment 46, wherein the adaptor nucleic acid sequence is for use with an Illumina sequencing platform or a Pacific Biosciences of California sequencing platform.

48. The method of any one of embodiments 1-47, wherein the solid support is a bead, a porous bead, a porous matrix, an array, a glass surface, a silicon surface, a plastic surface, a filter, a membrane, a PTFE membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

49. The method of embodiment 48, wherein the solid support comprises a polystyrene bead, a polyacrylate bead, a polymer bead, an agarose bead, a cellulose bead, a dextran bead, an acrylamide bead, a solid core bead, a porous bead, a paramagnetic bead, a glass bead, a controlled pore bead, a silica-based bead, or any combinations thereof.

50. The method of any one of embodiments 1-49, further comprising:
contacting the analyte with a binding agent capable of binding to the analyte, wherein the binding agent comprises a coding tag with identifying information regarding the binding agent;
and transferring the identifying information of the coding tag to the bait nucleic acid or capture nucleic acid.

51. The method of embodiment 50, further comprising repeating one or more times:
contacting the analyte with an additional binding agent capable of binding to the analyte, wherein the additional binding agent comprises a coding tag with identifying information regarding the additional binding agent; and transferring the identifying information of the coding tag regarding the additional binding agent to the bait nucleic acid or capture nucleic acid.

52. The method of embodiment 50 or embodiment 51, wherein transferring the identifying information of the coding tag to the bait nucleic acid or capture nucleic acid is mediated by a DNA ligase.

53. The method of embodiment 50 or embodiment 51, wherein transferring the identifying information of the coding tag to the bait nucleic acid or capture nucleic acid is mediated by a DNA polymerase.

54. The method of embodiment 50 or embodiment 51, wherein transferring the identifying information of the coding tag to the bait nucleic acid or capture nucleic acid is mediated by chemical ligation.

55. The method of any one of embodiments 50-54, wherein the coding tag further comprises a spacer, a binding cycle specific sequence, a unique molecular identifier, a universal priming site, or any combination thereof.

56. A nucleic acid-analyte conjugate generated by the steps of:

attaching an analyte to a bait nucleic acid to generate a nucleic acid-analyte chimera;

bringing the nucleic acid-analyte chimera into proximity with a solid support by hybridizing the bait nucleic acid in the nucleic acid-analyte chimera to a capture nucleic acid attached to the solid support; and covalently coupling the nucleic acid-analyte chimera to the solid support;

wherein a plurality of nucleic acid-analyte chimeras is coupled on the solid support and any adjacently coupled nucleic acid-analyte chimeras are spaced apart at an average distance of about 50 nm or greater.

57. The nucleic acid-analyte conjugate of embodiment 56, wherein the analyte is attached to the 3' end of the bait nucleic acid.

58. The nucleic acid-analyte conjugate of embodiment 56, wherein the analyte is attached to the 5' end of the bait nucleic acid.

59. The nucleic acid-analyte conjugate of embodiment 56, wherein the analyte is attached to an internal position of the bait nucleic acid.

60. The nucleic acid-analyte conjugate of any one of embodiments 56-59, wherein any adjacently coupled nucleic acid-analyte chimeras are spaced apart at an average distance of about ≥60 nm, ≥70 nm, ≥80 nm, ≥90 nm, ≥100 nm, ≥200 nm, ≥300 nm, ≥400 nm, ≥500 nm, or ≥1000 nm.

61. The nucleic acid-analyte conjugate of any one of embodiments 56-60, wherein any adjacently coupled nucleic acid-analyte chimeras are spaced apart at an average distance which ranges from about 50 to 100 nm, from about 50 to 250 nm, from about 50 to 500 nm, from about 50 to 750 nm, from about 50 to 1000 nm, from about 50 to 1500 nm, from about 50 to 2000 nm, from about 100 to 250 nm, from about 100 to 500 nm, from about 200 to 500 nm, from about 300 to 500 nm, from about 100 to 1000 nm, from about 500 to 600 nm, from about 500 to 700 nm, from about 500 to 800 nm, from about 500 to 900 nm, from about 500 to 1000 nm, from about 500 to 2000 nm, from about 500 to 5000 nm, from about 1000 to 5000 nm, or from about 3000 to 5000 nm.

62. The nucleic acid-analyte conjugate of any one of embodiments 56-61, wherein any adjacently coupled nucleic acid-analyte chimeras are spaced apart at an average distance which ranges from about 50 to 500 nm.

63. The nucleic acid-analyte conjugate of any one of embodiments 56-62, wherein the capture nucleic acid, the nucleic acid-analyte chimera, and/or the bait nucleic acid further comprises a barcode.

64. The nucleic acid-analyte conjugate of any one of embodiments 56-63, wherein the coupled nucleic acid-analyte chimera further comprises a barcode.

65. The nucleic acid-analyte conjugate of embodiment 64, wherein the barcode comprises a compartment barcode, a partition barcode, a sample barcode, a fraction barcode, or any combination thereof.

66. The nucleic acid-analyte conjugate of any one of embodiments 62-64, wherein the barcode comprises a unique molecule identifier (UMI).

67. The nucleic acid-analyte conjugate of any one of embodiments 56-66, wherein the capture nucleic acid, the nucleic acid-analyte chimera, the bait nucleic acid, and/or the coupled nucleic acid-analyte chimera further comprises a unique molecule identifier (UMI).

68. The nucleic acid-analyte conjugate of any one of embodiments 64-67, wherein the barcode comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof.

69. The nucleic acid-analyte conjugate of any one of embodiments 56-68, wherein the nucleic acid-analyte chimera is covalently coupled directly or indirectly to the solid support.

70. The nucleic acid-analyte conjugate of any one of embodiments 56-69, wherein the bait nucleic acid is covalently coupled to the capture nucleic acid.

71. The nucleic acid-analyte conjugate of embodiment 70, wherein the covalent coupling is performed using a ligation reagent.

72. The nucleic acid-analyte conjugate of embodiment 70 or embodiment 71, wherein the 5' end of the bait nucleic acid is coupled to the 3' end of the capture nucleic acid.

73. The nucleic acid-analyte conjugate of embodiment 70 or embodiment 71, wherein the 3' end of the bait nucleic acid is coupled to the 5' end of the capture nucleic acid.

74. The nucleic acid-analyte conjugate of any one of embodiments 56-73, wherein the capture nucleic acid comprises a nucleic acid hairpin.

75. The nucleic acid-analyte conjugate of any one of embodiments 56-74, wherein the capture nucleic acid comprises a splinted nucleic acid.

76. The nucleic acid-analyte conjugate of embodiment 75, wherein the splinted nucleic acid comprises a sequence complementary to the capture nucleic acid and/or the bait nucleic acid.

77. The nucleic acid-analyte conjugate of any one of embodiments 56-76, wherein the capture nucleic acid comprises a reactive coupling moiety.

78. The nucleic acid-analyte conjugate of embodiment 77, wherein the capture nucleic acid is attached to the solid support via the reactive coupling moiety.

79. The nucleic acid-analyte conjugate of embodiment 77, wherein the capture nucleic acid is attached to the bait nucleic acid via the reactive coupling moiety.

80. The nucleic acid-analyte conjugate of any one of embodiments 56-79, wherein the analyte is obtained from a biological sample.

81. The nucleic acid-analyte conjugate of any one of embodiments 56-80, wherein the hybridization of the bait nucleic acid to the capture nucleic comprises hybridization of 8 or more complementary bases, 16 or more complementary bases, 24 or more complementary bases, 34 or more complementary bases.

82. The nucleic acid-analyte conjugate of any one of embodiments 56-80, wherein the hybridization of the bait nucleic acid to the capture nucleic comprises hybridization of 16 or more complementary bases.

83. The nucleic acid-analyte conjugate of any one of embodiments 56-82, wherein the analyte is a polypeptide.

84. The nucleic acid-analyte conjugate of embodiment 82, wherein the analyte is a protein or peptide.

85. The nucleic acid-analyte conjugate of embodiment 84, wherein the peptide is obtained by fragmenting protein(s), e.g., protein(s) from a biological sample.

86. The nucleic acid-analyte conjugate of embodiment 85, wherein the fragmenting is performed by contacting the protein(s) with a protease.

87. The nucleic acid-analyte conjugate of embodiment 86, wherein the protease is trypsin, LysN, or LysC.

88. The nucleic acid-analyte conjugate of any one of embodiments 56-87, wherein the analyte comprises analytes from multiple, pooled samples.

89. The nucleic acid-analyte conjugate of any one of embodiments 56-88, wherein the analyte and/or bait nucleic comprises a reactive coupling moiety.

90. The nucleic acid-analyte conjugate of any one of embodiments 56-89, wherein the analyte is attached to the bait nucleic acid using chemical ligation.

91. The nucleic acid-analyte conjugate of any one of embodiments 56-90, wherein the analyte is directly or indirectly attached to the bait nucleic acid.

92. The nucleic acid-analyte conjugate of any one of embodiments 56-91, wherein after the coupling the nucleic acid-analyte chimera to the solid support:
the 5' end of the bait nucleic acid is available for reaction;
the 5' end of the capture nucleic acid is available for reaction;
the 3' end of the bait nucleic acid is available for reaction; and/or
the 3' end of the capture nucleic acid is available for reaction 93. The nucleic acid-analyte conjugate of embodiment 92, wherein the nucleic acid is available for an extension reaction, e.g., a PCR extension reaction, and/or a ligation reaction.

94. The nucleic acid-analyte conjugate of any one of embodiments 54-93, wherein the bait nucleic acid and/or capture nucleic acid further comprises a spacer polymer.

95. The nucleic acid-analyte conjugate of embodiments 94, wherein the spacer polymer comprises at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 15 nucleotides, or at least 20 or more nucleotides.

96. The nucleic acid-analyte conjugate of embodiment 94 or embodiment 95, wherein the spacer polymer comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof.

97. The nucleic acid-analyte conjugate of any one of embodiments 94-96, wherein the bait nucleic acid comprises the spacer polymer at its 5'-terminus and/or 3'-terminus.

98. The nucleic acid-analyte conjugate of any one of embodiments 94-96, wherein the capture nucleic acid comprises the spacer polymer at its 5'-terminus and/or 3'-terminus.

99. The nucleic acid-analyte conjugate of any one of embodiments 56-98, wherein the bait nucleic acid and/or capture nucleic acid further comprises a universal priming site.

100. The nucleic acid-analyte conjugate of embodiment 99, wherein the universal priming site comprises a priming site for amplification, sequencing, or both.

101. The nucleic acid-analyte conjugate of any one of embodiments 56-100, wherein the capture nucleic acid comprises an adapter nucleic acid sequence for use in sequencing.

102. The nucleic acid-analyte conjugate of embodiment 101, wherein the adaptor nucleic acid sequence is for use with an Illumina sequencing platform or a Pacific Biosciences of California sequencing platform.

103. The nucleic acid-analyte conjugate of any one of embodiments 56-102, wherein the solid support is a bead, a porous bead, a porous matrix, an array, a glass surface, a silicon surface, a plastic surface, a filter, a membrane, a PTFE membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

104. The nucleic acid-analyte conjugate of embodiment 103, wherein the solid support comprises a polystyrene bead, a polyacrylate bead, a polymer bead, an agarose bead, a cellulose bead, a dextran bead, an acrylamide bead, a solid core bead, a porous bead, a paramagnetic bead, a glass bead, a controlled pore bead, a silica-based bead, or any combinations thereof.

105. A kit, comprising:
(a) a plurality of bait nucleic acids, each of said bait nucleic acids is configured to be attached to an analyte;
(b) a solid support comprising a plurality of attached capture nucleic acids, each of said capture nucleic acids comprising a sequence complementary to a corresponding bait nucleic acid, wherein any adjacently attached capture nucleic acids are spaced apart on said solid support at an average distance of about 50 nm or greater.

106. The kit of embodiment 105, wherein at least one of the bait nucleic acids is configured to allow the analyte to be attached to the 3' end of the bait nucleic acid.

107. The kit of embodiment 105, wherein at least one of the bait nucleic acids is configured to allow the analyte to be attached to the 5' end of the bait nucleic acid.

108. The kit of embodiment 105, wherein at least one of the bait nucleic acids is configured to allow the analyte to be attached to an internal position of the bait nucleic acid.

109. The kit of any one of embodiments 105-108, wherein any adjacently attached capture nucleic acids are configured to couple the analyte to the solid support spaced apart on the solid support at an average distance of about ≥60 nm, ≥70 nm, ≥80 nm, ≥90 nm, ≥100 nm, ≥200 nm, ≥300 nm, ≥400 nm, ≥500 nm, or ≥1000 nm.

110. The kit of any one of embodiments 105-109, wherein any adjacently attached capture nucleic acids are configured to couple the analyte to the solid support spaced apart on the solid support at an average distance which ranges from about 50 to 100 nm, from about 50 to 250 nm, from about 50 to 500 nm, from about 50 to 750 nm, from about 50 to 1000 nm, from about 50 to 1500 nm, from about 50 to 2000 nm, from about 100 to 250 nm, from about 100 to 500 nm, from about 200 to 500 nm, from about 300 to 500 nm, from about 100 to 1000 nm, from about 500 to 600 nm, from about 500 to 700 nm, from about 500 to 800 nm, from about 500 to 900 nm, from about 500 to 1000 nm, from about 500 to 2000 nm, from about 500 to 5000 nm, from about 1000 to 5000 nm, or from about 3000 to 5000 nm.

111. The kit of any one of embodiments 105-109, wherein any adjacently attached capture nucleic acids are configured to couple the analyte to the solid support spaced apart on the solid support at an average distance which ranges from about 50 to 500 nm.

112. The kit of any one of embodiments 105-111, further comprising a plurality of barcodes.

113. The kit of embodiment 112, wherein the barcodes are attached to the bait nucleic acid or the capture nucleic acid, or the barcodes are configured to be attached to the bait nucleic acid or the capture nucleic acid.

114. The kit of embodiment 112 or embodiment 113, wherein the barcode comprises a compartment barcode, a partition barcode, a sample barcode, a fraction barcode, or any combination thereof.

115. The kit of any one of embodiments 112-114, wherein the barcode comprises a unique molecule identifier (UMI).

116. The kit of any one of embodiments 105-115, wherein at least one of the capture nucleic acids and/or at least one of the bait nucleic acids further comprises a unique molecule identifier (UMI).

117. The kit of any one of embodiments 109-116, wherein the barcode comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof.

118. The kit of any one of embodiments 105-117, wherein at least one of the bait nucleic acids comprises a reactive coupling moiety.

119. The kit of any one of embodiments 105-118, wherein the surface of the solid support comprises a reactive coupling moiety.

120. The kit of any one of embodiments 105-119, wherein at least one of the capture nucleic acids comprises a reactive coupling moiety.

121. The kit of any one of embodiments 118-120, wherein the reactive coupling moiety is configured to be activated by applying a light energy, a chemical reagent or an enzymatic reagent.

122. The kit of embodiment 121, wherein the enzymatic reagent is a ligase.

123. The kit of any one of embodiments 105-122, further comprising a coupling reagent.

124. The kit of embodiment 123, wherein the coupling reagent is an enzymatic coupling reagent or a chemical coupling reagent.

125. The kit of embodiment 124, wherein the enzymatic coupling reagent is a ligase.

126. The kit of any one of embodiments 105-125, further comprising a protease.

127. The kit of embodiment 126, wherein the protease is trypsin, LysN, or LysC.

128. The kit of any one of embodiments 105-127, wherein at least one of the capture nucleic acids comprises a nucleic acid hairpin.

129. The kit of any one of embodiments 105-128, wherein the capture nucleic acid comprises a splinted nucleic acid.

130. The kit of embodiment 129, wherein the splinted nucleic acid comprises a sequence complementary to the capture nucleic acid and/or the bait nucleic acid.

131. The kit of any one of embodiments 105-130, wherein the complementary sequence of at least one of the bait nucleic acids to at least one of the capture nucleic acids comprises 8 or more complementary bases, 16 or more complementary bases, 24 or more complementary bases, 34 or more complementary bases.

132. The kit of any one of embodiments 105-130, wherein the complementary sequence of at least one of the bait nucleic acids to at least one of the capture nucleic acids comprises 16 or more complementary bases.

133. The kit of any one of embodiments 105-132, further comprising a chemical ligation reagent.

134. The kit of any one of embodiments 105-133, wherein at least one of the bait nucleic acids and/or at least one of capture nucleic acids further comprises a spacer polymer.

135. The kit of embodiment 134, wherein the spacer polymer comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof.

136. The kit of any one of embodiments 105-135, wherein at least one of the bait nucleic acids and/or at least one of capture nucleic acids further comprises a universal priming site.

137. The kit of embodiment 136, wherein the universal priming site comprises a priming site for amplification, sequencing, or both.

138. The kit of any one of embodiments 105-137, wherein the capture nucleic acid comprises an adapter nucleic acid sequence for use in sequencing.

139. The kit of embodiment 138, wherein the adaptor nucleic acid sequence is for use with an Illumina sequencing platform or a Pacific Biosciences sequencing platform.

140. The kit of any one of embodiments 134-139, wherein at least one of the bait nucleic acids comprises the spacer polymer at its 5'-terminus and/or 3'-terminus.

141. The kit of any one of embodiments 134-140, wherein at least one of the capture nucleic acids comprises the spacer polymer at its 5'-terminus and/or 3'-terminus.

142. The kit of any one of embodiments 105-141, wherein the solid support is a bead, a porous bead, a porous matrix, an array, a glass surface, a silicon surface, a plastic surface, a filter, a membrane, a PTFE membrane, nylon, a silicon wafer chip, a flow through chip, a biochip including signal transducing electronics, a microtitre well, an ELISA plate, a spinning interferometry disc, a nitrocellulose membrane, a nitrocellulose-based polymer surface, a nanoparticle, or a microsphere.

V. EXAMPLES

The following examples are offered to illustrate but not to limit the methods, compositions, and uses provided herein.

Example 1: Assessment of Analyte Immobilization Using Nucleic Acid Hybridization and Coupling to a Solid Support This example describes exemplary methods for coupling nucleic acid-peptide analyte chimeras to a solid support and assessment of an encoding assay using immobilized analytes.

In a hybridization based method of immobilization, nucleic acid-peptide chimeras were hybridized and ligated to hairpin capture DNAs that were chemically immobilized on magnetic beads. The capture nucleic acids were conjugated to the beads using trans-cyclooctene (TCO) and methyltetrazine (mTet)-based click chemistry. TCO-modified short hairpin capture nucleic acids (16 basepair stem, 5 base loop, 24 base 5' overhang) were reacted with mTet-coated magnetic beads. Phosphorylated nucleic acid-peptide chimeras (10 nM) were annealed to the hairpin DNAs attached to beads in 5×SSC, 0.02% SDS, and incubated for 30 minutes at 37° C. The beads were washed once with PBST and resuspended in 1× Quick ligation solution (New England Biolabs, USA) with T4 DNA ligase. After a 30-minute incubation at 25° C., the beads were washed twice with PBST and resuspended in the 50 µL of PBST. The total immobilized nucleic acid-peptide chimeras including amino FA-terminal peptides (FAGVAMPGAEDDVVGSGSK; SEQ ID NO: 3), amino AFA-terminal peptides (AFAGVAMPGAEDDVVGSGSK; SEQ ID NO: 4), and an amino AA-terminal peptides (AAGVAMPGAEDDVVGSGSK; SEQ ID NO: 5) were quantified by qPCR using specific primer sets. For comparison, peptides were immobilized onto beads using a non-hybridization based method that did not involve a ligation step. The non-hybridization based method was performed by incubating 30 µM TCO-modified DNA-tagged peptides including amino FA-terminal peptides, amino AFA-terminal peptides, and amino AA-terminal peptides, with mTet-coated magnetic beads overnight at 25° C.

As shown in Table 1, similar Ct values were observed in the non-hybridization preparation method with 1:100,000 grafting density and the hybridization based preparation method with 1:10,000 grafting density. Loading amount of DNA-tagged peptides for the hybridization based preparation method was 1/3000 compared to that for the non-hybridization preparation method. In general, it was observed that less starting material was needed for the hybridization based immobilization method.

TABLE 1

Comparison of Loading Hybridization and Non-hybridization Immobilization Methods

| Grafting:Passivation | Non-hybridization based immobilization method (−Ligation) | Hybridization based immobilization method (+Ligation) |
| --- | --- | --- |
| 1:100,000 | 19.4 | 25.4 |
| 1:10,000 | — | 21.1 |

In addition, peptides prepared and immobilized as described above were used for peptide sequencing using a ProteoCode assay. Peptides were immobilized on a substrate as described in the two methods described above (hybridization and non-hybridization). Exemplary peptides tested in the assay included amino FA-terminal peptides (FAGVAMPGAEDDVVGSGSK; SEQ ID NO: 3), amino AFA-terminal peptides (AFAGVAMPGAEDDVVGSGSK; SEQ ID NO: 4), and amino AA-terminal peptides (AAGVAMPGAEDDVVGSGSK; SEQ ID NO: 5). Oligonucleotides without a peptide attached were also tested as control.

An exemplary binding agent that binds phenylalanine when it is the N-terminal amino acid residue was conjugated with coding tags (F-binder). For the assay, F-binders conjugated with coding tag were incubated at 37° C. for 30 minutes with beads with nucleic acid-peptide chimera immobilized. After PBST washing, beads were incubated with an encoding mixture containing 50 mM Tris-HCl, pH7.5, 2 mM MgSO$_4$, 50 mM NaCl, 1 mM DTT, 0.1% Tween 20, 0.1 mg/mL BSA, 0.125 mM dNTPs, 0.125 units/µL Klenow fragment (3'→5' exo-) (MCLAB, USA) at 37° C. for 5 minutes. The beads were washed once with PBST+10% formamide, once with 0.1 M NaOH and once with PBST with 10% formamide. The resulting beads were resuspended in PBST. After successful binding of the N-terminal amino acid of the tested peptide with the F binder, the information of the coding tag was transferred to a nucleic acid attached to the immobilized peptide (extended recording tag). The extended recording tags of the assay were subjected to PCR amplification and analyzed by next-generation sequencing (NGS).

TABLE 2

Comparison of Encoding Between Immobilization Methods With and Without Hybridization

| Encoding (%) | Non-hybridization based immobilization method | Hybridization based immobilization method |
| --- | --- | --- |
| Encoding FA peptide (%) | 11.3 | 32.6 |
| Encoding AA peptide (%) | 2.44 | 0.96 |
| Encoding AFA peptide (%) | 3.64 | 2.06 |
| Encoding no peptide (%) | 1.17 | 1.80 |

High encoding efficiencies were observed on the recording tag attached to the amino FA-terminal peptides in the both hybridization and non-hybridization based preparation methods, indicating that the information of coding tags was transferred into recoding tags corresponding to N-terminal F binding. Higher encoding efficiency on the amino FA terminal peptides was observed in samples prepared using the hybridization based method compared to samples prepared using non-hybridization method. In addition, lower encoding efficiencies on the AA and AFA negative control peptides were observed on samples prepared using the hybridization based method. The signal-to-noise (% FA Encoding/% AA Encoding) was 34 on samples prepared using the hybridization based method.

Example 2: Assessment of Encoding Function of Analytes Prepared and Barcoded Using Various Methods This example describes exemplary methods for coupling nucleic acid-analyte conjugates to a solid support and various methods for attaching barcodes, UMIs, or other nucleic acid tags or components to the bait or capture nucleic acid. In this example, the tested formats for immobilizing the peptide analytes included nucleic acid sequences selected from Table 3.

TABLE 3

Exemplary Nucleic Acids

| Description | Sequence 5' to 3' | SEQ ID NO |
|---|---|---|
| Bait DNA | /5Phos/CAAGTTCTCAGTAATGCGTAG/i5OctdU/CCGCGACACTAG | 6 |
| Bait DNA (reverse) | /5SpC3/CTAGTG/i5OctdU/CGCGGACTACG | 7 |
| Capture DNA | GGACTACGCATTACTGAGAACTTGCTAGTCGACGTGGTCCTT/iAmMC6T/TTGGACCACGTCGACTAG | 8 |
| Capture DNA | CACTCAGTCCATTAACNNNNNNNNNNNCTAGTGTCGCGGACUACGCATTACTGAGAAGCTTGCTAGTCGACGTGGTCCTT/iAmMC6T/TTGGACCACGTCGACTAG | 9 |
| Capture DNA | 5Phos/CATTACTGAGAACTTGCTAGTCGACGTGGTCCTT/iAmMC6T/TTGGACCACGTCGACTAG | 10 |
| Capture DNA | /5Phos/CTAGTCGACGTGGTCCTT/iAmMC6T/TTGGACCACGTCGACTAGCGTAGTCCGCGACACTAGNNNNNNNNNNGTTAATGGACTGAGTG | 11 |

Five different methods for installing barcode sequence and immobilizing the peptide were performed and tested. In the methods described below, a barcode sequence and spacer sequence was installed. In some cases, a unique molecule identifier (UMI) can be included in either the bait or reverse bait nucleic acid or can be added with the barcode. In some of the exemplary methods performed, a universal priming site (or a portion thereof) was included in the bait nucleic acid or added with the barcode sequence. In the methods described in this example, hybridization based immobilization of the peptide was performed substantially as described in Example 1, except that in Methods 1, 2, and 3, the beads were washed three times after ligation (PBST, NaOH, and PBST).

In Method 1, which uses a scheme generally depicted in FIG. 3, amino FA peptides (FAGVAMPGAE-DDVVGSGSK; SEQ ID NO: 3) were attached to bait nucleic acids (SEQ ID NO: 6). Barcoding was performed in a 50 µL barcoding mixture including 1× Custom Buffer (New England BioLabs, USA), 0.125 mM dNTPs, 1 µM of bait nucleic acid-peptide chimera, 1.5 µM of a barcode template (CACTCAGTCCAT-TAACNNNNNNNNNNNCTAGTGTCGCGGACUACG-CAUTACUGAGA ACUTG; SEQ ID NO: 12) and 0.125 units/µL Klenow fragment (3'→5' exo-) (MCLAB, USA) at 37° C. for 5 minutes. The barcode templates each contained four dU sites. After transferring the barcode onto the bait nucleic acids (with the peptide attached) by extension, the barcoding templates were digested by incubation at 37° C. for 30 minutes with 2.5 units of USER Enzyme (New England BioLabs, USA). EDTA was added to reaction at 50 mM to quench the polymerase. The resulting barcoded bait nucleic acids (with the peptide attached) were diluted to 10 nM for hybridization based immobilization of the peptides and attachment to capture nucleic acids (sequence as set forth in SEQ ID NO: 8).

In Method 2, which uses a scheme generally depicted in FIG. 4, amino FA peptides (FAGVAMPGAE-DDVVGSGSK; SEQ ID NO: 3) were attached to bait nucleic acids (SEQ ID NO: 6). The bait nucleic acid-peptide chimeras were loaded onto beads which had capture nucleic acids attached. The capture nucleic acids on the beads included a barcode template (CACTCAGTCCAT-TAACNNNNNNNNNNNCTAGTGTCGCGGACUACG-CATTACTGAGA AGCTTGCTAGTCGACGTGGTCCTT/iAmMC6T/TTGGACCACGTCGACTAG; SEQ ID NO: 9) at the 5' end of the capture nucleic acid. The barcode templates each contained one dU site. The bait nucleic acid-peptide chimeras were attached to the capture nucleic acids using hybridized based immobilization and coupling. The barcoding was performed using extension on beads using the barcode template located at the 5' end of the capture nucleic acids. 50 µL of barcoding mixture was used which included 1× Custom Buffer (New England BioLabs, USA), 0.125 mM dNTPs and 0.125 units/µL Klenow fragment (3'→5' exo-) (MCLAB, USA) and the reaction was incubated at 37° C. for 5 minutes. After transferring the barcode onto the bait nucleic acids by extension, the beads were washed twice with PBST. The barcode template on the capture nucleic acids used for extension were digested by incubation at 37° C. for 30 minutes with 2.5 units of USER Enzyme (New England BioLabs, USA). In this method, a Hind III restriction site was formed if extension occurred on capture nucleic acids that did not have bait nucleic acid-peptide chimeras attached. A 50 µL restriction enzyme solution including 1× Custom Buffer and 2.5 Units of Hind III (New England BioLabs, USA) was added to the samples and incubated at 37° C. for 30 minutes to digest these capture nucleic acids that were barcoded but not attached with a bait nucleic acid-peptide chimera. If a bait nucleic-acid peptide chimera was attached to the capture nucleic acid and barcoding occurred by extension onto the bait nucleic acid, then a Hind III site is not formed. The resulting beads were washed once with PBST, once with 0.1 M NaOH and once with PBST.

In Method 3, which uses a scheme generally depicted in FIG. 5, amino FA peptides (FAGVAMPGAE-DDVVGSGSK; SEQ ID NO: 3) were attached to bait nucleic acids (SEQ ID NO: 6). Splint DNAs which contained sequence that is complementary to a portion of the bait nucleic acid and a portion of the barcode were used to bridge the bait nucleic acids and barcodes via hybridization. The barcoding was performed in 50 µL of barcoding mixture including 1× Quick Ligase Buffer (New England BioLabs, USA), 1.5 µM of splint DNA (CCAT-TAACCTAGTGTCGC; SEQ ID NO: 14), 2 µM of barcode (/5Phos/GTTAATGGACTGAGTG; SEQ ID NO: 15), 1 µM bait nucleic acid-tagged peptide and 2.5 units Quick Ligase (New England BioLabs, USA) at 25° C. for 5 minutes. After attaching the barcodes onto the bait nucleic acids of the bait nucleic acid-peptide chimeras, EDTA was added to the reaction at 50 mM to quench the ligase and the splint DNAs were washed away with NaOH. The resulting barcoded bait nucleic acid-peptide chimeras were diluted to 10 nM and attached to capture nucleic acids (sequence as set forth in SEQ ID NO: 8) using the hybridization based method.

In Method 4, which uses a scheme generally depicted in FIG. 6, amino FA peptides (FAGVAMPGAEDDVVGSGSK; SEQ ID NO: 3) were attached to bait nucleic acids (reverse; SEQ ID NO: 7). The bait nucleic acid-peptide chimeras (10 nM) were mixed with 5 nM barcodes (/5Phos/CAAGTTCTCAGTAATGCGTAGTCCGCGACACTAG-NNNNNNNNNNGTTAATG GACTGAGTG; SEQ ID NO: 13) in 50 µL of annealing solution including 5×SSC, 0.02% SDS, and incubated with beads immobilized with phosphorylated capture nucleic acids (SEQ ID NO: 10) for 30 minutes at 37° C. The beads were washed once with PBST and resuspended in 1× Quick ligation solution (New England BioLabs, USA) with T4 DNA ligase to ligate both the nucleic acid-peptide chimera and the barcode to the capture nucleic acid. After a 30 minute-incubation at 25° C., the beads were washed twice with PBST and resuspended in the 50 µl of PBST.

In Method 5, which uses a scheme generally depicted in FIG. 7, amino FA peptides (FAGVAMPGAEDDVVGSGSK; SEQ ID NO: 3) were attached to bait nucleic acids (reverse; SEQ ID NO: 7). The bait nucleic acid-peptide chimeras (10 nM) were annealed to phosphorylated capture nucleic acids that included a barcode sequence (SEQ ID NO: 11) immobilized on beads in 5×SSC, 0.02% SDS, and incubated for 30 minutes at 37° C. The beads were washed once with PBST and resuspended in 1× Quick ligation solution (New England BioLabs, USA) with T4 DNA ligase to attach the bait nucleic acid-peptide chimaeras to the capture nucleic acids. After a 30 minute incubation at 25° C., the beads were washed twice with PBST and resuspended in the 50 µl of PBST.

The immobilized peptides were used for peptide sequencing using a ProteoCode assay substantially as described above using an exemplary binding agent (with attached coding tag) that binds phenylalanine when it is the N-terminal amino acid residue. Exemplary peptides with an amino FA-terminal (FAGVAMPGAEDDVVGSGSK; SEQ ID NO: 3) were used.

Oligonucleotides without a peptide attached were also tested as control. The extended recording tags of the assay were subjected to PCR amplification and analyzed by next-generation sequencing (NGS). As shown in Table 4, all tested methods for immobilizing the peptides and installing barcodes resulted in encoding.

TABLE 4

Assessment of Encoding

| | Method and format of the immobilized nucleic acid-analyte conjugate | | | | |
|---|---|---|---|---|---|
| | Method 1 (FIG. 3) | Method 2 (FIG. 4) | Method 3 (FIG. 5) | Method 4 (FIG. 6) | Method 5 (FIG. 7) |
| Encoding (%) | 33% encoding | 50% encoding | 53% encoding | 22% encoding | 30% encoding |

Example 3: Assessment of Encoding of Peptides with a Functionalized N-Terminal Amino Acid This example describes an exemplary encoding assay for assessing immobilized peptides, performed using binding agents that recognize a functionalized (e.g., modified) N-terminal amino acid on the peptide.

Nucleic acid-peptide chimeras (peptides joined to a bait nucleic acid) were hybridized and ligated to hairpin capture DNAs that were chemically immobilized on agarose beads substantially as described in Example 1. For this experiment, the hairpin capture DNA contained a hybridization sequence complementary to a portion of the bait nucleic acid. After ligating with the bait nucleic acid, the hairpin capture DNA-bait nucleic acid contained an adaptor sequence (universal forward priming site) for downstream sequencing analysis. Various peptides were tested in the encoding assay as set forth in SEQ ID NOs: 25-31, each associated with the indicated nucleic acid sequences in Table 5, which were used as a recording tag (RT) in the assay.

TABLE 5

Exemplary Nucleic Acids

| Description | Sequence 5' to 3' | SEQ ID NO |
|---|---|---|
| Capture Hairpin DNA | /5deSBioTEG//iSp18/AGATCGGAAGAGCGTCGTGTAGGGAAAGAGTGTT T/iAmMC6T/T/iSpC3/ACACTCTTTCCCTACA | 16 |
| RT_for peptide of SEQ ID NO: 25 | /5Phos/C GAC GCT CT/iAmMC6T/ CCG ATC TNNNCCAAACTGAGTG | 17 |
| RT_for peptide of SEQ ID NO: 26 | /5Phos/C GAC GCT CT/iAmMC6T/ CCG ATC TNNNACTAACTGAGTG | 18 |
| RT_for peptide of SEQ ID NO: 27 | /5Phos/C GAC GCT CT/iAmMC6T/ CCG ATC TNNNAAGTACTGAGTG | 19 |
| RT_for peptide of SEQ ID NO: 28 | /5Phos/C GAC GCT CT/iAmMC6T/ CCG ATC TNNNTATGACTGAGTG | 20 |
| RT for peptide of SEQ ID NO: 29 | /5Phos/C GAC GCT CT/iAmMC6T/ CCG ATC TNNNCATAACTGAGTG | 21 |

TABLE 5-continued

Exemplary Nucleic Acids

| Description | Sequence 5' to 3' | SEQ ID NO |
|---|---|---|
| RT_for peptide of SEQ ID NO: 30 | /5Phos/C GAC GCT CT/iAmMC6T/ CCG ATC TNNNGATTACTGAGTG | 22 |
| RT_for peptide of SEQ ID NO: 31 | /5Phos/C GAC GCT CT/iAmMC6T/ CCG ATC TNNNTTAGACTGAGTG | 23 |
| RT only | /5Phos/C GAC GCT CT/iAmMC6T/ CCG ATC TNNNGTAAACTGAGTG | 24 |

In this exemplary model system, cognate binding agents configured to bind to modified N-terminal phenylalanine residues (F) on the immobilized peptides were used. Encoding occurred by transferring information from a coding tag associated with the binding agent to a recording tag associated with the peptide, thereby generating an extended recording tag. For the encoding assay, 200 nM of an exemplary binding agent for phenylalanine (F)) that recognizes the modified NTAA were incubated with peptides treated with an exemplary chemical reagent for modifying the NTAA for 30 min at room temperature. After a quick wash with PBST buffer to remove the excess binding agent, the mixture was incubated with 0.125 units/µL Klenow fragment (3'→5' exo-) (MCLAB, USA), dNTP mixture (125 µM for each), 50 mM Tris-HCl (pH, 7.5), 2 mM MgSO₄, 50 mM NaCl, 1 mM DTT, 0.1% Tween 20, and 0.1 mg/mL BSA at room temperature for 5 min. After washing and capping with a DNA sequence that included a universal reverse priming site (SEQ ID NO: 34-45), the extended recording tags of the assay were subjected to PCR amplification and analyzed by next-generation sequencing (NGS). In this experiment, samples in each well were capped with a capping DNA that contained a barcode that allowed the sample well identity to be determined at a later step, yet allowed samples from different wells were pooled for processing.

Figure 10:
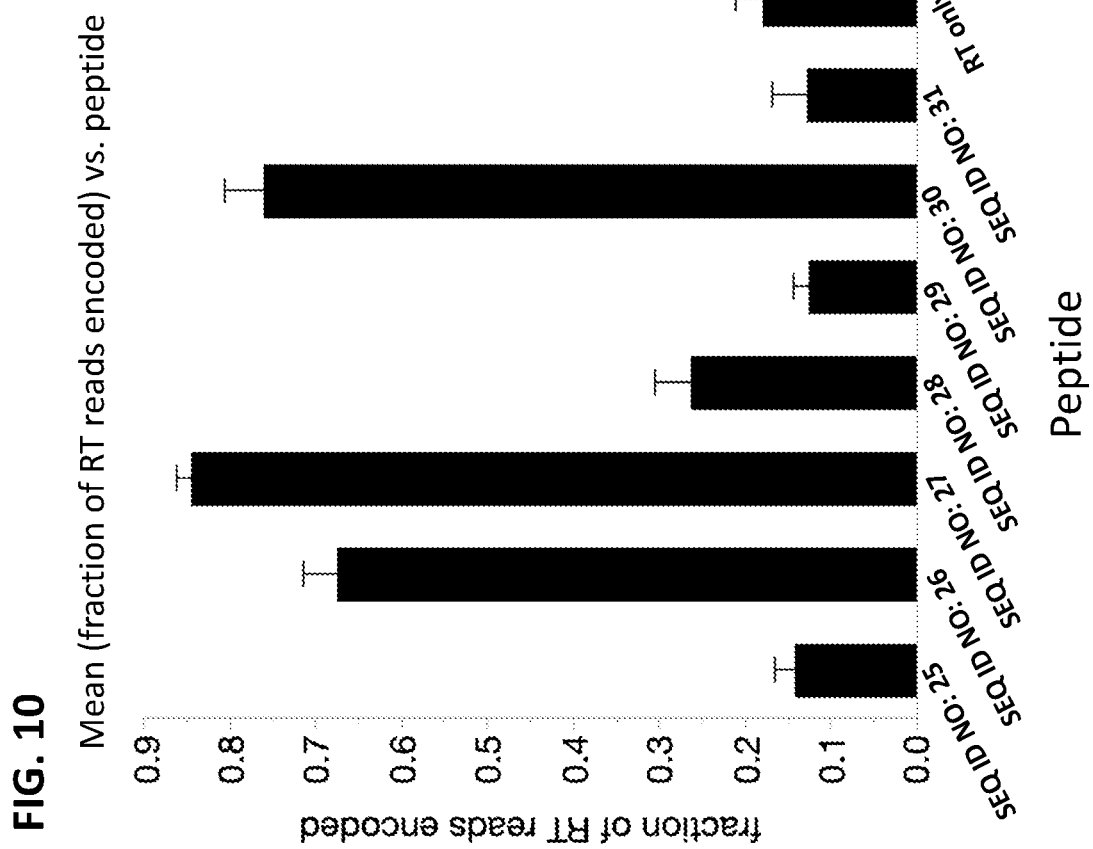
FIG. 10 is a summary of encoding efficiency for various peptides assessed in an exemplary peptide analysis assay using a F-binding agent for modified N-terminal phenylalanine.

FIG. 10 shows the encoding efficiency with the F-binder for peptides tested (including peptides with an N-terminal phenylalanine and other N-terminal amino acids. A recording tag only (RT only) control was also used which was not associated with a peptide. In summary, an increase in F-binder encoding for peptides ending with an N-terminal phenylalanine was detected, demonstrating the use of the hybridization-based immobilization of peptides and exemplary nucleic acids in the encoding assay.

The present disclosure is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE TABLE

| SEQ ID NO | Sequence (5'-3') | Description |
|---|---|---|
| 1 | AATGATACGGCGACCACCGA | P5 primer |
| 2 | CAAGCAGAAGACGGCATACGAGAT | P7 primer |
| 3 | FAGVAMPGAEDDVVGSGSK | FA-terminal peptide |
| 4 | AFAGVAMPGAEDDVVGSGSK | AFA-terminal peptide |
| 5 | AAGVAMPGAEDDVVGSGSK | AA-terminal peptide |
| 6 | /5Phos/CAAGTTCTCAGTAATGCGTAG/i5OctdU/CCGCGACACTAG | Bait DNA |
| 7 | /5SpC3/CTAGTG/i5OctdU/CGCGGACTACG | Reverse Bait DNA |
| 8 | GGACTACGCATTACTGAGAACTTGCTAGTCGACGTGGTCCTT/iAmMC6T/TTGGACCACGTCGACTAG | Capture DNA |
| 9 | CACTCAGTCCATTAACNNNNNNNNNNNCTAGTGTCGCGGACUACGCATTACTGAGAAGCTTGCTAGTCGACGTGGTCCTT/iAmMC6T/TTGGACCACGTCGACTAG | Capture DNA |

-continued

SEQUENCE TABLE

| SEQ ID NO | Sequence (5'-3') | Description |
|---|---|---|
| 10 | 5Phos/CATTACTGAGAACTTGCTAGTCGACGTGGTCCTT/iAmMC6T/TTGGACCACGTCGACTAG | Capture DNA |
| 11 | /5Phos/CTAGTCGACGTGGTCCTT/iAmMC6T/TTGGACCACGTCGACTAGCGTAGTCCGCGACACTAGNNNNNNNNNNNGTTAATGGACTGAGTG | Capture DNA |
| 12 | CACTCAGTCCATTAACNNNNNNNNNNCTAGTGTCGCGGACUACGCAUTACUGAGAACUTG | Barcode Template |
| 13 | /5Phos/CAAGTTCTCAGTAATGCGTAGTCCGCGACACTAGNNNNNNNNNNGTTAATGGACTGAGTG | Barcode |
| 14 | CCATTAACCTAGTGTCGC | Splint DNA |
| 15 | /5Phos/GTTAATGGACTGAGTG | Barcode Template |
| 16 | /5deSBioTEG//iSp18/AGATCGGAAGAGCGTCGTGTAGGGAAAGAGTGTTT/iAmMC6T/T/iSpC3/ACACTCTTTCCCTACA | Capture Hairpin DNA |
| 17 | /5Phos/C GAC GCT CT/iAmMC6T/ CCG ATC TNNNCCAAACTGAGTG | Recording Tag |
| 18 | /5Phos/C GAC GCT CT/iAmMC6T/ CCG ATC TNNNACTAACTGAGTG | Recording Tag |
| 19 | /5Phos/C GAC GCT CT/iAmMC6T/ CCG ATC TNNNAAGTACTGAGTG | Recording Tag |
| 20 | /5Phos/C GAC GCT CT/iAmMC6T/ CCG ATC TNNNTATGACTGAGTG | Recording Tag |
| 21 | /5Phos/C GAC GCT CT/iAmMC6T/ CCG ATC TNNNCATAACTGAGTG | Recording Tag |
| 22 | /5Phos/C GAC GCT CT/iAmMC6T/ CCG ATC TNNNGATTACTGAGTG | Recording Tag |
| 23 | /5Phos/C GAC GCT CT/iAmMC6T/ CCG ATC TNNNTTAGACTGAGTG | Recording Tag |
| 24 | /5Phos/C GAC GCT CT/iAmMC6T/ CCG ATC TNNNGTAAACTGAGTG | Recording Tag |
| 25 | LAGELAGELAGEIRGDVRGGK(N3)-NH2 | Assay Peptide |
| 26 | FAGVAMPGAEDDVVGS GS K(azide)-NH2 | Assay Peptide |
| 27 | FLAEIRGDVRGGK(Azide) | Assay Peptide |
| 28 | SGVARGDVRGGK(azide)-NH2 | Assay Peptide |
| 29 | dimethyl-AESAESASRFSGVAMPGAEDDVVGSGSK(azide)-OH | Assay Peptide |
| 30 | FSGVARGDVRGGK(azide)-NH2 | Assay Peptide |
| 31 | LAESAFSGVARGDVRGGK(azide)-NH2 | Assay Peptide |
| 32 | ACACTCTTTCCCTACACGACGCTCTTCCGATCT | Forward Priming Site |
| 33 | GACTGGAGTTCAGACGTGTGCTCTTCCGATCT | Reverse Priming Site |
| 34 | GAC TGG AGT TCA GAC GTG TGC TCT TCC GAT CTT TCT ACT CTT CTC ACT CAG T/3SpC3/ | Capping DNA |
|  | GAC TGG AGT TCA GAC GTG TGC TCT TCC GAT CTT CTT ACT CTT CTC ACT CAG T/3SpC3/ | Capping DNA |
| 36 | GAC TGG AGT TCA GAC GTG TGC TCT TCC GAT CTT GGT ACT CTT CTC ACT CAG T/3SpC3/ | Capping DNA |
| 37 | GAC TGG AGT TCA GAC GTG TGC TCT TCC GAT CTT AAT ACT CTT CTC ACT CAG T/3SpC3/ | Capping DNA |
| 38 | GAC TGG AGT TCA GAC GTG TGC TCT TCC GAT CTC TTT ACT CTT CTC ACT CAG T/3SpC3/ | Capping DNA |
| 39 | GAC TGG AGT TCA GAC GTG TGC TCT TCC GAT CTC CGT ACT CTT CTC ACT CAG T/3SpC3/ | Capping DNA |

-continued

SEQUENCE TABLE

| SEQ ID NO | Sequence (5'-3') | Description |
|---|---|---|
| 40 | GAC TGG AGT TCA GAC GTG TGC TCT TCC GAT CTC GCT ACT CTT CTC ACT CAG T/3SpC3/ | Capping DNA |
| 41 | GAC TGG AGT TCA GAC GTG TGC TCT TCC GAT CTG TGT ACT CTT CTC ACT CAG T/3SpC3/ | Capping DNA |
| 42 | GAC TGG AGT TCA GAC GTG TGC TCT TCC GAT CTG CCT ACT CTT CTC ACT CAG T/3SpC3/ | Capping DNA |
| 43 | GAC TGG AGT TCA GAC GTG TGC TCT TCC GAT CTG GTT ACT CTT CTC ACT CAG T/3SpC3/ | Capping DNA |
| 44 | GAC TGG AGT TCA GAC GTG TGC TCT TCC GAT CTA TAT ACT CTT CTC ACT CAG T/3SpC3/ | Capping DNA |
| 45 | GAC TGG AGT TCA GAC GTG TGC TCT TCC GAT CTA ATT ACT CTT CTC ACT CAG T/3SpC3/ | Capping DNA |

What is claimed is:

1. A method for treating a polypeptide analyte, comprising:
- attaching the polypeptide analyte to a bait nucleic acid to generate a nucleic acid-analyte chimera, wherein the bait nucleic acid is covalently attached to the polypeptide analyte to generate the nucleic acid-analyte chimera;
- bringing the nucleic acid-analyte chimera into proximity with a solid support by hybridizing the bait nucleic acid in the nucleic acid-analyte chimera to a capture nucleic acid attached to the solid support;
- covalently coupling the nucleic acid-analyte chimera to the solid support, wherein a plurality of the nucleic acid-analyte chimeras is coupled on the solid support and adjacent nucleic acid-analyte chimeras coupled on the solid support are spaced apart from each other at an average distance of about 50 nm or greater;
- contacting the polypeptide analyte covalently coupled to the solid support with a binding agent capable of binding to the polypeptide analyte, wherein the binding agent comprises a coding tag that comprises identifying information regarding the binding agent; and
- transferring the identifying information regarding the binding agent from the coding tag to the bait nucleic acid or capture nucleic acid attached to the polypeptide analyte.

2. The method of claim 1, wherein the polypeptide analyte is attached to the 3' end of the bait nucleic acid or to the 5' end of the bait nucleic acid.

3. The method of claim 1, wherein the polypeptide analyte is attached to an internal position of the bait nucleic acid.

4. The method of claim 1, further comprising attaching a barcode to the coupled nucleic acid-analyte chimera, wherein the barcode comprises a compartment barcode, a partition barcode, a sample barcode, a fraction barcode, or any combination thereof.

5. The method of claim 1, wherein the polypeptide analyte is obtained by fragmenting proteins from a biological sample.

6. The method of claim 1, wherein the bait nucleic acid and/or capture nucleic acid further comprises a universal priming site, wherein the universal priming site comprises a priming site for amplification, sequencing, or both.

7. The method of claim 1, further comprising repeating one or more times:
- contacting the polypeptide analyte with an additional binding agent capable of binding to the polypeptide analyte, wherein the additional binding agent comprises a coding tag that comprises identifying information regarding the additional binding agent; and
- transferring the identifying information regarding the additional binding agent from the coding tag to the bait nucleic acid or capture nucleic acid attached to the polypeptide analyte.

8. The method of claim 1, wherein adjacent nucleic acid-analyte chimeras coupled on the solid support are spaced apart from each other at an average distance of about 100 nm or greater.

9. The method of claim 1, wherein adjacent nucleic acid-analyte chimeras coupled on the solid support are spaced apart from each other at an average distance of about 250 nm or greater.

10. The method of claim 1, comprising covalently coupling the bait nucleic acid in the nucleic acid-analyte chimera to the capture nucleic acid attached to the solid support, thereby covalently coupling the nucleic acid-analyte chimera to the solid support.

11. The method of claim 10, wherein the covalent coupling comprises covalently cross-linking the bait nucleic acid and the capture nucleic acid.

12. The method of claim 10, wherein the covalent coupling comprises enzymatic ligation or chemical ligation of the bait nucleic acid and the capture nucleic acid.

13. The method of claim 1, wherein the bait nucleic acid or the capture nucleic acid comprises a splint nucleic acid strand that bridges the bait nucleic acid and the capture nucleic acid via hybridization for covalent coupling of the bait nucleic acid and the capture nucleic acid.

14. The method of claim 13, wherein the capture nucleic acid comprises the splint nucleic acid strand which comprises a sequence complementary to the bait nucleic acid.

15. The method of claim 1, wherein the capture nucleic acid comprises an intramolecular duplex formed between mutually complementary nucleic acid regions, and the capture nucleic acid comprises a loop region connecting the mutually complementary nucleic acid regions.

16. The method of claim 1, wherein the polypeptide analyte is indirectly attached to the bait nucleic acid via a linker and the nucleic acid-analyte chimera is indirectly coupled to the solid support.

17. The method of claim 1, wherein the solid support is a porous bead.

18. The method of claim 1, wherein the capture nucleic acid comprises a nucleic acid hairpin.

19. The method of claim 1, wherein the transfer of the identifying information regarding the binding agent from the coding tag to the bait nucleic acid or capture nucleic acid occurs through a primer extension reaction or ligation.

20. A nucleic acid-analyte composition comprising a plurality of nucleic acid-analyte chimeras and a plurality of capture nucleic acids attached to a solid support, the nucleic acid-analyte composition generated by the steps of:

attaching a polypeptide analyte to a bait nucleic acid to generate a nucleic acid-analyte chimera, wherein the bait nucleic acid is covalently attached to the polypeptide analyte to generate the nucleic acid-analyte chimera;

bringing the nucleic acid-analyte chimera into proximity with the solid support by hybridizing the bait nucleic acid in the nucleic acid-analyte chimera to a capture nucleic acid attached to the solid support;

covalently coupling the nucleic acid-analyte chimera to the solid support, wherein the plurality of nucleic acid-analyte chimeras is coupled on the solid support and adjacent nucleic acid-analyte chimeras coupled on the solid support are spaced apart at an average distance of about 50 nm or greater;

contacting the polypeptide analyte covalently coupled to the solid support with a binding agent capable of binding to the polypeptide analyte, wherein the binding agent comprises a coding tag that comprises identifying information regarding the binding agent; and transferring the identifying information regarding the binding agent from the coding tag to the bait nucleic acid or capture nucleic acid attached to the polypeptide analyte.

21. The nucleic acid-analyte composition of claim 20, wherein the polypeptide analyte is attached to the 3' end of the bait nucleic acid or to the 5' end of the bait nucleic acid.

22. The nucleic acid-analyte composition of claim 20, wherein the capture nucleic acid, the nucleic acid-analyte chimera, and/or the bait nucleic acid further comprises a barcode.

23. The nucleic acid-analyte composition of claim 20, wherein the capture nucleic acid comprises a nucleic acid hairpin.

24. The nucleic acid-analyte composition of claim 20, wherein the bait nucleic acid and/or capture nucleic acid further comprises a universal priming site, wherein the universal priming site comprises a priming site for amplification, sequencing or both.

25. The nucleic acid-analyte composition of claim 20, wherein the solid support is a porous bead.

26. A kit for polypeptide analysis, comprising:
(a) a plurality of bait nucleic acids, each of the bait nucleic acids is configured to be covalently attached to a polypeptide analyte;
(b) a solid support comprising a plurality of capture nucleic acids attached hereto, each of the capture nucleic acids comprising a sequence complementary to a corresponding bait nucleic acid of the plurality of bait nucleic acids and configured to covalently couple the polypeptide analyte to the solid support, wherein adjacent capture nucleic acids are spaced apart on the solid support at an average distance of about 50 nm or greater; and
(c) one or more binding agents capable of binding to the polypeptide analyte, wherein each binding agent comprises a coding tag that comprises identifying information regarding the binding agent, and wherein the coding tag is configured to allow transfer of the identifying information regarding the binding agent to the bait nucleic acid or capture nucleic acid attached to the polypeptide analyte immobilized on the solid support.

27. The kit of claim 26, wherein at least one of the bait nucleic acids is configured to allow the polypeptide analyte to be attached to the 3' end of the bait nucleic acid or to the 5' end of the bait nucleic acid.

28. The kit of claim 26, further comprising a plurality of barcodes, wherein the barcodes are attached to the bait nucleic acid or the capture nucleic acid, or the barcodes are configured to be attached to the bait nucleic acid or the capture nucleic acid.

29. The kit of claim 26, wherein at least one of the bait nucleic acids comprises a reactive coupling moiety configured for attachment to the polypeptide analyte or to at least one of the capture nucleic acids.

30. The kit of claim 26, wherein at least one of the capture nucleic acids comprises a nucleic acid hairpin.

* * * * *

SEQUENCE LISTING

<160> NUMBER OF SEQ ID NOS: 45

<210> SEQ ID NO 1
<211> LENGTH: 20
<212> TYPE: DNA
<213> ORGANISM: Artificial Sequence
<220> FEATURE:
<223> OTHER INFORMATION: P5 primer

<400> SEQUENCE: 1
aatgatacgg cgaccaccga                    20

<210> SEQ ID NO 2
<211> LENGTH: 24
<212> TYPE: DNA
<213> ORGANISM: Artificial Sequence
<220> FEATURE:
<223> OTHER INFORMATION: P7 primer

<400> SEQUENCE: 2
caagcagaag acggcatacg agat                24

<210> SEQ ID NO 3
<211> LENGTH: 19
<212> TYPE: PRT
<213> ORGANISM: Artificial Sequence
<220> FEATURE:
<223> OTHER INFORMATION: FA-terminal peptide

<400> SEQUENCE: 3

Phe Ala Gly Val Ala Met Pro Gly Ala Glu Asp Asp Val Val Gly Ser
1               5                   10                  15

Gly Ser Lys

<210> SEQ ID NO 4
<211> LENGTH: 20
<212> TYPE: PRT
<213> ORGANISM: Artificial Sequence
<220> FEATURE:
<223> OTHER INFORMATION: AFA-terminal peptide

```
<400> SEQUENCE: 4

Ala Phe Ala Gly Val Ala Met Pro Gly Ala Glu Asp Asp Val Val Gly
1               5                   10                  15

Ser Gly Ser Lys
            20

<210> SEQ ID NO 5
<211> LENGTH: 19
<212> TYPE: PRT
<213> ORGANISM: Artificial Sequence
<220> FEATURE:
<223> OTHER INFORMATION: AA-terminal peptide

<400> SEQUENCE: 5

Ala Ala Gly Val Ala Met Pro Gly Ala Glu Asp Asp Val Val Gly Ser
1               5                   10                  15

Gly Ser Lys

<210> SEQ ID NO 6
<211> LENGTH: 34
<212> TYPE: DNA
<213> ORGANISM: Artificial Sequence
<220> FEATURE:
<223> OTHER INFORMATION: Bail DNA
<220> FEATURE:
<221> NAME/KEY: misc_feature
<222> LOCATION: (1)..(1)
<223> OTHER INFORMATION: 5' phosphorylated
<220> FEATURE:
<221> NAME/KEY: misc_feature
<222> LOCATION: (22)..(22)
<223> OTHER INFORMATION: n is an internal 5'-Octadiynyl dU

<400> SEQUENCE: 6
caagttctca gtaatgcgta gnccgcgaca ctag                              34

<210> SEQ ID NO 7
<211> LENGTH: 18
<212> TYPE: DNA
<213> ORGANISM: Artificial Sequence
<220> FEATURE:
<223> OTHER INFORMATION: Reverse Bait DNA
<220> FEATURE:
<221> NAME/KEY: misc_feature
<222> LOCATION: (1)..(1)
<223> OTHER INFORMATION: 5' C3 (three carbon) spacer
<220> FEATURE:
<221> NAME/KEY: misc_feature
<222> LOCATION: (7)..(7)
<223> OTHER INFORMATION: n is an internal 5'-Octadiynyl dU

<400> SEQUENCE: 7
ctagtgncgc ggactacg                                                18

<210> SEQ ID NO 8
<211> LENGTH: 61
<212> TYPE: DNA
<213> ORGANISM: Artificial Sequence
<220> FEATURE:
<223> OTHER INFORMATION: Capture DNA
<220> FEATURE:
<221> NAME/KEY: misc_feature
<222> LOCATION: (43)..(43)
<223> OTHER INFORMATION: n is an internal amino modifier C6 dT
```

<400> SEQUENCE: 8
ggactacgca ttactgagaa cttgctagtc gacgtggtcc ttnttggacc acgtcgacta    60
g                                                                   61

<210> SEQ ID NO 9
<211> LENGTH: 98
<212> TYPE: DNA
<213> ORGANISM: Artificial Sequence
<220> FEATURE:
<223> OTHER INFORMATION: Capture DNA
<220> FEATURE:
<221> NAME/KEY: misc_feature
<222> LOCATION: (17)..(26)
<223> OTHER INFORMATION: n is a, c, g, or t
<220> FEATURE:
<221> NAME/KEY: misc_feature
<222> LOCATION: (80)..(80)
<223> OTHER INFORMATION: n is an internal amino modifier C6 dT

<400> SEQUENCE: 9
cactcagtcc attaacnnnn nnnnnnctag tgtcgcggac uacgcattac tgagaagctt    60
gctagtcgac gtggtccttn ttggaccacg tcgactag                            98

<210> SEQ ID NO 10
<211> LENGTH: 53
<212> TYPE: DNA
<213> ORGANISM: Artificial Sequence
<220> FEATURE:
<223> OTHER INFORMATION: Capture DNA
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (35)..(35)
<223> OTHER INFORMATION: n is an internal 5'-amino modifier C6 dT

<400> SEQUENCE: 10
cattactgag aacttgctag tcgacgtggt ccttnttgga ccacgtcgac tag           53

<210> SEQ ID NO 11
<211> LENGTH: 81
<212> TYPE: DNA
<213> ORGANISM: Artificial Sequence
<220> FEATURE:
<223> OTHER INFORMATION: Capture DNA
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (19)..(19)
<223> OTHER INFORMATION: n is an internal 5'-amino modifier C6 dT
<220> FEATURE:
<221> NAME/KEY: misc_feature
<222> LOCATION: (56)..(65)
<223> OTHER INFORMATION: n is a, c, g, or t

<400> SEQUENCE: 11
ctagtcgacg tggtccttnt tggaccacgt cgactagcgt agtccgcgac actagnnnnn    60
nnnnngttaa tggactgagt g                                              81

<210> SEQ ID NO 12
<211> LENGTH: 60
<212> TYPE: DNA
<213> ORGANISM: Artificial Sequence

```
<220> FEATURE:
<223> OTHER INFORMATION: Barcode Template
<220> FEATURE:
<221> NAME/KEY: misc_feature
<222> LOCATION: (17)..(26)
<223> OTHER INFORMATION: n is a, c, g, or t

<400> SEQUENCE: 12
cactcagtcc attaacnnnn nnnnnnctag tgtcgcggac uacgcautac ugagaacutg      60

<210> SEQ ID NO 13
<211> LENGTH: 60
<212> TYPE: DNA
<213> ORGANISM: Artificial Sequence
<220> FEATURE:
<223> OTHER INFORMATION: Barcode
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (35)..(44)
<223> OTHER INFORMATION: n is a, c, g, or t

<400> SEQUENCE: 13
caagttctca gtaatgcgta gtccgcgaca ctagnnnnn nnnngttaat ggactgagtg       60

<210> SEQ ID NO 14
<211> LENGTH: 18
<212> TYPE: DNA
<213> ORGANISM: Artificial Sequence
<220> FEATURE:
<223> OTHER INFORMATION: Splint DNA

<400> SEQUENCE: 14
ccattaacct agtgtcgc                                                    18

<210> SEQ ID NO 15
<211> LENGTH: 16
<212> TYPE: DNA
<213> ORGANISM: Artificial Sequence
<220> FEATURE:
<223> OTHER INFORMATION: Barcode Template
<220> FEATURE:
<221> NAME/KEY: misc_feature
<222> LOCATION: (1)..(1)
<223> OTHER INFORMATION: 5'-phosphorylated

<400> SEQUENCE: 15
gttaatggac tgagtg                                                      16

<210> SEQ ID NO 16
<211> LENGTH: 53
<212> TYPE: DNA
<213> ORGANISM: Artificial Sequence
<220> FEATURE:
<223> OTHER INFORMATION: Capture Hairpin DNA
<220> FEATURE:
<221> NAME/KEY: misc_feature
<222> LOCATION: (1)..(1)
<223> OTHER INFORMATION: 5'-(5' desthiobiotin-TEG and an internal
      18-atom hexa-ethyleneglycol spacer)
<220> FEATURE:
<221> NAME/KEY: misc_feature
<222> LOCATION: (36)..(36)
<223> OTHER INFORMATION: n is an internal 5'-amino modifier C6 dT
<220> FEATURE:
<221> NAME/KEY: misc_feature
<222> LOCATION: (37)..(38)
<223> OTHER INFORMATION: C3 (three carbon) spacer inserted in between
```

<400> SEQUENCE: 16
agatcggaag agcgtcgtgt agggaaagag tgtttntaca ctctttccct aca         53

<210> SEQ ID NO 17
<211> LENGTH: 32
<212> TYPE: DNA
<213> ORGANISM: Artificial Sequence
<220> FEATURE:
<223> OTHER INFORMATION: Recording Tag
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (10)..(10)
<223> OTHER INFORMATION: n is an internal 5'-amino modifier C6 dT
<220> FEATURE:
<221> NAME/KEY: misc_feature
<222> LOCATION: (18)..(20)
<223> OTHER INFORMATION: n is a, c, g, or t

<400> SEQUENCE: 17
cgacgctctn ccgatctnnn ccaaactgag tg                                32

<210> SEQ ID NO 18
<211> LENGTH: 32
<212> TYPE: DNA
<213> ORGANISM: Artificial Sequence
<220> FEATURE:
<223> OTHER INFORMATION: Recording Tag
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (10)..(10)
<223> OTHER INFORMATION: n is an internal amino modifier C6 dT
<220> FEATURE:
<221> NAME/KEY: misc_feature
<222> LOCATION: (18)..(20)
<223> OTHER INFORMATION: n is a, c, g, or t

<400> SEQUENCE: 18
cgacgctctn ccgatctnnn actaactgag tg                                32

<210> SEQ ID NO 19
<211> LENGTH: 32
<212> TYPE: DNA
<213> ORGANISM: Artificial Sequence
<220> FEATURE:
<223> OTHER INFORMATION: Recording Tag
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (10)..(10)
<223> OTHER INFORMATION: n is an internal amino modifier C6 dT
<220> FEATURE:
<221> NAME/KEY: misc_feature
<222> LOCATION: (18)..(20)
<223> OTHER INFORMATION: n is a, c, g, or t

<400> SEQUENCE: 19
cgacgctctn ccgatctnnn aagtactgag tg                                32

```
<210> SEQ ID NO 20
<211> LENGTH: 32
<212> TYPE: DNA
<213> ORGANISM: Artificial Sequence
<220> FEATURE:
<223> OTHER INFORMATION: Recording Tag
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (10)..(10)
<223> OTHER INFORMATION: n is an internal amino modifier C6 dT
<220> FEATURE:
<221> NAME/KEY: misc_feature
<222> LOCATION: (18)..(20)
<223> OTHER INFORMATION: n is a, c, g, or t

<400> SEQUENCE: 20
cgacgctctn ccgatctnnn tatgactgag tg                                   32

<210> SEQ ID NO 21
<211> LENGTH: 32
<212> TYPE: DNA
<213> ORGANISM: Artificial Sequence
<220> FEATURE:
<223> OTHER INFORMATION: Recording Tag
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (10)..(10)
<223> OTHER INFORMATION: n is an internal amino modifier C6 dT
<220> FEATURE:
<221> NAME/KEY: misc_feature
<222> LOCATION: (18)..(20)
<223> OTHER INFORMATION: n is a, c, g, or t

<400> SEQUENCE: 21
cgacgctctn ccgatctnnn cataactgag tg                                   32

<210> SEQ ID NO 22
<211> LENGTH: 32
<212> TYPE: DNA
<213> ORGANISM: Artificial Sequence
<220> FEATURE:
<223> OTHER INFORMATION: Recording Tag
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (10)..(10)
<223> OTHER INFORMATION: n is an internal amino modifier C6 dT
<220> FEATURE:
<221> NAME/KEY: misc_feature
<222> LOCATION: (18)..(20)
<223> OTHER INFORMATION: n is a, c, g, or t

<400> SEQUENCE: 22
cgacgctctn ccgatctnnn gattactgag tg                                   32

<210> SEQ ID NO 23
<211> LENGTH: 32
<212> TYPE: DNA
<213> ORGANISM: Artificial Sequence
<220> FEATURE:
<223> OTHER INFORMATION: Recording Tag
```

```
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (10)..(10)
<223> OTHER INFORMATION: n is an internal amino modifier C6 dT
<220> FEATURE:
<221> NAME/KEY: misc_feature
<222> LOCATION: (18)..(20)
<223> OTHER INFORMATION: n is a, c, g, or t

<400> SEQUENCE: 23
cgacgctctn ccgatctnnn ttagactgag tg                                    32

<210> SEQ ID NO 24
<211> LENGTH: 32
<212> TYPE: DNA
<213> ORGANISM: Artificial Sequence
<220> FEATURE:
<223> OTHER INFORMATION: Recording Tag
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (10)..(10)
<223> OTHER INFORMATION: n is an internal amino modifier C6 dT
<220> FEATURE:
<221> NAME/KEY: misc_feature
<222> LOCATION: (18)..(20)
<223> OTHER INFORMATION: n is a, c, g, or t

<400> SEQUENCE: 24
cgacgctctn ccgatctnnn gtaaactgag tg                                    32

<210> SEQ ID NO 25
<211> LENGTH: 21
<212> TYPE: PRT
<213> ORGANISM: Artificial Sequence
<220> FEATURE:
<223> OTHER INFORMATION: Assay Peptide
<220> FEATURE:
<221> NAME/KEY: MISC_FEATURE
<222> LOCATION: (21)..(21)
<223> OTHER INFORMATION: C-terminal amide
<220> FEATURE:
<221> NAME/KEY: MISC_FEATURE
<222> LOCATION: (21)..(21)
<223> OTHER INFORMATION: an azido substituent on the lysine side chain

<400> SEQUENCE: 25

Leu Ala Gly Glu Leu Ala Gly Glu Leu Ala Gly Glu Ile Arg Gly Asp
1               5                   10                  15

Val Arg Gly Gly Lys
            20

<210> SEQ ID NO 26
<211> LENGTH: 19
<212> TYPE: PRT
<213> ORGANISM: Artificial Sequence
<220> FEATURE:
<223> OTHER INFORMATION: Assay Peptide
<220> FEATURE:
<221> NAME/KEY: MISC_FEATURE
<222> LOCATION: (19)..(19)
<223> OTHER INFORMATION: C-terminal amide
```

```
<220> FEATURE:
<221> NAME/KEY: MISC_FEATURE
<222> LOCATION: (19)..(19)
<223> OTHER INFORMATION: an azido substituent on the lysine side chain

<400> SEQUENCE: 26

Phe Ala Gly Val Ala Met Pro Gly Ala Glu Asp Asp Val Val Gly Ser
1               5                   10                  15

Gly Ser Lys

<210> SEQ ID NO 27
<211> LENGTH: 13
<212> TYPE: PRT
<213> ORGANISM: Artificial Sequence
<220> FEATURE:
<223> OTHER INFORMATION: Assay Peptide
<220> FEATURE:
<221> NAME/KEY: MISC_FEATURE
<222> LOCATION: (13)..(13)
<223> OTHER INFORMATION: an azido substituent on the lysine side chain

<400> SEQUENCE: 27

Phe Leu Ala Glu Ile Arg Gly Asp Val Arg Gly Gly Lys
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Assay Peptide
<220> FEATURE:
<221> NAME/KEY: MISC_FEATURE
<222> LOCATION: (12)..(12)
<223> OTHER INFORMATION: C-terminal amide
<220> FEATURE:
<221> NAME/KEY: MISC_FEATURE
<222> LOCATION: (12)..(12)
<223> OTHER INFORMATION: an azido substituent on the lysine side chain

<400> SEQUENCE: 28

Ser Gly Val Ala Arg Gly Asp Val Arg Gly Gly Lys
1               5                   10

<210> SEQ ID NO 29
<211> LENGTH: 28
<212> TYPE: PRT
<213> ORGANISM: Artificial Sequence
<220> FEATURE:
<223> OTHER INFORMATION: Assay Peptide
<220> FEATURE:
<221> NAME/KEY: MISC_FEATURE
<222> LOCATION: (1)..(1)
<223> OTHER INFORMATION: N-terminal dimethyl group
<220> FEATURE:
<221> NAME/KEY: MISC_FEATURE
<222> LOCATION: (28)..(28)
<223> OTHER INFORMATION: an azido substituent on the lysine side chain

<400> SEQUENCE: 29

Ala Glu Ser Ala Glu Ser Ala Ser Arg Phe Ser Gly Val Ala Met Pro
1               5                   10                  15

Gly Ala Glu Asp Asp Val Val Gly Ser Gly Ser Lys
            20                  25

<210> SEQ ID NO 30
<211> LENGTH: 13
<212> TYPE: PRT
<213> ORGANISM: Artificial Sequence
```

```
<220> FEATURE:
<223> OTHER INFORMATION: Assay Peptide
<220> FEATURE:
<221> NAME/KEY: MISC_FEATURE
<222> LOCATION: (13)..(13)
<223> OTHER INFORMATION: C-terminal amide
<220> FEATURE:
<221> NAME/KEY: MISC_FEATURE
<222> LOCATION: (13)..(13)
<223> OTHER INFORMATION: an azido substituent on the lysine side chain

<400> SEQUENCE: 30

Phe Ser Gly Val Ala Arg Gly Asp Val Arg Gly Gly Lys
1               5                   10

<210> SEQ ID NO 31
<211> LENGTH: 18
<212> TYPE: PRT
<213> ORGANISM: Artificial Sequence
<220> FEATURE:
<223> OTHER INFORMATION: Assay Peptide
<220> FEATURE:
<221> NAME/KEY: MISC_FEATURE
<222> LOCATION: (18)..(18)
<223> OTHER INFORMATION: C-terminal amide
<220> FEATURE:
<221> NAME/KEY: MISC_FEATURE
<222> LOCATION: (18)..(18)
<223> OTHER INFORMATION: an azido substituent on the lysine side chain

<400> SEQUENCE: 31

Leu Ala Glu Ser Ala Phe Ser Gly Val Ala Arg Gly Asp Val Arg Gly
1               5                   10                  15

Gly Lys

<210> SEQ ID NO 32
<211> LENGTH: 33
<212> TYPE: DNA
<213> ORGANISM: Artificial Sequence
<220> FEATURE:
<223> OTHER INFORMATION: Forward Priming Site

<400> SEQUENCE: 32
acactctttc cctacacgac gctcttccga tct                              33

<210> SEQ ID NO 33
<211> LENGTH: 32
<212> TYPE: DNA
<213> ORGANISM: Artificial Sequence
<220> FEATURE:
<223> OTHER INFORMATION: Reverse Priming Site

<400> SEQUENCE: 33
gactggagtt cagacgtgtg ctcttccgat ct                               32

<210> SEQ ID NO 34
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 34
gactggagtt cagacgtgtg ctcttccgat ctttctactc ttctcactca gt         52
```

-continued

```
<210> SEQ ID NO 35
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 35
gactggagtt cagacgtgtg ctcttccgat cttcttactc ttctcactca gt        52

<210> SEQ ID NO 36
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 36
gactggagtt cagacgtgtg ctcttccgat cttggtactc ttctcactca gt        52

<210> SEQ ID NO 37
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 37
gactggagtt cagacgtgtg ctcttccgat cttaatactc ttctcactca gt        52

<210> SEQ ID NO 38
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 38
gactggagtt cagacgtgtg ctcttccgat ctctttactc ttctcactca gt        52

<210> SEQ ID NO 39
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 39
gactggagtt cagacgtgtg ctcttccgat ctccgtactc ttctcactca gt        52
```

```
<210> SEQ ID NO 40
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 40
gactggagtt cagacgtgtg ctcttccgat ctcgctactc ttctcactca gt        52

<210> SEQ ID NO 41
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 41
gactggagtt cagacgtgtg ctcttccgat ctgtgtactc ttctcactca gt        52

<210> SEQ ID NO 42
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 42
gactggagtt cagacgtgtg ctcttccgat ctgcctactc ttctcactca gt        52

<210> SEQ ID NO 43
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: C'-C3 (three carbon) spacer

<400> SEQUENCE: 43
gactggagtt cagacgtgtg ctcttccgat ctggttactc ttctcactca gt        52

<210> SEQ ID NO 44
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: Capping DNA

<400> SEQUENCE: 44
gactggagtt cagacgtgtg ctcttccgat ctatatactc ttctcactca gt        52
```

```
<210> SEQ ID NO 45
<211> LENGTH: 52
<212> TYPE: DNA
<213> ORGANISM: Artificial Sequence
<220> FEATURE:
<223> OTHER INFORMATION: Capping DNA
<220> FEATURE:
<221> NAME/KEY: misc_feature
<222> LOCATION: (52)..(52)
<223> OTHER INFORMATION: 3'-C3 (three carbon) spacer

<400> SEQUENCE: 45
gactggagtt cagacgtgtg ctcttccgat ctaattactc ttctcactca gt          52
```